United States Patent
Gentry et al.

(10) Patent No.: US 9,410,133 B1
(45) Date of Patent: Aug. 9, 2016

(54) GLUCAN PHOSPHATASE VARIANTS FOR STARCH PHOSPHORYLATION

(71) Applicant: University of Kentucky Research Foundation, Lexington, KY (US)

(72) Inventors: Matthew Gentry, Lexington, KY (US); Craig Vander Kooi, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 106 days.

(21) Appl. No.: 13/928,160

(22) Filed: Jun. 26, 2013

Related U.S. Application Data

(60) Provisional application No. 61/673,476, filed on Jul. 19, 2012.

(51) Int. Cl.
*C12N 9/16* (2006.01)
*C12N 15/82* (2006.01)
*C12P 19/04* (2006.01)

(52) U.S. Cl.
CPC . *C12N 9/16* (2013.01); *C12N 15/82* (2013.01); *C12P 19/04* (2013.01)

(58) Field of Classification Search
None
See application file for complete search history.

(56) References Cited

PUBLICATIONS

Vander Kooi et al., Structural basis for the glucan phosphatase activity of starch Excess4, Proc. Natl. Acad. Sci. USA, 2010, 107, 15379-84.*
European Nucleotide Database, EMBL-EBI, Accession No. AAL27495, 2006, www.ebi.ac.uk.*
Kerk et al., A chloroplast-localized dual-specificity protein phosphatase in Arabidopsis contains a phylogenetically dispersed and ancient carbohydrate-binding domain, which binds the polysaccharide starch, Plant J., 2006, 46, 400-13.*
Sokolov, L. N., Dominguez-Solis, J. R., Allary, A. L., Buchanan, B. B., and Luan, S. (2006) Proc Natl Acad Sci U S A 103, 9732-9737.
Streb, S., and Zeeman, S.C. (2013). Starch metabolism in Arabidopsis. Arabidopsis Book 10, e0160.
Tagliabracci, V.S., Turnbull, J., Wang, W., Girard, J.M., Zhao, X., Skurat, A.V., Delgado-Escueta, A.V., Minassian, B.A., Depaoli-Roach, A.A., and Roach, P.J. (2007). Laforin is a glycogen phosphatase, deficiency of which leads to elevated phosphorylation of glycogen in vivo. Proc Natl Acad Sci U S A 104, 19262-19266.
Vander Kooi, C. W., Taylor, A. O., Pace, R. M., Meekins, D. A., Guo, H. F., Kim, Y., and Gentry, M. S. (2010) Structural basis for the glucan phosphatase activity of Starch Excess4. Proc Natl Acad Sci U S A 107, 15379-15384.
Worby, C.A., Gentry, M.S., and Dixon, J.E. (2006). Laforin, a dual specificity phosphatase that dephosphorylates complex carbohydrates. J Biol Chem 281, 30412-30418.
Yu, T.S., Kofler, H., Hausler, R.E., Hille, D., Flugge, U.I., Zeeman, S.C., Smith, A.M., Kossmann, J., Lloyd, J., Ritte, G., Steup, M., Lue, W.L., Chen, J., and Weber, A. (2001). The Arabidopsis sex1 mutant is defective in the R1 protein, a general regulator of starch degradation in plants, and not in the chloroplast hexose transporter. Plant Cell 13, 1907-1918.
Zeeman, S. C., Kossmann, J., and Smith, A. M. (2010) Annu Rev Plant Biol 61, 209-234.
Gentry, Matthew S. (2013). Glucan Phosphatases Link Neurodegeneration and Starch Metabolism. Iowa State.
Gentry, Matthew S. (2013). Structural mechanisms of starch dephosphorylation. Slovakia.
Gentry, Matthew S. (2012). Glucan Phosphatases Link Neurodegeneration and Starch Metabolism. Syracuse University.
Gentry, Matthew S. (2010). 100 years of research links plant starch to neurodegeneration. ALAMY-4.
Gentry, Matthew S. (2010). Lafora disease: 100 years of research links plan starch to neurodegeneration. Oslo.
Gentry, Matthew S. (2011). Lafora disease: 100 years of research links plant starch to neurodegeneration. Eastern Kentucky University.
Gentry, Matthew S. (2012). Glucan Phosphatases: the intersection of neurodegeneration & starch metabolism. Snowmass.
Gentry, Matthew S. (2013). From human neurodegenerative disease to biofuels. Bellarmine University.
Gentry, Matthew S. (2013). Glucan Phosphatases: the intersection of neurodegeneration & starch metabolism. Howard Hughes Medical Institute.
Gentry, Matthew S. (2014). Engineering Glucan Phosphatase Activity by Defining the STructural Basis of Starch Dephosphorylation.
Gentry, Matthew S. (2014). Glucan phosphatases: the intersection of neurodegeneration and starch metabolism.
Tagliabracci, V.S., Roach, P.J. (2010) Insights into the mechanism of polysaccharide dephosphorylation by a glucan phosphatase. Proc Natl Acad Sci 107, 15312-15313.
Sherwood, A.R., Dukhande, V.V., Gentry, M.S. (2012) Laforin: Function and Action of a Glucan Phosphatase. Encyclopedia of Signalling Molecules, 1003-1010.
Gentry, M.S., Roma-Mateo, C. Sanz, P. (2012) Laforin, a protein with many faces: glucan phosphatase, adapter protein, et alii. The FEBS Journal, 1-13.
Roma-Mateo, C., Sanz, P. Gentry, M.S. (2012) Deciphering the Role of Malin in the Lafora Progressive Myoclonus Epilepsy. IUBMB Life. 1-8.
Sherwood, A.R. (2013) Investigating Therapeutic Options for Lafora Disease Using Structural Biology and Translational Methods. Theses and Dissertations—Molecular and Cellular Biochemistry Paper 13.

(Continued)

*Primary Examiner* — Robert Mondesi
*Assistant Examiner* — Todd M Epstein
(74) *Attorney, Agent, or Firm* — Stites & Harbison PLLC; Mandy Wilson Decker

(57) ABSTRACT

Glucan phosphatase nucleotide or polypeptide variants of the presently-disclosed subject matter can alter the biophysical properties of starch in vitro or in planta, as well as the total starch biomass production in planta as compared to plants expressing wild-type glucan phosphatases. Plants producing the polypeptide variants of the presently-disclosed subject matter can have increased starch accumulation, increased starched biomass, and/or starch having desired biophysical properties. A method of the presently-disclosed subject matter for producing altered starch includes providing a plant that produces a glucan phosphatase polypeptide variant that comprises an amino acid mutation and collecting starch from the plant.

8 Claims, 23 Drawing Sheets

(56) References Cited

PUBLICATIONS

Sanchez-Martin, P., Raththagala, M., Bridges, T.M., Husodo, S., Gentry, M.S., Sanc, P. Roma-Mateo, C. (2013) Dimerization of the Glucan Phosphatase Laforin Requires the Participation of Cysteine 329. PLoS One 8, 1-11.

Sherwood, A.R., Johnson, M.B., Delgado-Escueta, A.V., Gentry, M.S. (2013) A bioassay for Lafora disease and laforin glucan phosphatase activity. Clin Biochem.

Hofmann, N.R. (2013) A New Mechanism for Starch Dephosphorylation: Insight from the Structure of Like Sex Four2. The Plant Cell 25.

Meekins, D.A., Guo, H., Husodo, S., Paasch, B.C., Bridges, T.M., Santelia, D., Kotting, O., Vander Kooi, C.W., Gentry, M.S. (2013) Structure of the Arabidopsis Glucan Phosphatase Like Sex Four2 Reveals a Unique Mechanism for Starch Dephosphorylation. The Plant Cell 25, 2302-2314.

Brewer, M.K., Husodo, S., Dukhande, V.V., Johnson, M.B., Gentry, M.S. (2014) Expression, purification and characterization of soluble red rooster laforin as a fusion protein in *Escherichia coli*. BMC Biochemstry 1-10.

Meekins, D.A., Raththagala, M., Husodo, S., White, C.J., Guo, h., Kotting, O., Vander Kooi, C.W., Gentry, M.S. (2014) Phosphoglucan-bound structure of starch phosphatase Starch Excess4reveals the mechanism for C6 specificity. Proc Natl Acad Sci Early Edition 1-6.

Ballicora, M. A., Frueauf, J. B., Fu, Y., Schurmann, P., and Preiss, J. (2000) J Biol Chem 275, 1315-1320.

Balmer, Y., Koller, A., Del Val, G., Manieri, W., Schurmann, P., and Buchanan, B. B. (2003) Proc Nati Acad Sci U S A 100, 370-375.

Balmer, Y., Vensel, W. H., Cai, N., Manieri, W., Schurmann, P., Hurkman, W. J., and Buchanan, B. B. (2006) Proc Natl Acad Sci U S A 103, 2988-2993.

Baunsgaard, L., Lutken, H., Mikkelsen, R., Glaring, M.A., Pham, T.T., and Blennow, A. (2005). A novel isoform of glucan, water dikinase phosphorylates pre-phosphorylated alpha-glucans and is involved in starch degradation in Arabidopsis. Plant J 41, 595-605.

Blennow A, B.-S.A., Bauer R. (2001). Amylopectin aggregation as a function of starch phosphate content studied by size exclusion chromatography and on-line refractive index and light scattering. International Journal of Biological Macromolecules 28, 409-420.

Blennow, A., and Engelsen, S.B. (2010). Helix-breaking news: fighting crystalline starch energy deposits in the cell. Trends Plant Sci 15, 236-240.

Blennow, A., Bay-Smidt, A. M., Leonhardt, P., Bandsholm, O., and Madsen, M. H. (2003) Starch—Stärke 55, 381-389.

Blennow, A., Bay-Smidt, A.M., Olsen, C.E., and Moller, B.L. (2000). The distribution of covalently bound phosphate in the starch granule in relation to starch crystallinity. Int J Biol Macromol 27, 211-218.

Blennow, A., Nielsen, T.H., Baunsgaard, L., Mikkelsen, R., and Engelsen, S.B. (2002). Starch phosphorylation: a new front line in starch research. Trends Plant Sci 7, 445-450.

Boraston, A.B., Bolam, D.N., Gilbert, H.J., and Davies, G.J. (2004). Carbohydrate-binding modules: fine-tuning polysaccharide recognition. Biochem J 382, 769-781.

Buleon, A., Colonna, P., Planchot, V., and Ball, S. (1998). Starch granules: structure and biosynthesis. Int J Biol Macromol 23, 85-112.

Cantarel, B.L., Coutinho, P.M., Rancurel, C., Bernard, T., Lombard, V., and Henrissat, B. (2009). The Carbohydrate-Active EnZymes database (CAZy): an expert resource for Glycogenomics. Nucleic Acids Res 37, D233-238.

Caspar, T., Lin, T.P., Kakefuda, G., Benbow, L., Preiss, J., and Somerville, C. (1991). Mutants of Arabidopsis with altered regulation of starch degradation. Plant Physiol 95, 1181-1188.

Chisti, Y. (2007) Biotechnol Adv 25, 294-306 Chisti, Y. (2007) Biotechnol Adv 25, 294-306.

Comparot-Moss, S., Kotting, O., Stettler, M., Edner, C., Graf, A., Weise, S. E., Streb, S., Lue, W. L., MacLean, D., Mahlow, S., Ritte, G., Steup, M., Chen, J., Zeeman, S. C., and Smith, A. M. (2010) Plant Physiol 152, 685-697.

Dukhande, V. V., Sherwood, A. R., and Gentry, M. S. (2010) Laforin-Nature Molecule Page. in Nature Molecule Pages.

Dukhande, V.V., Rogers, D.M., Roma-Mateo, C., Donderis, J., Marina, A., Taylor, A.O., Sanz, P., and Gentry, M.S. (2011). Laforin, a dual specificity phosphatase involved in Lafora disease, is present mainly as monomeric form with full phosphatase activity. PLoS One 6, e24040.

Edner, C., Li, J., Albrecht, T., Mahlow, S., Hejazi, M., Hussain, H., Kaplan, F., Guy, C., Smith, S.M., Steup, M., and Ritte, G. (2007). Glucan, water dikinase activity stimulates breakdown of starch granules by plastidial beta-amylases. Plant Physiol 145, 17-28.

Fettke, J., Hejazi, M., Smirnova, J., Hochel, E., Stage, M., and Steup, M. (2009) J Exp Bot 60, 2907-2922 Fettke, J., Hejazi, M., Smirnova, J., Hochel, E., Stage, M., and Steup, M. (2009) J Exp Bot 60, 2907-2922.

Fordham-Skelton, A. P., Chilley, P., Lumbreras, V., Reignoux, S., Fenton, T. R., Dahm, C. C., Pages, M., and Gatehouse, J. A. (2002) The Plant Journal 29, 705-715.

Fu, Y., Ballicora, M. A., Leykam, J. F., and Preiss, J. (1998) J Biol Chem 273, 25045-25052.

Ganesh, S., Tsurutani, N., Suzuki, T., Hoshii, Y., Ishihara, T., Delgado-Escueta, A.V., and Yamakawa, K. (2004). The carbohydrate-binding domain of Lafora disease protein targets Lafora polyglucosan bodies. Biochem Biophys Res Commun 313, 1101-1109.

Gentry, M. S., and Pace, R. M. (2009) BMC Evol Biol 9, 138.

Santelia, D., Kotting, O., Seung, D., Schubert, M., Thalmann, M., Bischof, S., Meekins, D.A., Lutz, A., Patron, N., Gentry, M.S., Allain, F.H., and Zeeman, S.C. (2011). The phosphoglucan phosphatase like sex Four2 dephosphorylates starch at the C3-position in Arabidopsis. Plant Cell 23, 4096-4111.

Gentry, M.S., Dixon, J.E., and Worby, C.A. (2009). Lafora disease: insights into neurodegeneration from plant metabolism. Trends Biochem Sci 34, 628-639.

Gentry, M.S., Dowen, R.H., 3rd, Worby, C.A., Mattoo, S., Ecker, J.R., and Dixon, J.E. (2007). The phosphatase laforin crosses evolutionary boundaries and links carbohydrate metabolism to neuronal disease. J Cell Biol 178, 477-488.

Hansen, P. I., Larsen, F. H., Motawia, S. M., Blennow, A., Spraul, M., Dvortsak, P., and Engelsen, S. B. (2008) Biopolymers 89, 1179-1193.

Hansen, P.I., Spraul, M., Dvortsak, P., Larsen, F.H., Blennow, A., Motawia, M.S., and Engelsen, S.B. (2009). Starch phosphorylation—maltosidic restrains upon 3'- and 6'-phosphorylation investigated by chemical synthesis, molecular dynamics and NMR spectroscopy. Biopolymers 91, 179-193.

Hejazi, M., Fettke, J., Kotting, O., Zeeman, S.C., and Steup, M. (2010). The Laforin-like dual-specificity phosphatase SEX4 from Arabidopsis hydrolyzes both C6- and C3-phosphate esters introduced by starch-related dikinases and thereby affects phase transition of alpha-glucans. Plant Physiol 152, 711-722.

Henrissat, B. (1991) Biochem J 280 ( Pt 2), 309-316.

Henrissat, B., and Bairoch, A. (1993) Biochem J 293 ( Pt 3), 781-788.

Hsu, S., Kim, Y., Li, S., Durrant, E. S., Pace, R. M., Woods, V. L., Jr., and Gentry, M. S. (2009) Structural Insights into Glucan Phosphatase Dynamics Using Amide Hydrogen—Deuterium Exchange Mass Spectrometry. Biochemistry 48, 9891-9902.

Keeling, P. L., and Myers, A. M. (2010) Annu Rev Food Sci Technol 1, 271-303.

Kerk, D., Conley, T. R., Rodriguez, F. A., Tran, H. T., Nimick, M., Muench, D. G., and Moorhead, G. B. (2006) Plant J 46, 400-413.

Kotting, O., Kossmann, J., Zeeman, S.C., and Lloyd, J.R. (2010). Regulation of starch metabolism: the age of enlightenment? Curr Opin Plant Biol 13, 321-329.

Kotting, O., Pusch, K., Tiessen, A., Geigenberger, P., Steup, M., and Ritte, G. (2005). Identification of a novel enzyme required for starch metabolism in Arabidopsis leaves. The phosphoglucan, water dikinase. Plant Physiol 137, 242-252.

Kotting, O., Santelia, D., Edner, C., Eicke, S., Marthaler, T., Gentry, M.S., Comparot-Moss, S., Chen, J., Smith, A.M., Steup, M., Ritte, G., and Zeeman, S.C. (2009). Starch-Excess4 is a laforin-like Phosphoglucan phosphatase required for starch degradation in Arabidopsis thaliana. Plant Cell 21, 334-346.

(56) References Cited

OTHER PUBLICATIONS

Mikkelsen, R., Mutenda, K. E., Mant, A., Schurmann, P., and Blennow, A. (2005) Proc Natl Acad Sci U S A 102, 1785-1790.

Minassian, B.A., Lee, J.R., Herbrick, J.A., Huizenga, J., Soder, S., Mungall, A.J., Dunham, I., Gardner, R., Fong, C.Y., Carpenter, S., Jardim, L., Satishchandra, P., Andermann, E., Snead, O.C., 3rd, Lopes-Cendes, I., Tsui, L.C., Delgado-Escueta, A.V., Rouleau, G.A., and Scherer, S.W. (1998). Mutations in a gene encoding a novel protein tyrosine phosphatase cause progressive myoclonus epilepsy. Nat Genet 20, 171-174.

Moorhead, G.B., De Wever, V., Templeton, G., and Kerk, D. (2009). Evolution of protein phosphatases in plants and animals. Biochem J 417, 401-409.

Niittyla, T., Comparot-Moss, S., Lue, W.L., Messerli, G., Trevisan, M., Seymour, M.D., Gatehouse, J.A., Villadsen, D., Smith, S.M., Chen, J., Zeeman, S.C., and Smith, A.M. (2006). Similar protein phosphatases control starch metabolism in plants and glycogen metabolism in mammals. J Biol Chem 281, 11815-11818.

Ral, J. P., Bowerman, A. F., Li, Z., Sirault, X., Furbank, R., Pritchard, J. R., Bloemsma, M., Cavanagh, C. R., Howitt, C. A., and Morell, M. K. (2012) Plant biotechnology journal.

Ritte, G., Heydenreich, M., Mahlow, S., Haebel, S., Kotting, O., and Steup, M. (2006). Phosphorylation of C6- and C3-positions of glucosyl residues in starch is catalysed by distinct dikinases. FEBS Lett 580, 4872-4876.

Ritte, G., Lloyd, J.R., Eckermann, N., Rottmann, A., Kossmann, J., and Steup, M. (2002). The starch-related R1 protein is an alpha-glucan, water dikinase. Proc Natl Acad Sci U S A 99, 7166-7171.

Roach, P.J. (2002). Glycogen and its metabolism. Curr Mol Med 2, 101-120.

Roma-Mateo, C., Solaz-Fuster, M. C., Gimeno-Alcaniz, J. V., Dukhande, V. V., Donderis, J., Marina, A., Criado, O., Koller, A., Rodriguez De Cordoba, S., Gentry, M. S., and Sanz, P. (2011) Biochemical Journal 439, 265-275.

Santelia, D., and Zeeman, S.C. (2010). Progress in Arabidopsis starch research and potential biotechnological applications. Curr Opin Biotechnol 22, 271-280.

Sherwood, A.R., Paasch, B.C., Worby, C.A., and Gentry, M.S. (2013). A malachite green-based assay to assess glucan phosphatase activity. Anal Biochem 435, 54-56.

Silver, D. M., Silva, L. P., Issakidis-Bourguet, E., Glaring, M. A., Schriemer, D. C., and Moorhead, G. B. (2012) FEBS J.

Raththagala, M., et al. (2015) Structural Mechanism of Laforin Function in Glycogen Dephosphorylation and Lafora Disease. Molecular Cell 57, 261-272.

\* cited by examiner

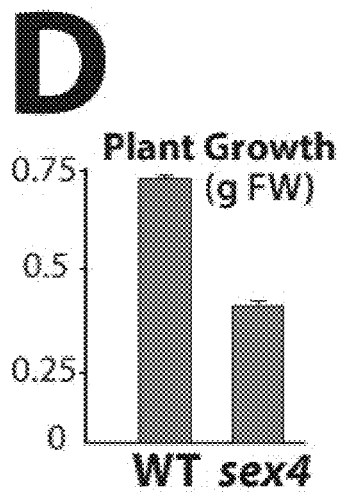
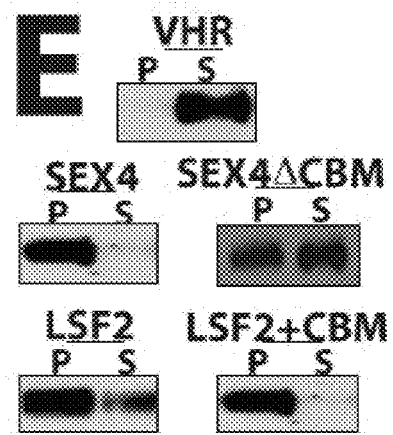
FIG. 5D  FIG. 5E
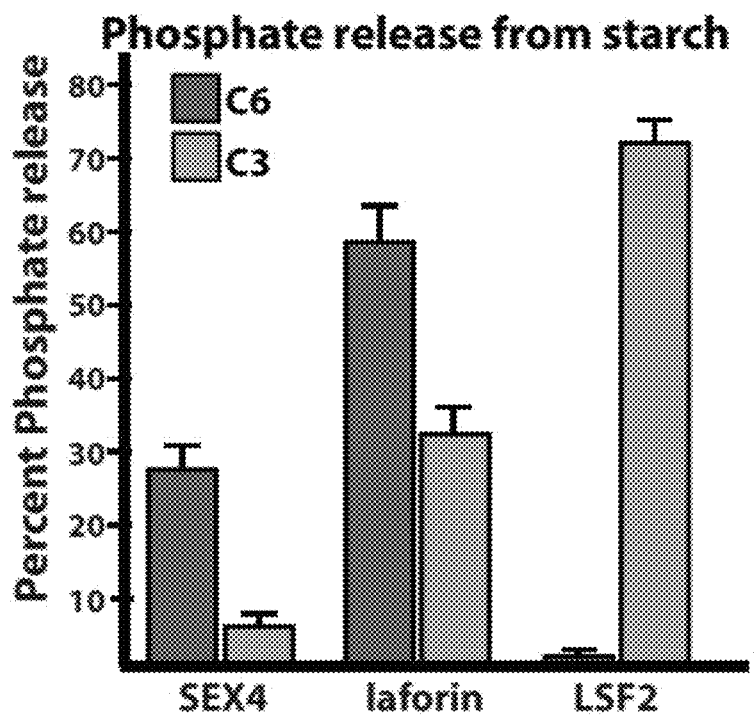
FIG. 6

SEQUENCE LISTING

<160> NUMBER OF SEQ ID NOS: 4

<210> SEQ ID NO 1
<211> LENGTH: 379
<212> TYPE: PRT
<213> ORGANISM: Arabidopsis thaliana

<400> SEQUENCE: 1

```
Met Asn Cys Leu Gln Asn Leu Pro Arg Cys Ser Val Ser Pro Leu Leu
1               5                   10                  15

Gly Phe Gly Cys Ile Gln Arg Asp His Ser Ser Ser Ser Ser Ser Leu
            20                  25                  30

Lys Met Leu Ile Ser Pro Pro Ile Lys Ala Asn Asp Pro Lys Ser Arg
        35                  40                  45

Leu Val Leu His Ala Val Ser Glu Ser Lys Ser Ser Ser Glu Met Arg
    50                  55                  60

Gly Val Ala Lys Asp Glu Glu Lys Ser Asp Glu Tyr Ser Gln Asp Met
65                  70                  75                  80

Thr Gln Ala Met Gly Ala Val Leu Thr Tyr Arg His Glu Leu Gly Met
                85                  90                  95

Asn Tyr Asn Phe Ile Arg Pro Asp Leu Ile Val Gly Ser Cys Leu Gln
            100                 105                 110

Thr Pro Glu Asp Val Asp Lys Leu Arg Lys Ile Gly Val Lys Thr Ile
        115                 120                 125

Phe Cys Leu Gln Gln Asp Pro Asp Leu Glu Tyr Phe Gly Val Asp Ile
    130                 135                 140

Ser Ser Ile Gln Ala Tyr Ala Lys Lys Tyr Ser Asp Ile Gln His Ile
145                 150                 155                 160

Arg Cys Glu Ile Arg Asp Phe Asp Ala Phe Asp Leu Arg Met Arg Leu
                165                 170                 175

Pro Ala Val Val Gly Thr Leu Tyr Lys Ala Val Lys Arg Asn Gly Gly
            180                 185                 190

Val Thr Tyr Val His Cys Thr Ala Gly Met Gly Arg Ala Pro Ala Val
        195                 200                 205

Ala Leu Thr Tyr Met Phe Trp Val Gln Gly Tyr Lys Leu Met Glu Ala
    210                 215                 220

His Lys Leu Leu Met Ser Lys Arg Ser Cys Phe Pro Lys Leu Asp Ala
225                 230                 235                 240

Ile Arg Asn Ala Thr Ile Asp Ile Leu Thr Gly Leu Lys Arg Lys Thr
                245                 250                 255

Val Thr Leu Thr Leu Lys Asp Lys Gly Phe Ser Arg Val Glu Ile Ser
            260                 265                 270

Gly Leu Asp Ile Gly Trp Gly Gln Arg Ile Pro Leu Thr Leu Gly Lys
        275                 280                 285

Gly Thr Gly Phe Trp Ile Leu Arg Glu Leu Pro Glu Gly Gln Phe
    290                 295                 300

Glu Tyr Lys Tyr Ile Ile Asp Gly Glu Trp Thr His Asn Glu Ala Glu
305                 310                 315                 320

Pro Phe Ile Gly Pro Asn Lys Asp Gly His Thr Asn Asn Tyr Ala Lys
                325                 330                 335

Val Val Asp Asp Pro Thr Ser Val Asp Gly Thr Thr Arg Glu Arg Leu
            340                 345                 350

Ser Ser Glu Asp Pro Glu Leu Leu Glu Glu Arg Ser Lys Leu Ile
        355                 360                 365
```

```
Gln Phe Leu Glu Thr Cys Ser Glu Ala Glu Val
    370                 375

<210> SEQ ID NO 2
<211> LENGTH: 282
<212> TYPE: PRT
<213> ORGANISM: Arabidopsis thaliana

<400> SEQUENCE: 2

Met Ser Val Ile Gly Ser Lys Ser Cys Ile Phe Ser Val Ala Arg Tyr
1               5                   10                  15

Thr Arg Glu Asn Glu Lys Ser Ser Cys Phe Thr Ser Ile Asn Lys Lys
            20                  25                  30

Ser Ser Leu Asp Leu Arg Phe Pro Arg Asn Leu Ala Gly Val Ser Cys
        35                  40                  45

Lys Phe Ser Gly Glu Asn Pro Gly Thr Asn Gly Val Ser Leu Ser Ser
    50                  55                  60

Lys Asn Lys Met Glu Asp Tyr Asn Thr Ala Met Lys Arg Leu Met Arg
65                  70                  75                  80

Ser Pro Tyr Glu Tyr His His Asp Leu Gly Met Asn Tyr Thr Leu Ile
                85                  90                  95

Arg Asp Glu Leu Ile Val Gly Ser Gln Pro Gln Lys Pro Glu Asp Ile
            100                 105                 110

Asp His Leu Lys Gln Glu Gln Asn Val Ala Tyr Ile Leu Asn Leu Gln
        115                 120                 125

Gln Asp Lys Asp Ile Glu Tyr Trp Gly Ile Asp Leu Asp Ser Ile Val
    130                 135                 140

Arg Arg Cys Lys Glu Leu Gly Ile Arg His Met Arg Arg Pro Ala Lys
145                 150                 155                 160

Asp Phe Asp Pro Leu Ser Leu Arg Ser Gln Leu Pro Lys Ala Val Ser
                165                 170                 175

Ser Leu Glu Trp Ala Val Ser Glu Gly Lys Gly Arg Val Tyr Val His
            180                 185                 190

Cys Ser Ala Gly Leu Gly Arg Ala Pro Gly Val Ser Ile Ala Tyr Met
        195                 200                 205

Tyr Trp Phe Cys Asp Met Asn Leu Asn Thr Ala Tyr Asp Thr Leu Val
    210                 215                 220

Ser Lys Arg Pro Cys Gly Pro Asn Lys Gly Ala Ile Arg Gly Ala Thr
225                 230                 235                 240

Tyr Asp Leu Ala Lys Asn Asp Pro Trp Lys Glu Pro Phe Glu Ser Leu
                245                 250                 255

Pro Glu Asn Ala Phe Glu Asp Ile Ala Asp Trp Glu Arg Lys Leu Ile
            260                 265                 270

Gln Glu Arg Val Arg Ala Leu Arg Gly Thr
    275                 280

<210> SEQ ID NO 3
<211> LENGTH: 294
<212> TYPE: PRT
<213> ORGANISM: Artificial Sequence
<220> FEATURE:
<223> OTHER INFORMATION: truncated and modified SEX4 from Arabidopsis

<400> SEQUENCE: 3

Gly Ser His Met Tyr Arg His Glu Leu Gly Met Asn Tyr Asn Phe Ile
1               5                   10                  15

Arg Pro Asp Leu Ile Val Gly Ser Cys Leu Gln Thr Pro Glu Asp Val
```

```
            20                  25                  30
Asp Lys Leu Arg Lys Ile Gly Val Lys Thr Ile Phe Cys Leu Gln Gln
            35                  40                  45

Asp Pro Asp Leu Glu Tyr Phe Gly Val Asp Ile Ser Ser Ile Gln Ala
        50                  55                  60

Tyr Ala Lys Lys Tyr Ser Asp Ile Gln His Ile Arg Cys Glu Ile Arg
65                  70                  75                  80

Asp Phe Asp Ala Phe Asp Leu Arg Met Arg Leu Pro Ala Val Val Gly
                85                  90                  95

Thr Leu Tyr Lys Ala Val Lys Arg Asn Gly Val Thr Tyr Val His
            100                 105                 110

Cys Thr Ala Gly Met Gly Arg Ala Pro Ala Val Ala Leu Thr Tyr Met
            115                 120                 125

Phe Trp Val Gln Gly Tyr Lys Leu Met Glu Ala His Lys Leu Leu Met
        130                 135                 140

Ser Lys Arg Ser Cys Phe Pro Lys Leu Asp Ala Ile Arg Asn Ala Thr
145                 150                 155                 160

Ile Asp Ile Leu Thr Gly Leu Lys Arg Lys Thr Val Thr Leu Thr Leu
                165                 170                 175

Lys Asp Lys Gly Phe Ser Arg Val Glu Ile Ser Gly Leu Asp Ile Gly
            180                 185                 190

Trp Gly Gln Arg Ile Pro Leu Thr Leu Gly Lys Gly Thr Gly Phe Trp
        195                 200                 205

Ile Leu Lys Arg Glu Leu Pro Glu Gly Gln Phe Glu Tyr Lys Tyr Ile
    210                 215                 220

Ile Asp Gly Glu Trp Thr His Asn Glu Ala Glu Pro Phe Ile Gly Pro
225                 230                 235                 240

Asn Lys Asp Gly His Thr Asn Asn Tyr Ala Lys Val Val Asp Asp Pro
                245                 250                 255

Thr Ser Val Asp Gly Thr Thr Arg Glu Arg Leu Ser Ser Glu Asp Pro
            260                 265                 270

Glu Leu Leu Glu Glu Glu Arg Ser Lys Leu Ile Gln Phe Leu Glu Thr
        275                 280                 285

Cys Ser Glu Ala Glu Val
        290

<210> SEQ ID NO 4
<211> LENGTH: 208
<212> TYPE: PRT
<213> ORGANISM: Artificial Sequence
<220> FEATURE:
<223> OTHER INFORMATION: truncated and modified LSF2 polypeptid sequence

<400> SEQUENCE: 4

Gly Ser His Met Met Arg Ser Pro Tyr Glu Tyr His His Asp Leu Gly
1               5                   10                  15

Met Asn Tyr Thr Leu Ile Arg Asp Glu Leu Ile Val Gly Ser Gln Pro
            20                  25                  30

Gln Lys Pro Glu Asp Ile Asp His Leu Lys Gln Glu Gln Asn Val Ala
        35                  40                  45

Tyr Ile Leu Asn Leu Gln Gln Asp Lys Asp Ile Glu Tyr Trp Gly Ile
    50                  55                  60

Asp Leu Asp Ser Ile Val Arg Arg Cys Lys Glu Leu Gly Ile Arg His
65                  70                  75                  80

Met Arg Arg Pro Ala Lys Asp Phe Asp Pro Leu Ser Leu Arg Ser Gln
```

```
                    85                      90                      95
Leu Pro Lys Ala Val Ser Ser Leu Glu Trp Ala Val Ser Glu Gly Lys
            100                     105                     110

Gly Arg Val Tyr Val His Cys Ser Ala Gly Leu Gly Arg Ala Pro Gly
            115                     120                     125

Val Ser Ile Ala Tyr Met Tyr Trp Phe Cys Asp Met Asn Leu Asn Thr
            130                     135                     140

Ala Tyr Asp Thr Leu Val Ser Lys Arg Pro Cys Gly Pro Asn Lys Gly
145                     150                     155                     160

Ala Ile Arg Gly Ala Thr Tyr Asp Leu Ala Lys Asn Asp Pro Trp Lys
                165                     170                     175

Glu Pro Phe Glu Ser Leu Pro Glu Asn Ala Phe Glu Asp Ile Ala Asp
                180                     185                     190

Trp Glu Arg Lys Leu Ile Gln Glu Arg Val Arg Ala Leu Arg Gly Thr
                195                     200                     205
```

GLUCAN PHOSPHATASE VARIANTS FOR STARCH PHOSPHORYLATION

CROSS REFERENCE TO RELATED APPLICATION

The present application claims the benefit of U.S. Provisional Application No. 61/673,476, filed Jul. 19, 2012, herein incorporated by reference.

GOVERNMENT INTEREST

Subject matter described herein was made with government support under Grant Numbers K99/R00 NS061803, P20 RR020171, and R01 NS070899 awarded by the National Institutes of Health (NIH). The government has certain rights in the described subject matter.

TECHNICAL FIELD

The presently-disclosed subject matter relates to glucan phosphatase polypeptide variants, and in particular, Starch Excess 4 (SEX4) glucan phosphatase polypeptides and Like Sex Four 2 (LSF2) glucan phosphatase polypeptides having at least one amino acid mutation. Embodiments of the presently-disclosed subject matter also relate to methods of utilizing glucan phophatase polypeptide variants to alter starch metabolism and structure.

INTRODUCTION

Starch plays a central role in many aspects of daily life: it is a major food source, it is key to biofuels, and it is an industrial feedstock, and increasing demand for starch has led to competition for it among these industries. Starch from the seeds of cereal crops and the tubers of potatoes and cassava accounts for 50-80% of daily caloric intake (Copeland (2009), Keeling (2010)). In the U.S., >20% of corn starch is converted into ethanol for use as a renewable biofuel, and starch also plays a central role in the production of molecular hydrogen by some micro algae and in algal oil production (see e.g. USDA (2010)). Microalgal oil production is increased by supplying starch to the microalgae so that they grow mixotrophically (i.e. utilizing carbon from starch and photosynthesis) rather than autotrophically (Malcata (2011), Bhatnagar (2011), Chen (2011)). Starch is also a cheap and renewable industrial feedstock for producing paper, textiles, adhesives, plastics, and pharmaceuticals (Delcour (2011), Santelia (2011)).

Given the high demand for starch, there has been a demand for developing "designer starches" that possess novel biophysical properties and functionalities to improve nutrition, increase energy supplies, and provide safer and cheaper industrial feedstocks (Santelia (2011, Jobling (2004), Morell (2005)). However, known chemicals that modify the biophysical properties of native starch for industrial applications are hazardous (Jobling (2004), Morell (2005), Tester (2000), Tharanathan (2005)). On the other hand, starch phosphorylation remains the only known natural starch modification and can affect many of starch's biophysical properties, including viscosity, paste stickiness, and starch granule fragility (Santelia (2011), Jobling (2004), Blennow (2003), Blennow (2000)).

Starch is comprised of the glucose polymer amylose, which is a linear molecule comprised of glucose moieties linked together by α-1,4-glycosidic bonds with very few branches, and amylopectin, which is comprised of glucose linked together by α-1,4-glycosidic bonds with α-1,6-glycosidic branches occurring every 12-25 glucose moieties. The branches in amylopectin, the major component in starch, are arranged in clusters at regular intervals. Adjacent chains within the clusters form double helices and the clusters organize into crystalline lamellae that make starch water-insoluble. The structures of amylopectin (1) and amylase (2) are shown below.

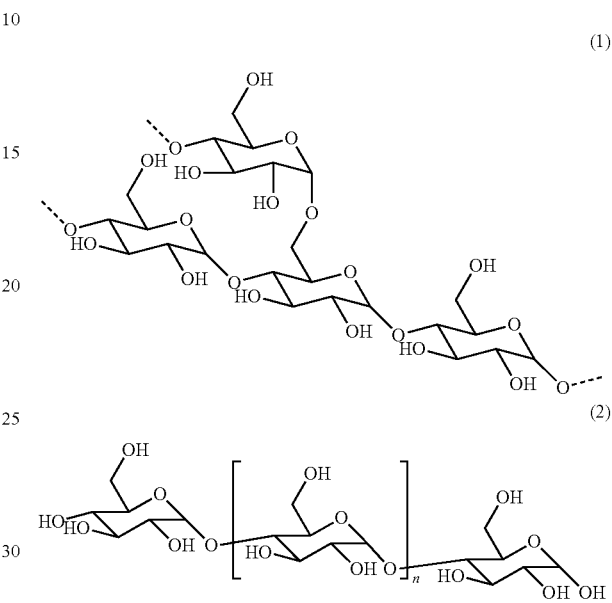

Starch degradation via hydrolysis is catalyzed by isoamylase, α-amylase, and β-amylases (BAMs) and involves reversible starch phosphorylation and dephosphorylation (34-37). Starch is phosphorylated by glucan water dikinase (GWD), which phosphorylates the C6 position of glucose moieties and triggers C3 phosphorylation by phosphoglucan water dikinase (PWD) (Ritte (2006), Ritte (2002) Kotting (2005), Baunsgaard (2005)). Without being bound by theory or mechanism, it is believed that C3 phosphorylation imposes steric effects inducing a conformational change in the outer glucans of starch making them water-soluble and accessible to BAMs and isoamylase (Hansen (2008), Hansen (2009), Kozlov (2007), Sanderson (2006)). However, glucan phosphatase activity is required for BAMs to completely degrade the glucan chains (Kotting (2009)).

Glucan phosphatases are members of the protein tyrosine phosphatase (PTP) superfamily characterized by a conserved Cx5R catalytic motif (Yuvaniyama (1996), Gentry (2007)). The PTPs include a heterogeneous group of phosphatases called the Dual Specificity Phosphatases (DSPs) that dephosphorylate phospho-Ser, -Thr, and -Tyr of proteinaceous substrates as well as more diverse substrates such as lipids, nucleic acids, and glucans (Alonso (2003), Tonks (2006), Moorhead (2009)).

Starch EXcess 4 (SEX4) is one type of glucan phosphatase. SEX4 contains a chloroplast Targeting Peptide (cTP), a Dual Specificity Phosphate (DSP) domain, a Carbohydrate Binding Molecule (CBM), and a carboxy-terminal (CT) domain that cradles the DSP and CBM. SEX4 works in synergy with glucan hydrolases to catabolize starch (Kotting (2009)). While the role of SEX4 in starch metabolism is still being defined, deletion of SEX4 results in excess starch and a severe decrease in total biomass (Santelia (2011), Kotting (2009), Niittyla (2006)). Manipulation of this system holds intriguing promise with respect to increasing starch yields, but will require engineering rather than gene deletion.

An additional concern is that starch processing requires hazardous chemicals in order to modify it for industrial application. Starch-based feedstocks are generated by an approach utilizing harsh chemical (acid and base treatment) and physical (>100° C.) extremes combined with large quantities of amylase enzymes to degrade or modify native starch for industrial applications. Innovative strategies are needed to both increase starch production and to provide safer and cheaper starch-based feedstocks. Thus, there remains a need for a natural starch modification that can alter starch metabolism without the use of hazardous chemicals. Glucan phosphatases are one area of interest, since they generally function to catabolize starch. However, deletion of glucan phosphatases, such as SEX4, results in excess starch synthesis and starch biomass reduction so that overall starch production is not efficiency increased. Hence, glucan phosphatase polypeptide variants that produce "designer starches" possessing novel biophysical properties and altered starch biomass are highly desired.

The glucan phosphatase Starch EXcess 4 (SEX4) has been shown to preferentially dephosphorylate the C6-position and Like Sex Four 2 (LSF2) specifically dephosphorylates the C3-position of glucose moieties (Hejazi (2010), Santelia (2011)). However, the structural basis for specific glucan phosphatase activity and position specificity has not been determined. LSF2 and SEX4 are DSPs that are conserved in Archaeplastida/Plantae genomes from land plants to single-cell green algae (Gentry (2007), Gentry and Pace (2009), Santelia (2011)). Arabidopsis lacking SEX4 activity have larger starch granules, higher level of leaf starch, and altered patterns of starch phosphorylation, a phenotype further exacerbated upon the simultaneous loss of LSF2 activity (Zeeman (2002), Niittyla (2006), Kotting (2009), Santelia (2011)). Furthermore, LSF2 and SEX4 are functional homologs to the glycogen phosphatase laforin that is found in all vertebrates and a subset of unicellular protozoa (Worby (2006), Gentry (2007), Tagliabracci (2007), Gentry (2009)). Mutations in the gene that encodes laforin in humans cause the accumulation of insoluble carbohydrates leading to the fatal epileptic disorder Lafora's disease (Minassian (1998), Serratosa (1999), Gentry (2009)). These findings demonstrate that glucan phosphatase activity is highly conserved in nature and essential for both starch and glycogen metabolism. SEX4 and LSF2 proteins both contain a chloroplast Targeting Peptide (cTP), a DSP domain, and a unique C-Terminal (CT) motif (Niittyla (2006), Sokolov (2006), Gentry (2007), Kotting (2009), Vander Kooi (2010), Santelia (2011)).

Chloroplast targeting peptides localize proteins to the chloroplast, the site of starch metabolism. The CT motif was originally identified in the SEX4 structure as a motif that folds into the DSP core and is essential for protein stability and function (Vander Kooi (2010)). Additionally, SEX4 contains a Carbohydrate Binding Module (CBM) that is common in starch-interacting enzymes, while LSF2 lacks a CBM (Niittyla (2006), Sokolov (2006), Gentry (2007)). CBMs are non-enzymatic domains that typically bind a specific carbohydrate and allow the catalytic portion of the enzyme to modify the substrate (Coutinho and Henrissat (1999), Boraston (2004), Machovic and Janecek (2006)). The previously determined glucan-free SEX4 structure (PDB: 3NME) demonstrated that its CBM and DSP domains interact to form a continuous binding pocket that coordinates the dual functions of glucan binding and dephosphorylation (Vander Kooi (2010)). An additional plant protein called Like Sex Four 1 (LSF1) also contains a CBM and DSP domain (Comparot-Moss (2010)). While LSF1 is required for starch degradation, it lacks phosphatase activity and is not considered a glucan phosphatase (Comparot-Moss (2010)). Conversely, LSF2 binds and dephosphorylates glucans, but it is notable that this glucan phosphatase lacks a CBM (Santelia (2011)). Indeed, the glucan phosphatase family was first defined as any protein containing both a DSP and CBM (Gentry (2007)). Thus, the physical basis for LSF2-starch interaction and dephosphorylation is unclear, although it has been previously suggested that LSF2 may use a scaffold protein or an unidentified glucan-binding interface to maintain interactions with starch (Comparot-Moss (2010, Santelia 2011)).

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes glucan phosphatase polypeptide variants. In some embodiments the glucan phosphatase polypeptide variant is a Starch EXcess 4 (SEX4) glucan phosphatase polypeptide variant or a Like Sex Four2 (LSF2) glucan phosphatase polypeptide variant. In some embodiments the glucan phosphatase polypeptide variant comprises an amino acid mutation in the Dual Specificity Phosphatase (DSP) domain of the glucan phosphatase polypeptide variant. The presently-disclosed subject matter further includes nucleotides sequences, including isolated cDNA molecules, that encode glucan phosphatases polypeptide as disclosed herein.

In some embodiments the glucan phosphatase polypeptide variants comprise a wild type amino acid sequence corresponding to SEQ ID NO: 1 comprising a mutation or combination of mutations selected from the group consisting of Y139A, F167A, M204A, F235A, K237R, K237N, K237S, W278A, K307A, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A.

In some embodiments, the glucan phosphatase polypeptide variant can additionally include up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 additional amino acid substitutions relative to SEQ ID NO: 1. In some embodiments, the additional amino acid substitutions are conservative amino acid substitutions. In some embodiments, the additional amino acid substitutions do not substantially alter function of the polypeptide. In some embodiments, the additional amino acid substitutions are not located in a Dual Specificity Phosphatase (DSP) domain of the glucan phosphatase polypeptide.

In some embodiments, the glucan phosphatase polypeptide variant can comprise a wild type amino acid sequence corresponding to a fragment of SEQ ID NO: 1 comprising a mutation or combination of mutations selected from the group consisting of Y139A, F167A, M204A, F235A, K237R, K237N, K237S, W278A, K307A, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A. The fragment of SEQ ID NO: 1 can include up to about 1, 2, 3, 4, 5, 6, 7, 8, 9, or 10 amino acid deletions from the N-terminus or up to about 1, 2, 3, 4, 5, 6, 7, 8, 9, 10, 11, 12, 13, 14, 15, 16, 17, 18, 19, or 20 amino acid deletions from the C-terminus. Fragments are typically at least about 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, or 378 amino acids long.

In some embodiments the glucan phosphatase polypeptide variants comprise a wild type amino acid sequence corresponding to SEQ ID NO: 2 comprising a mutation or combination of mutations selected from the group consisting of S194A, S194K, S194T, S194N, S194Q, A195G, A195M, A195D, A195H, A195E, L197M, Q129A, D130A, K131A, D163A, D161A, D132A, K160A, G198A, G230A, K233A, N232A, Y135A, Y85A, Y83A, W136A, W136A/F162A, W136M, F162Y, F162M, F162A, F162T, F162N, R153A, M155A, R156A, R157A, S177A, S177R, S177Q, S177Y, W180A, W180A/F261A, LSF2-C-terminalRGT, K250A, E251A, N159A, F261A, D263A, W267A, E268A, LSF2+sex4CBM, G230F, G230F/N232K, N232K, G230Y, G230Y/N232D, N232D, W136F, W136N, and K245A.

In some embodiments, the glucan phosphatase polypeptide variant can additionally include up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 additional amino acid substitutions relative to SEQ ID NO: 2. In some embodiments, the additional amino acid substitutions are conservative amino acid substitutions. In some embodiments, the additional amino acid substitutions do not substantially alter function of the polypeptide. In some embodiments, the additional amino acid substitutions are not located in a Dual Specificity Phosphatase (DSP) domain of the glucan phosphatase polypeptide.

In some embodiments, the glucan phosphatase polypeptide variant can comprise a wild type amino acid sequence corresponding to a fragment of SEQ ID NO: 2 comprising a mutation or combination of mutations selected from the group consisting of S194A, S194K, S194T, S194N, S194Q, A195G, A195M, A195D, A195H, A195E, L197M, Q129A, D130A, K131A, D163A, D161A, D132A, K160A, G198A, G230A, K233A, N232A, Y135A, Y85A, Y83A, W136A, W136A/F162A, W136M, F162Y, F162M, F162A, F162T, F162N, R153A, M155A, R156A, R157A, S177A, S177R, S177Q, S177Y, W180A, W180A/F261A, LSF2-C-terminalRGT, K250A, E251A, N159A, F261A, D263A, W267A, E268A, LSF2+sex4CBM, G230F, G230F/N232K, N232K, G230Y, G230Y/N232D, N232D, W136F, W136N, and K245A. The fragment of SEQ ID NO: 2 can include up to about 1, 2, 3, 4, 5, 6, 7, 8, 9, or 10 amino acid deletions from the N-terminus or up to about 1, 2, 3, 4, 5, 6, 7, 8, 9, 10, 11, 12, 13, 14, 15, 16, 17, 18, 19, or 20 amino acid deletions from the C-terminus. Fragments are typically at least about 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, or 281 amino acids long.

The presently-disclosed subject matter further includes a composition comprising starch, wherein the starch is from a plant expressing a glucan phosphatase polypeptide having an amino acid mutation (glucan phosphatase polypeptide variant).

The presently-disclosed subject matter further includes a method of producing starch, which comprises providing a plant that comprises a glucan phosphatase polypeptide variant and collecting starch from the plant. In some embodiments the glucan phosphatase variant can alter the biophysical properties and/or the total biomass of the starch that is collected. In some embodiments the glucan phosphatase variant has more or less specific glucan phosphatase activity than a wild type glucan phosphatase. In some embodiments, plants that comprise the glucan phosphatase variant produce more starch biomass than plants having the wild type glucan phosphatase.

BRIEF DESCRIPTION OF THE SEQUENCE LISTING

SEQ ID NO: 1 is an amino acid sequence encoding a wild type *Arabidopsis* Starch Excess 4 (SEX4) glucan phosphate polypeptide;

SEQ ID NO: 2 is an amino acid sequence encoding a wild type *Arabidopsis* Like Sex Four2 (LSF2) glucan phosphate polypeptide;

SEQ ID NO: 3 is an truncated portion of the polypeptide of SEQ ID NO: 1 that includes four additional terminal amino acids and that was subjected to crystallization; and SEQ ID NO: 4 is an truncated portion of the polypeptide of SEQ ID NO: 2 that includes four additional terminal amino acids and that was subjected to crystallization.

BRIEF DESCRIPTION OF THE DRAWINGS

FIG. 5D shows plant biomass in WT and sex4−/− plants.

FIG. 5E shows results of a glucan binding assay (proteins bound to glucans (P); proteins not bound to glucan (S)).

FIG. 6 is a graph showing release of phosphate from starch at C6 or C3 by SEX4, laforin, and LSF2, in accordance with the present invention.

FIG. 7A shows DXMS results of ligand-free SEX4.

FIG. 7B shows percent change in deuteration of ligand-free vs. glucan bound.

FIG. 7C shows SEX4 structure overlaid with DXMS results.

FIG. 7D shows 180° rotation of SEX4 structure with overlay.

FIG. 7E shows models of SEX4 dynamics upon glucan binding (white star indicates the position of the active site).

FIG. 9A-9E shows the structure of LSF2 bound to maltohexaose and phosphate, wherein FIG. 9A is a ribbon diagram of LSF2 (residues 79-282). Maltohexaose chains (green, cyan, orange, pink) and phosphate (teal) are shown. Elements of secondary structure are numbered consecutively from N- to C-termini. FIG. 9B shows a maltohexaose chain (green) and phosphate (teal) at the active site (red) channel. Image correlates with the red box in FIG. 9A. Glucose moieties are numbered from non-reducing to reducing end. The total contact area of the active site channel with phosphate and maltohexaose is 511 Å$^2$. FIG. 9C is a graph showing specific activity of LSF2 WT and inactive mutant LSF2 C193S (C/S) against the C6- and C3-position of $Arabidopsis$ starch. Phosphate-free starch was purified from gwd-deficient $Arabidopsis$ (Yu (2001)) the starch was pre-labeled with $^{33}$P at either the C6- or C3-position, and then incubated with recombinant protein. Starch dephosphorylation over time was linear and was measured via release of $^{33}$P. The reaction time was 5 minutes. Each bar is the mean±standard deviation of 6 replicates. FIG. 9D is a 2Fo-Fc omit density map of maltohexaose chain (green) and phosphate (teal) at the active site (σ 1.35). The O3 group of Glc3 is highlighted. FIG. 9E is a LSF2 active site catalytic triad (yellow) residues interact with maltohexaose and phosphate. S(C)193 (catalytically inactive mutant, C193S) and R199 are located within the PTP loop between β5 and α6 and D161 is located within the D-loop between β4 and α5.

FIGS. 13A and 13B relate to the LSF2 aromatic Channel wherein FIG. 13A shows a maltohexaose chain (green) interacts with aromatic channel residues at the LSF2 active site. Y83 and Y85 are located in the recognition domain amino-terminal from α1. Y135 and W136 are located in the V-loop in α3. F162 is located in the D-loop between β4 and α5. The total contact area of the aromatic channel residues with maltohexaose is 266 Å$^2$. FIG. 13B depicts the specific activity of aromatic channel mutants against the C3-position of $Arabidopsis$ starch granules. Phosphate-free starch from gwd-deficient plants (Yu (2001)) was purified and pre-labeled at the C3- or C6-position with $^{33}$P as in FIG. 13C. The labeled starch was then incubated with LSF2 WT or LSF2 aromatic channel mutants and starch dephosphorylation was measured via release of $^{33}$P. The reaction time was 5 minutes. Each bar is the mean±standard deviation of 6 replicates. Mutated residues are marked with an asterisk in FIG. 20.

FIG. 17A shows results from co-sedimentation assay of protein and amylopectin (amylopectin binding assay). Recombinant histidine-tagged proteins were incubated with 5 mg/ml amylopectin, amylopectin was pelleted by ultracentrifugation, proteins in the pellet (P) and supernatant (S) were separated by SDS-PAGE, and visualized by Western analysis. Amylopectin-bound proteins are found in the pellet (P) and unbound proteins are found in the supernatant (S).

FIG. 18A-19C show LSF2 glucan binding Site-2, wherein FIG. 18A is a transparent surface model of LSF2 Site-2 showing DSP domain (blue) and CT-motif (green) interaction with the maltohexaose chain (cyan). R153 and M155 are located on β4. R157 is located between β4 and α5. W180 is located on α5. T282 is located on the carboxy-terminus after α11. Glucose moieties are numbered from non-reducing to reducing end. The total contact area of Site-2 with maltohexaose is 391 Å$^2$. FIG. 18B shows specific activity of Site-2 mutants against the C3-position of *Arabidopsis* starch granules. Phosphate-free starch from gwd-deficient plants (Yu (2001)) was purified and pre-labeled at the C3- or C6-position with $^{33}$P as in FIG. 13B. The labeled starch was then incubated with LSF2 WT or LSF2 Site-2 mutants and starch dephosphorylation was measured via release of $^{33}$P. In addition to single point mutants, starch dephosphorylation was also determined for LSF2 lacking the carboxy-terminal residues R280, G281, and T282 (ΔRGT). The reaction time was 5 minutes. Each bar is the mean±standard error or standard deviation of 6 replicates. Mutated residues are marked with a circle in FIG. 20.

FIG. 19A-20C show LSF2 glucan binding Site-3, wherein FIG. 19A is a transparent surface model of LSF2 at the CT-motif loop (green) showing specific interactions with maltohexaose chains Hex-1 (orange) and Hex-2 (pink). K245 is located between α8 and α9. F261 is located between α10 and α11. E268 is located in α11. The total contact are of Site-3 with the maltohexaose chains is 338 Å$^2$. FIG. 19C is an amylopectin binding assay of Site-3 mutant F261A, Site-2/Site-3 mutant (R157A/F261A) and quadruple mutation of active site, Site-2 and Site-3 (F162A/W136A/R157A/F261A) was performed in a similar manner as described in FIG. 17A. Amylopectin-bound protein is found in the pellet (P) and unbound protein is found in the supernatant (S).

FIG. 20 relates to sequence conservation of LSF2 and SEX4. *Arabidopsis thaliana*—78-LSF2 sequence alignment with *Arabidopsis thaliana*—81-SEX4. Secondary structure of LSF2 and SEX4 is depicted above the primary sequences (α-helices=ellipses, β-sheets=boxes). DSP domain (blue), SEX4 CBM domain (orange), and CT motif (green) are labeled. Residues involved in LSF2 glucan binding are highlighted within the aromatic channel (asterisk), Site 2 (circle) and Site 3 (triangle). Residues in the aromatic channel are conserved between LSF2 and SEX4, however residues in Site 2 and Site 3 are not.

DESCRIPTION OF EXEMPLARY EMBODIMENTS

Figure 1:
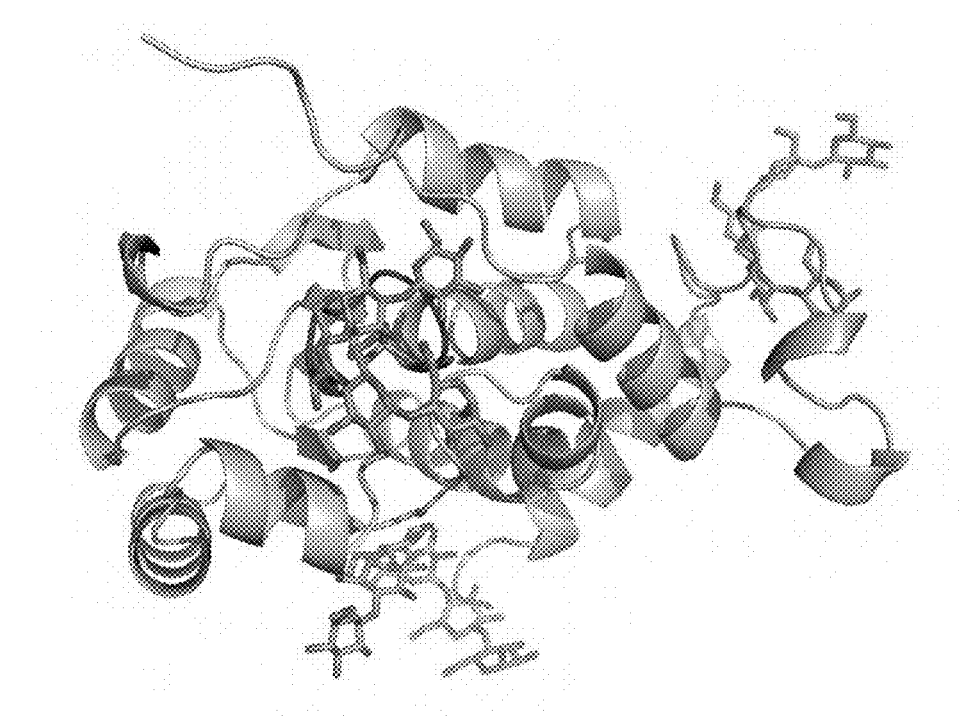
FIG. 1 is a crystal structure of *Arabidopsis* LSF2 with bound maltohextaose (PDB: 4KYR).
Figure 2:
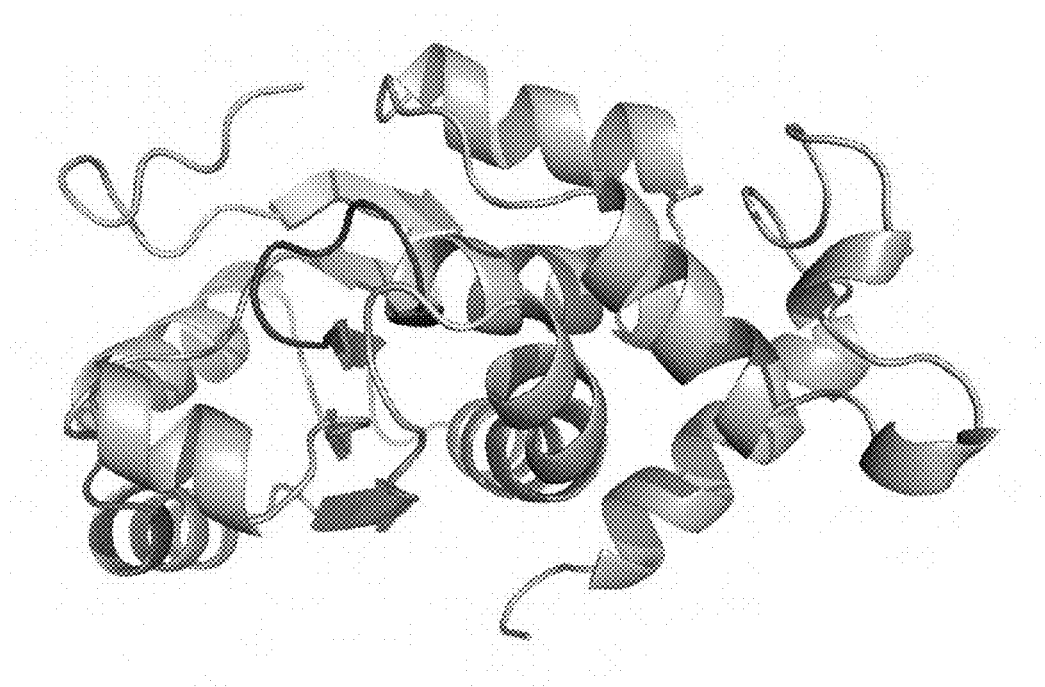
FIG. 2 is a crystal structure of *Arabidopsis* LSF2 without bound maltohextaose (PDB: 4KYQ).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes glucan phosphatase polypeptide variants. The glucan phosphatase polypeptide variants disclosed herein can alter the biophysical properties of starch and/or total biomass starch production. For example, some embodiments of glucan phosphatase polypeptide variants can increase total biomass starch production in planta. The presently-disclosed subject matter further relates to a composition comprising starch, wherein the starch is from a plant expressing a glucan phosphatase variant having an amino acid mutation. Still further, the presently-disclosed subject matter includes a method of producing starch, which comprises providing a plant that comprises a glucan phosphatase polypeptide variant, as disclosed herein comprising an amino acid mutation and collecting starch from the plant. Altering the biophysical properties or biomass production of starch can meet long felt but unmet needs that are being experienced in industries that use or produce starch.

In some embodiments, the glucan phosphatase polypeptide variant is a variant of a Starch Excess (SEX4) glucan phosphatase or a Like Sex Four2 (LSF2) glucan phosphatase. In some embodiments the glucan phosphatase polypeptide variant comprises a mutation, and the mutation can be in the DSP domain of the glucan phosphatase polypeptide variant.

In still further embodiments the glucan phosphatase polypeptide variant is selected from a glucan phosphatase polypeptide variant set forth in Table 1. Table 1 includes the amino acid mutations for a wild type glucan phosphatase polypeptide that has the amino acid sequence associated with SEQ ID NO: 1. Embodiments of the presently-disclosed subject matter also comprise any combination and variation of mutations in Table 1.

TABLE 1

Amino Acid Mutations Associated with SEQ ID NO:1

| Single Mutant | | | | Double Mutant | Triple Mutant |
|---|---|---|---|---|---|
| Y139A | W278A | T201S | G205S | Y139A/F167A | Y139A/F167A/F235A |
| F167A | K307A | A202T | F235G | W278A/W314A | W278A/W314A/F167A |

TABLE 1-continued

Amino Acid Mutations Associated with SEQ ID NO:1

| Single Mutant | | | Double Mutant | Triple Mutant |
|---|---|---|---|---|
| M204A | W314A | M204T | W278A/F167A | N326A/N332A/K307A |
| F235A | N326A | M204A | N326A/N332A | |
| K237R | D328A | M204R | N332A/K307A | |
| K237N | N332A | M204L | A202T/G205D | |
| K237S | T201K | G205D | F235G/K237N | |

In some embodiments, the glucan phosphatase polypeptide variant can additionally include up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 additional amino acid substitutions relative to SEQ ID NO: 1. In some embodiments, the additional amino acid substitutions are conservative amino acid substitutions. In some embodiments, the additional amino acid substitutions do not substantially alter function of the polypeptide. In some embodiments, the additional amino acid substitutions are not located in a Dual Specificity Phosphatase (DSP) domain of the glucan phosphatase polypeptide.

In some embodiments, the glucan phosphatase polypeptide variant can comprise a wild type amino acid sequence corresponding to a fragment of SEQ ID NO: 1 comprising a mutation or combination of mutations selected from the group consisting of Y139A, F167A, M204A, F235A, K237R, K237N, K237S, W278A, K307A, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A. The fragment of SEQ ID NO: 1 can include up to about 1, 2, 3, 4, 5, 6, 7, 8, 9, or 10 amino acid deletions from the N-terminus or up to about 1, 2, 3, 4, 5, 6, 7, 8, 9, 10, 11, 12, 13, 14, 15, 16, 17, 18, 19, or 20 amino acid deletions from the C-terminus. Fragments are typically at least about 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, or 378 amino acids long.

In some embodiments, the glucan phosphatase polypeptide variant comprises a sequence having at least 85, 86, 87, 88, 89, 90, 91, 92, 93, 94, 95, 96, 97, 98, or 99% homology to a polypeptide having the sequence of SEQ ID NO: 1 comprising at least one amino acid mutations selected from the group consisting of Y139A, F167A, M204A, F235A, K237R, K237N, K237S, W278A, K307A, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A.

In some embodiments, the glucan phosphatase polypeptide variant comprises the sequence of SEQ ID NO: 1 comprising at least one amino acid mutations selected from the group consisting of Y139A, F167A, M204A, F235A, K237R, K237N, K237S, W278A, K307A, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A, and further comprising up to 10 conservative amino acid substitutions.

In still further embodiments the glucan phosphatase polypeptide variant is selected from a glucan phosphatase polypeptide variant set forth in Table 2. Table 2 includes the amino acid mutations for a wild type glucan phosphatase polypeptide that has the amino acid sequence associated with SEQ ID NO: 2. Embodiments of the presently-disclosed subject matter also comprise any combination and variation of mutations in Table 2.

TABLE 2

Amino Acid Mutations Associated with SEQ ID NO: 2

| Single Mutant | | | | | | Double Mutant |
|---|---|---|---|---|---|---|
| LSF2 C/S | A195E | G230A | F162A | S177Y | LSF2 + sex4CBM | W136A/F162A |
| S194A | L197M | K233A | F162T | W180A | G230F | W180A/F261A |
| S194K | Q129A | N232A | F162N | ΔRGT | N232K | G230F/N232K |
| S194T | D130A | Y135A | R153A | K250A | G230Y | G230Y/N232D |
| S194N | K131A | Y85A | M155A | E251A | N232D | |
| S194Q | D163A | Y83A | R156A | N159A | W136F | |
| A195G | D161A | W136A | R157A | F261A | W136N | |
| A195M | D132A | W136M | S177A | D263A | K245A | |
| A195D | K160A | F162Y | S177R | W267A | | |
| A195H | G198A | F162M | S177Q | E268A | | |

In some embodiments, the glucan phosphatase polypeptide variant can additionally include up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 additional amino acid substitutions relative to SEQ ID NO: 2. In some embodiments, the additional amino acid substitutions are conservative amino acid substitutions. In some embodiments, the additional amino acid substitutions do not substantially alter function of the polypeptide. In some embodiments, the additional amino acid substitutions are not located in a Dual Specificity Phosphatase (DSP) domain of the glucan phosphatase polypeptide.

In some embodiments, the glucan phosphatase polypeptide variant can comprise a wild type amino acid sequence corresponding to a fragment of SEQ ID NO: 2 comprising a mutation or combination of mutations selected from the group consisting of S194A, S194K, S194T, S194N, S194Q, A195G, A195M, A195D, A195H, A195E, L197M, Q129A, D130A, K131A, D163A, D161A, D132A, K160A, G198A, G230A, K233A, N232A, Y135A, Y85A, Y83A, W136A, W136A/F162A, W136M, F162Y, F162M, F162A, F162T, F162N, R153A, M155A, R156A, R157A, S177A, S177R, S177Q, S177Y, W180A, W180A/F261A, LSF2-C-terminal- RGT, K250A, E251A, N159A, F261A, D263A, W267A, E268A, LSF2+sex4CBM, G230F, G230F/N232K, N232K, G230Y, G230Y/N232D, N232D, W136F, W136N, and K245A. The fragment of SEQ ID NO: 2 can include up to about 1, 2, 3, 4, 5, 6, 7, 8, 9, or 10 amino acid deletions from the N-terminus or up to about 1, 2, 3, 4, 5, 6, 7, 8, 9, 10, 11, 12, 13, 14, 15, 16, 17, 18, 19, or 20 amino acid deletions from the C-terminus. Fragments are typically at least about 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, or 281 amino acids long.

In some embodiments, the glucan phosphatase polypeptide variant comprises a sequence having at least 85, 86, 87, 88, 89, 90, 91, 92, 93, 94, 95, 96, 97, 98, or 99% homology to a polypeptide having the sequence of SEQ ID NO: 2 comprising at least one amino acid mutations selected from the group consisting of S194A, S194K, S194T, S194N, S194Q, A195G, A195M, A195D, A195H, A195E, L197M, Q129A, D130A, K131A, D163A, D161A, D132A, K160A, G198A, G230A, K233A, N232A, Y135A, Y85A, Y83A, W136A, W136A/F162A, W136M, F162Y, F162M, F162A, F162T, F162N, R153A, M155A, R156A, R157A, S177A, S177R, S177Q, S177Y, W180A, W180A/F261A, LSF2-C-terminal-RGT, K250A, E251A, N159A, F261A, D263A, W267A, E268A, LSF2+sex4CBM, G230F, G230F/N232K, N232K, G230Y, G230Y/N232D, N232D, W136F, W136N and K245A.

I some embodiments, the glucan phosphatase polypeptide variant comprises the sequence of SEQ ID NO: 2 comprising at least one amino acid mutations selected from the group consisting of S194A, S194K, S194T, S194N, S194Q, A195G, A195M, A195D, A195H, A195E, L197M, Q129A, D130A, K131A, D163A, D161A, D132A, K160A, G198A, G230A, K233A, N232A, Y135A, Y85A, Y83A, W136A, W136A/F162A, W136M, F162Y, F162M, F162A, F162T, F162N, R153A, M155A, R156A, R157A, S177A, S177R, S177Q, S177Y, W180A, W180A/F261A, LSF2-C-terminal-RGT, K250A, E251A, N159A, F261A, D263A, W267A, E268A, LSF2+sex4CBM, G230F, G230F/N232K, N232K, G230Y, G230Y/N232D, N232D, W136F, W136N and K245A, and further comprising up to 10 conservative amino acid substitutions.

As used herein, the terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "variant" refers to an amino acid sequence that is different from the reference polypeptide by one or more amino acids, e.g., one or more amino acid substitutions. For example a glucan phosphate polypeptide variant differs from wild-type glucan phosphatase by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide. In this regard, the presently-disclosed subject matter is inclusive of variants having the particular mutations disclosed herein that impact efficacy of the polypeptide for particular utilities, which variants can have one or more additional mutations that to not substantially impact efficacy of the polypeptide for the particular utilities. For example, in some embodiments, conservative amino acid substitutions can be made without substantially impacting efficacy. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another. In some embodiments, a variant can have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 additional mutations that are conservative substitutions.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus, carboxy-terminus of the reference polypeptide, or alternatively both. A fragment can also be a "functional fragment," in which case the fragment retains some or all of the activity of the reference polypeptide as described herein "Percent identity," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). [BLAST nucleotide searches are performed with the NBLAST program, score+100, wordlength=12, to obtain nucleotide sequences homologous to a nucleic acid molecule of the invention. BLAST protein searches are performed with the XBLAST program, score=50, word length=3, to obtain amino acid sequences homologous to a reference polypeptide (e.g., SEQ ID NO: X). To obtain gapped alignments for comparison purposes, Gapped BLAST is utilized as described in Altschul, et al. (Nucleic Acids Res. 25: 3389-3402, 1997). When utilizing BLAST and Gapped BLAST programs, the default parameters of the respective programs (e.g., XBLAST and NBLAST) are used. See http://www.ncbi.nlm.nik.gov, and reference is made to the most recent version of the programs that are available as of Jul. 19, 2012.

Glucan phosphatases dephosphorylate glucans in starch in starch metabolism. In some instances, glucan phosphatases dephosphorylate glucans so that starch can be completely degraded by β-amylase. Thus, mutations in the amino acid sequences of glucan phosphatase polypeptide variants can affect the metabolism of starch.

Some embodiments comprise a composition including starch that is from a plant expressing a glucan phosphatase variant having an amino acid mutation. As discussed above, plants expressing a glucan phosphatase polypeptide variant can produce starch with altered biophysical properties, which can be beneficial for manufacturing processes in various industries, including food, beverage, confectionary, plastic, paper, building, energy, textile, agriculture, and pharmaceutical industries. Plants expressing embodiments of glucan phosphatase polypeptide variants can also exhibit increased starch biomass production relative to plants expressing wild type glucan phosphatases, and increased starch biomass can be useful in biofuel industries, for example.

Some embodiments include a method of producing starch, which comprises providing a plant that comprises a glucan phosphatase polypeptide variant, as disclosed herein, comprising an amino acid mutation and collecting starch from the plant. The term "plant" is used herein to refer to any plant that can produce starch for collection.

In this regard, the term "providing", when used in reference to a plant, is used herein to refer to the act of delivering, obtaining, procuring, or the like a plant. In essence, providing a plant generally refers to making a plant available to one who wishes to collect starch from the plant. The term "collecting" is used herein to refer to any process or method where starch is used, obtained, cultivated, ingested, or the like. For example, in some embodiments starch is collected by harvesting a plant that comprises starch and processing the plant in order to obtain starch or other sugars derived therefrom. In some embodiments, collecting refers to ingesting a plant that comprises a glucan phosphatase polypeptide variant.

The presently-disclosed subject matter is further illustrated by the following specific but non-limiting examples. Some examples are prophetic. Some of the following examples may include compilations of data that are representative of data gathered at various times during the course of development and experimentation related to the presently-disclosed subject matter.

EXAMPLES

Example 1

Identifying and Characterizing Structure of Glucan Phosphatases

In the following examples various assays are used to identify and characterize the structure of glucan phosphatases. A glucan-binding assay was used to assess interactions between glucan phosphatases and glucans (Gentry (2007), Gentry (2009), Worby (2006), Vander Kooi (2010), Hsu (2009)). Amylopectin with a protein of interest was incubated and thereafter a high-speed spin was performed and proteins in the pellet and supernatant were analyzed via Western analysis. Proteins binding glucans pellet with the glucan, whereas those not binding remain in the supernatant. To test generic activity, a phosphatase assay using the exogenous substrate para-nitrophenyl phosphate (pNPP) or 3-O-Methylfluorescein (OMFP) was implemented, which can also determine kinetic parameters (Gentry (2007), Gentry (2009), Santelia (2011), Kotting (2009), Worby (2006), Dukhande (2011)). Most DSPs can cleave pNPP or OMFP, resulting in a colorimetric change.

Furthermore, to test glucan phosphatase activity and glucan binding, an assay based on the complex formation of malachite green with phospho-olybdate to measure inorganic phosphate release was implemented (Van Veldhoven (1987)). The glucan phosphatase assay measures the release of inorganic phosphate from any phospho-glucan. Using this assay, it was demonstrated that mutations in the CBM of laforin and SEX4 that reduce or abolish glucan binding also reduce or eliminate glucan phosphatase activity (Gentry (2007)). While this assay utilizes an endogenous substrate, one can only determine a specific activity and cannot obtain kinetic parameters due to the heterogeneity of the substrate, i.e. phosphate within amylopectin.

Lastly, an endogenous substrate was utilized to measure the position phosphate is released off of glucose and kinetic parameters (Santelia (2001), Kotting (2009)). Starch was isolated from plants lacking the two dikinases (GWD and PWD), so that the starch contained very little to no phosphate, and used the sample was dialyzed to remove free phosphate. The C6 position was radio-labeled by adding GWD in the presence of $^{33}$P-β-ATP (dikinases transfer the β-phosphate), dialyzing and precipitating out the $^{33}$P-β-ATP and GWD, adding non-radio-labeled ATP with PWD, dialyzing and precipitate out the ATP and PWD, and utilizing this starch as the substrate. The C3 position was radio-labeled by adding $^{33}$P-β-ATP with PWD instead of with GWD.

Figure 3A:
FIG. 3A shows the SEX4 domains.
Figure 3B:
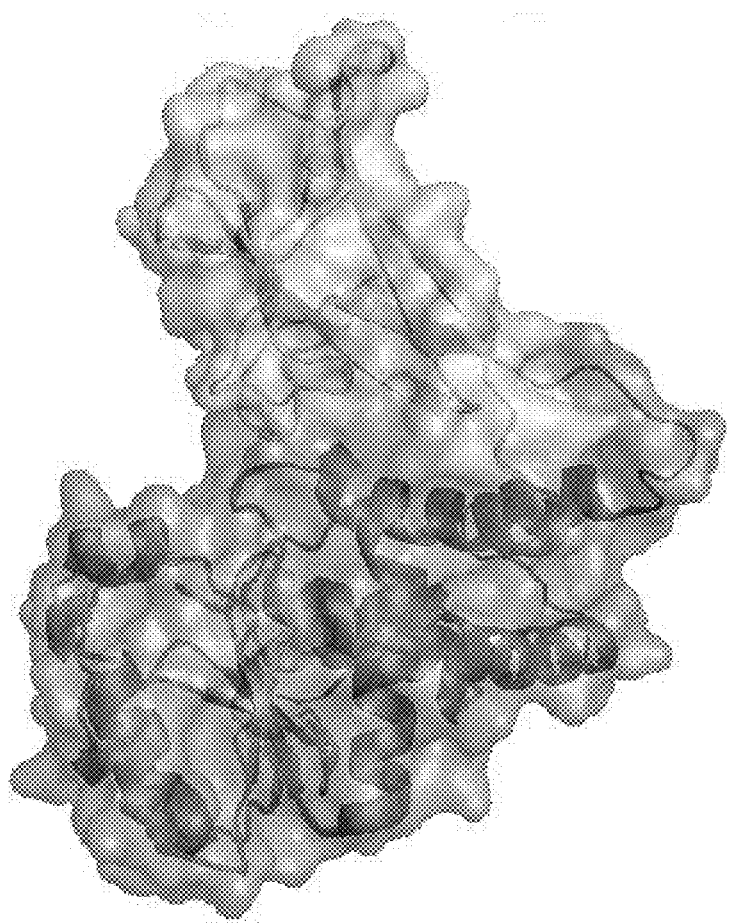
FIG. 3B depicts the integrated architecture of DSP (pink), CBM (green), and C-terminal (blue) domains.
Figure 3C:
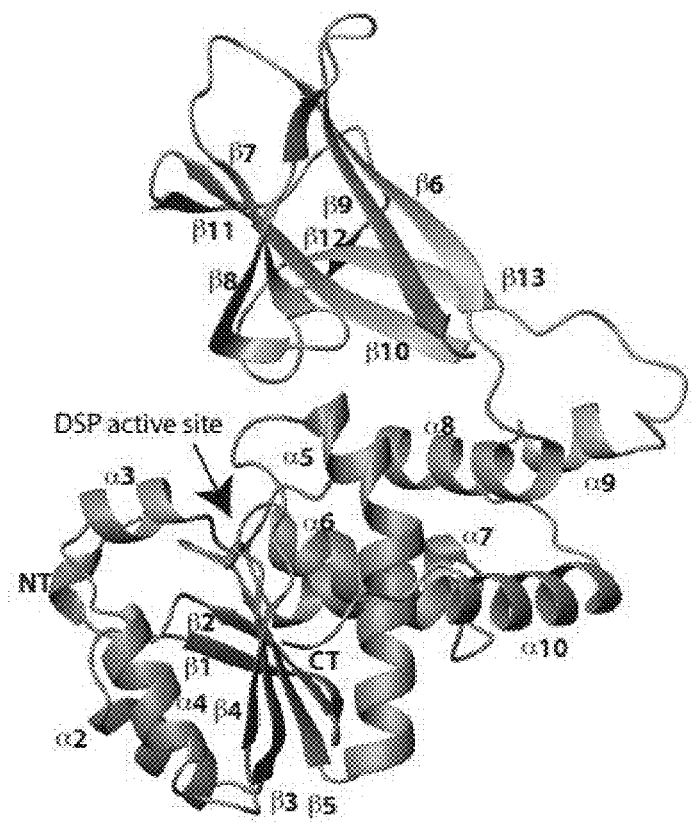
FIG. 3C depicts a ribbon diagram of SEX4 (residues 90-379), in which elements of secondary structure are numbered consecutively from N- to C-termini (PDB: 3NME).
Figure 4:
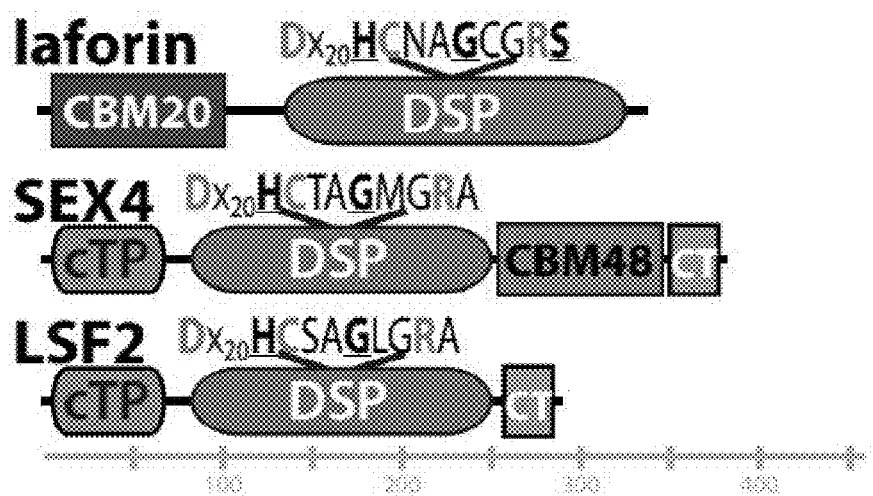
FIG. 4 shows the domains of laforin, SEX4, and LSF2 glucan phosphatases, wherein the catalytic site motif is shown above each DSP, in accordance with the present invention.

The structure of SEX4 to 2.4 Å was determined using selenomethionine single-wavelength anomalous dispersion (SAD) (55). The structure revealed a unique set of extensive interdomain interactions producing a complex tertiary architecture composed of an N-terminal DSP domain, CBM, and a C-terminal domain (FIG. 4). The novel C-terminal domain is structurally integrated into the DSP domain. Extensive DSP-CBM interactions position the DSP active site in alignment with the CBM binding site, and a long deep channel is formed by the CBM-DSP interface (FIG. 3A-3C). In addition, the CBM binding site and DSP active site are separated by 21 Å, suggesting that a glucan composed of five to six glucose moieties spans this region. All of these features differentiate SEX4 from phosphatases that dephosphorylate proteinaceous substrates.

Figure 5A:
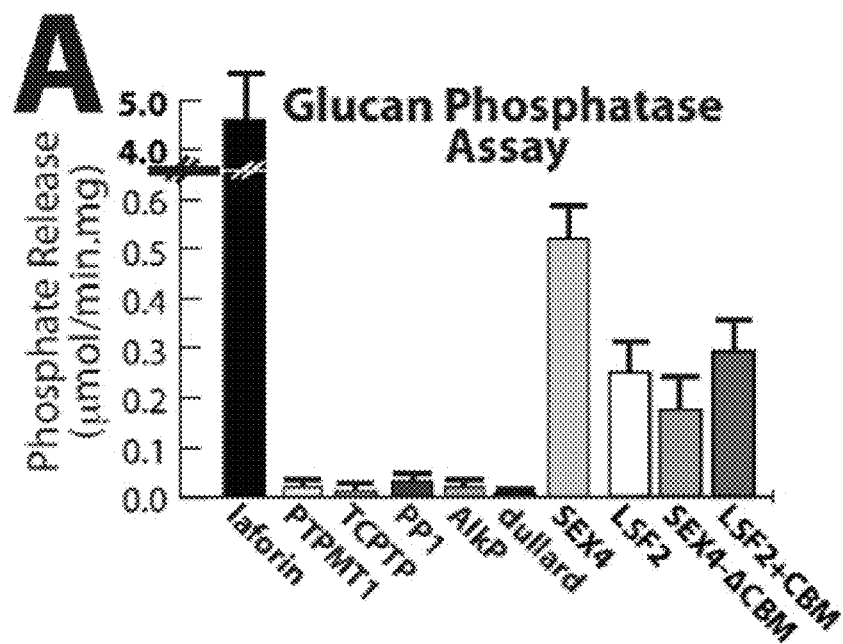
FIG. 5A is a graph showing release of phosphate from phospho-glucans by different phosphatases.
Figure 5B:
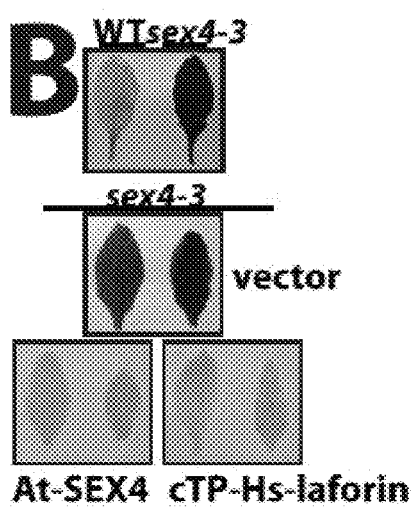
FIG. 5B shows laforin targeted to the chloroplast via a chloroplast targeting peptide (cTP) replaces SEX4 in *Arabidopsis*.
Figure 5C:
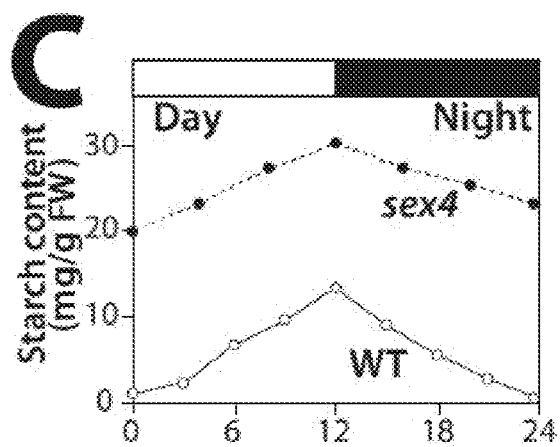
FIG. 5C shows starch content/fresh weight (FW) in WT and sex4−/− plants.

Like Sex Four2 (LSF2) is another glucan phosphatase. Knowing the SEX4 structure, it was determined that LSF2 contains a similar CT-domain as SEX4. The LSF2 cTP and DSP domain are 30% and 63% similar to SEX4, respectively, but LSF2 lacks a CBM (FIG. 4). The above-described assays were utilized to find that LSF2 is a glucan phosphatase because it binds and dephosphorylates phosphoglucans, whereas phosphatases from every other phosphatase family do not (FIG. 5A, FIG. 5E). In the assay it was discovered that LSF2 only removes phosphate from the C3 position and not the C6 position (FIG. 6) (Santelia (2011)). Subsequently, plants lacking LSF2 were shown to have increased levels of C3-phosphorylated starch and that lsf2 sex4 double mutant plants exhibited an exacerbated starch excess phenotype (21).

LSF2 independently binds and dephosphorylates starch (FIG. 5A-5E) (Santelia (2011)). Therefore, without being bound by theory or mechanism, it is believed that the LSF2 DSP and/or CT domains contain previously unrecognized glucan-binding regions. Using bioinformatics on LSF2, SEX4, and laforin, two regions within the DSP domain of glucan phosphatases were uncovered that share remote homology to glycosyl hydrolase-like domains. Glycosyl hydrolases (GH) enzymes hydrolyze glycosidic bonds between either two or more carbohydrates or between a carbohydrate and non-carbohydrate (Henrissat (1991).

The regions of the glucan phosphatase DSPs that resemble GH are within the variable loop and R-motif. However, quantifying glucose release of all three phophatases against glucan substrates detected no glycosyl hydrolase activity. Nevertheless, these two regions are highly conserved among proteinaceous DSPs, and are divergent between SEX4 and proteinaceous DSPs at the primary and secondary amino acid levels (Vander Kooi (2010). The structure of SEX4 and the prototypical DSP VHR also were found to diverge considerably.

Without being bound by theory or mechanism, these data suggest that GH-like regions play an integral role in glucan phosphatase function.

Figure 7A:
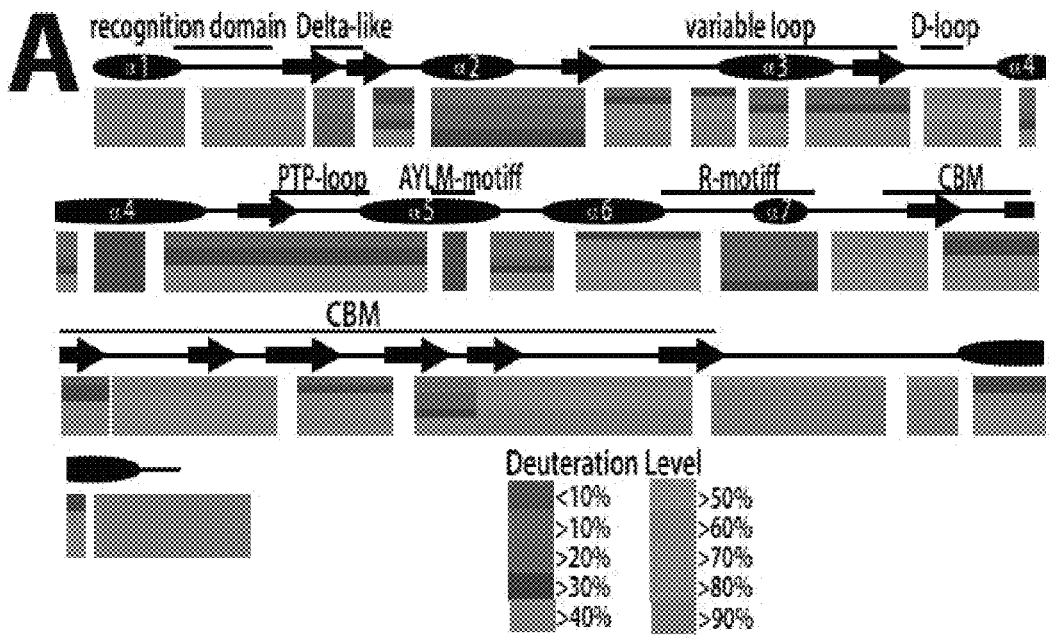
FIG. 7A-7E relate to the structural dynamics of SEX4.
Figure 7B:
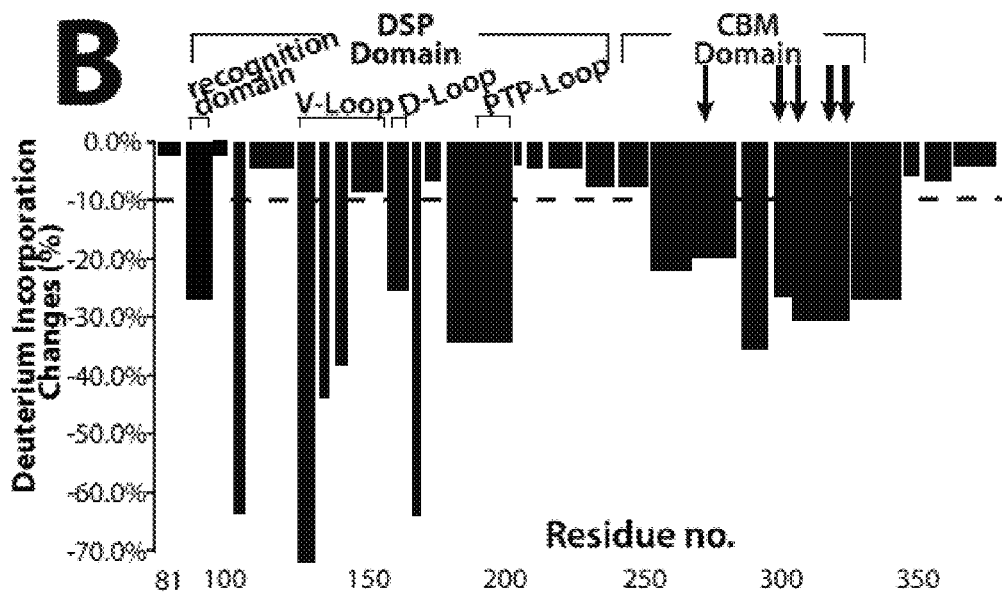
Figures 7C, 7D:
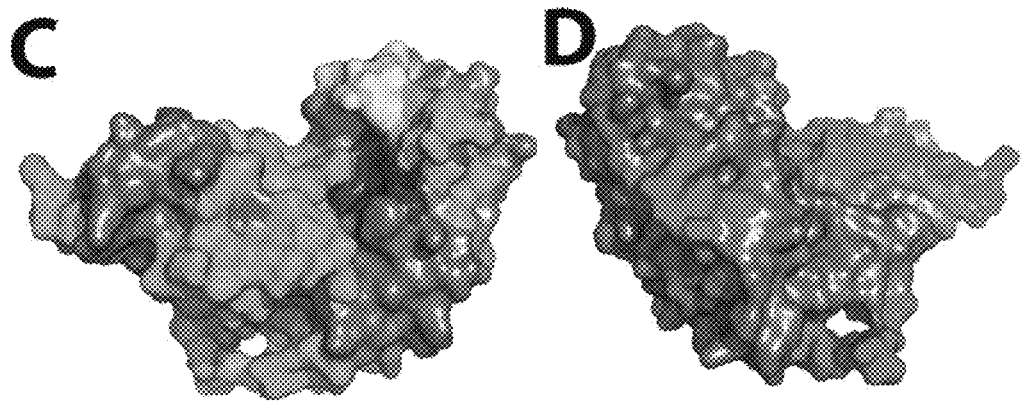
Figure 7E:
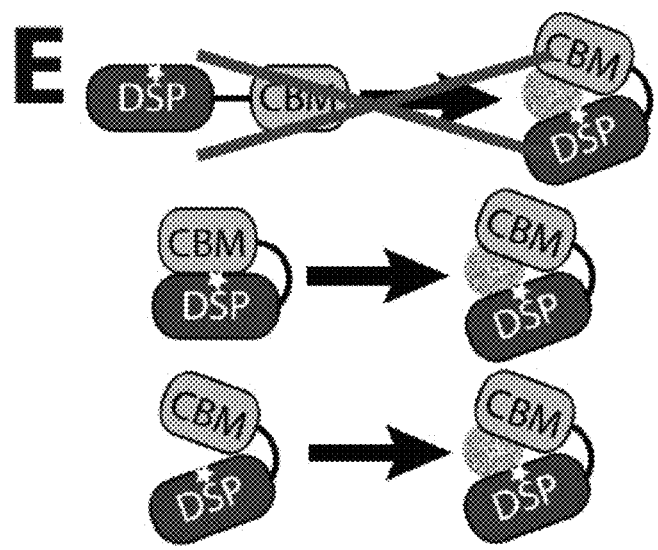

Hydrogen/Deuterium Exchange Mass Spectrometry (DXMS) was then used to define the structural dynamics of SEX4 and which portions of SEX4 interact with the substrate (Hsu (2009)). First, SEX4-HIS$_6$ was purified from *E. coli* to >99% homogeneity, pepsin digestion conditions were optimized, and the deuteration rate of each peptide for both ligand-free and amylopectin-bound SEX4 was determined (FIG. 7A-7E). The DXMS results were analyzed using the primary and predicted secondary structure of SEX4 (FIG. 7B). It appears that the CBM undergoes increased protection from deuteration when bound to glucans (FIG. 7C), and structural components of the DSP domain undergo increased protection upon glucan addition (FIGS. 7C and 7D). of these regions corresponds to the putative GH-like regions. Thus, it appears that SEX4 does not undergo a global conformational change upon glucan binding, but instead SEX4 undergoes minimal rearrangement upon binding, and the DSP domain makes extensive and intimate contact with phospho-glucans.

Example 2

Characterization of Enzymatic Activity and Specific Domains of Glucan Phosphatases In this example the differences between SEX4 and LSF2 are characterized according to their structures. The distinguishing structures, including particular domains and amino acids, are further investigated to determine how they may be utilized to engineering starch.

Figures 8A, 8B, 8C, 8D:
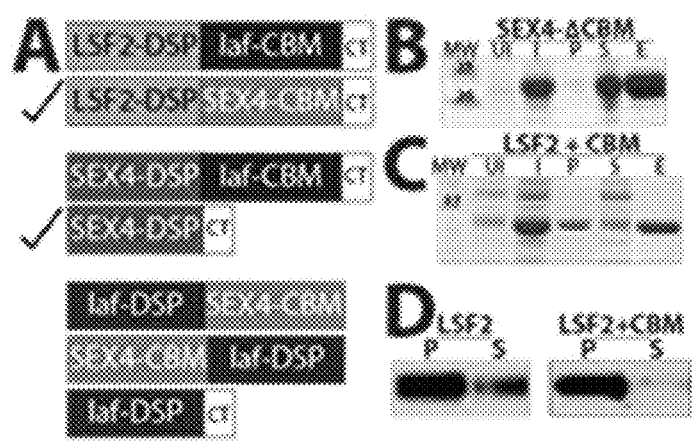
FIG. 8A shows Chimera constructs of GP domains.
FIG. 8B shows expression of SEX4-ΔCBM.
FIG. 8C shows an expression of LSF2+CBM (UI—uninduced; I—induced; P—pellet/insoluble; S—soluble; E—elution).
FIG. 8D shows LSF2+CBM and LSF2 glucan binding.

First, a SEX4 construct that lacked a CBM (SEX4-ΔCBM), making it LSF2-like, and a fusion of the LSF2_DSP+SEX4_CBM/CT were generated and yielded soluble recombinant protein (FIG. 8A-C). The chimeras were both found to possess generic/pNPP phosphatase activity and glucan phosphatase activity. The LSF2+CBM fusion had increased binding to amylopectin (FIG. 8D), but did not exhibit increased glucan phosphatase specific activity (FIG. 5A). These results suggest that the engineered LSF2 enzyme has increased glucan binding compared to LSF2, but that the LSF2+CBM fusion is unable to dephosphorylate any more phospho-glucans than LSF2-WT. Without being bound by theory or mechanism, the LSF2+CBM fusion is likely only dephosphorylating the C3-phosphate that accounts for ~30% of phosphate within starch. Subsequently, the dephosphorylation kinetics and the activity of the other chimeras will be examined using the C3 versus C6 dephosphorylation assay.

Each glucan phosphatase contains the classical active site residues ($Dx_{20}HCx_5R$), but they contain differences within this region. Laforin is the only glucan phosphatase that contains all of the consensus catalytic site residues that are historically known to affect dephosphorylation efficiency, i.e. $Dx_{20}HCxxGxxRS/T$ (i.e. $Cx_5R$). These residues actively participate in dephosphorylation (D, C, R), contribute to the architecture of the active site (G), or decrease the pKa of the active site Cys (H and S/T) (Alonso (2003)). SEX4 and LSF2 both possess a terminal Ala instead of the typical Ser/Thr, and may possess different preferences and/or perform dephosphorylation with different kinetics. The active site residues likely impose steric hindrance against either a C3- or C6-bound phosphate, thus impacting specificity.

To define the amino acids contributing to glucan phosphatase activity and specificity, each catalytic site will be mutated and the activity of the mutants analyzed using the assays in Example 1. Initially, the $Cx_5R$ of one glucan phosphatase will be swapped with that of another. Once the LSF2 structure is completed, the LSF2 active site architecture will be compared to that of SEX4. Collectively, the studies will uncover novel aspects of each enzyme, define the inherent activity of each DSP domain, and determine the amino acids responsible for these activities. In addition, these engineered proteins can be used to yield different substrate specificities with respect to C3 versus C6 kinetics and produce designer starches in vitro and/or when over-expressed in planta.

Example 3

Characterization of Glycosyl Hydrolase Regions in the DSP

As presented in Example 1, two regions within the DSP domain of glucan phosphatases are similar to glycosyl hydrolase family 1 (GH1) and family 10 (GH10) motifs and are located within the R-motif and variable loop, respectively, of the DSP domain. The R-motif is highly conserved among classical protein DSPs (64), but the glucan phosphatases share no homology with protein DSPs in this region. The variable loop contributes to the depth of the active site, and it assists in positioning the active site arginine to interact with the phosphate of the substrate (Alonso (2003)). Thus, these regions are well positioned to assist in phospho-glucan presentation to the active site and share no homology with proteinaceous DSPs, but are well conserved among glucan phosphatase orthologs. Since LSF2 lacks a CBM yet still possesses glucan phosphatase activity, this Example investigates whether these regions coordinate glucan presentation to the LSF2 active site by binding and positioning phosphoglucans to promote dephosphorylation.

Mutations in both GH-like regions of LSF2 were generated to determine if the bioinformatics analyses identified regions within the DSP domain of LSF2 necessary for glucan dephosphorylation. The proteins were purified and tested for their generic and glucan phosphatase activities. The mutants retained similar specific activities to LSF2, but their glucan phosphatase specific activities are dramatically decreased.

Corroborating these results is the fact that several point mutations in these two regions within laforin cause Lafora disease (GH10-like: T187A & T196I, and GH1-like: Q293L, Y294N, P301L). Thus, these point mutations may diminish the ability of the laforin DSP domain to interact with and dephosphorylate phospho-glucans, supporting the notion that GH-like regions within the DSP domain play an important role in glucan dephosphorylation.

Alanine scanning was performed by mutating blocks of amino acids in these regions to alanine (i.e. for SEX4 we will mutate DPDL in the R-motif to AAAA). Glucan phosphatase activity of SEX4 and LSF2 will be tested to see if it is inhibited by mutating blocks of amino acids in these regions, while not affecting or minimally affecting generic phosphatase activity (i.e. pNPP). The C3/C6 assay will determine catalytic efficiencies of these mutants and determine if the mutations affect specificity.

Since SEX4 and LSF2 have relatively lower specific activity for dephosphorylating phospho-glucans, their catalytic efficiencies will be observed after mutating their GH1- and GH10-like regions to match the GH1 and GH10 consensus sequences. Enhancing glucan phosphatase activity by mutating one and/or both of these regions further strengthens the notion that these regions play an important role in glucan dephosphorylation.

These experiments will determine if the glucan phosphatase activity of SEX4 and LSF2 can be separated from generic phosphatase activity as well as the kinetics of glucan dephosphorylation. This will show the role of the different domains, including the GH-like regions within their DSP domains, and amino acids in directing glucan dephosphorylation. These findings will provide one or more regions to target with a small molecule to modulate glucan phosphates activity to eventually modulate energy stores.

Example 4

Characterization of Structural Dynamics and/or Substrate Binding Site of Glucan Phosphatases with Hydrogen/Deuterium Exchange Mass Spectrometry (H/DXMS)

As discussed in Example 1, H/DXMS has been used to determine the structural dynamics and glucan binding sites of SEX4, and its structure was determined using x-ray crystallography (55,58). These results indicate the structural dynamics of SEX4, that specific regions within the DSP domain of SEX4 intimately interact with phospho-glucans, and the SEX4 variable loop undergoes the most dramatic substrate-induced protection from deuteration (FIG. 4). While LSF2 is a glucan phosphatase, there are substantial differences between the two proteins. This Example will determine how glucan phosphatases, including LSF2, interact with starch, modulate starch dephosphorylation, and elucidate their role in energy release.

Greater than 99% pure glucan phosphatases were produced with a two-step purification process using an HIS-affinity column and Profinia system (BioRad) followed by gel filtration chromatography with a HiLoad 26/60 Superdex 200 and AKTA Purifier (GE), which purified ≈25 mg of soluble SEX4 and LSF2/liter of *E. coli* cells (Vander Kooi (2010), Hsu (2009)).

To define LSF2 digestion conditions to maximize MS/MS mass spectrometry coverage, LSF2 digestion was tested under similar conditions that were optimal for SEX4, 0.5 M guanidine hydrochloride and 1 M Tric-2-carboxyethyl phosphine (reducing agent) with a pepsin column, and the peptide products will then undergo LC-MS/MS analyses. Once these conditions were optimized, the H/D exchange of ligand-free LSF2 at eight time points from 10 s to 10,000s (166 minutes) was determined. These data was combined with the LSF2 peptide map of LSF2, as was done for SEX4 in FIG. 7A, to determine which regions of LSF2 are more or less accessible to H/D exchange.

The same experiment will also be performed in the presence of a glucan. In SEX4 DXMS studies, both large glucans (amylopectin) and small glucans (β-cyclodextrin) interact with the SEX4 DSP domain (FIG. 7A-7E) (Hsu (2009)). Here, the small, homogenous ringed-glucan β-cyclodextrin; the small homogenous linear maltohexaose; and the large, heterogeneous, highly phosphorylated glucan amylopectin will be utilized. Methodologies to immobilize SEX4 and LSF2 on SPR chips and binding experiments with each protein and multiple oligosaccharides will use a Biacore T100 (GE Healthcare). Thus, this Example defines the interaction between LSF2 with multiple glucans at a molecular resolution, and the binding affinities for LSF2 and SEX4 with multiple glucans, the outer and inner surfaces via DXMS.

Once the analysis of wild type LSF2 by DXMS is optimized, DXMS will be used to probe the structural dynamics of the GH-like regions of LSF2 mutants and SEX4 mutants discuss above. Notably, out of 32 SEX4 mutants and 12 LSF2 mutants that have been generated, all purify to similar purities, in buffers of similar composition, and to similar yields as the respective wild type protein.

DXMS experiments similar to those outlined above will be carried out on mutant LSF2 and SEX4. Mutants can be selected for analysis based on data from Example 3, being most interested in 1) mutants that increase glucan phosphatase activity and 2) those that retain glucan binding and pNPP/generic phosphatase activity while exhibiting decreased glucan phosphatase activity. The H/D exchange rate for the ligand-free mutants will be defined, and the results will determine if the mutations cause global conformational changes, or if they cause minimal to no change in their conformation. With these results one can determine the structural dynamics and/or glucan binding of mutants when they bind amylopectin or oligosaccharides.

If the GH-like regions are necessary for positioning the phospho-glucan, then the DXMS results of the mutant proteins should show a substantial decrease in substrate-induced protection from H/D exchange. However, if the GH-like regions play little role in positioning and binding the phospho-glucan, then there should be minimal change in the rate of substrate-induced H/D exchange between mutants and wild type proteins. Once the motifs within the DSP domain that interact with glucans are identified, they can be targeted with point mutations and/or small molecules to increase/decrease glucan phosphatase activity.

Example 5

Characterization of Glucan Phosphatases Crystal Structure

This Example will determine how glucans are accommodated by glucan phosphatases that have a CBM (i.e. SEX4) and those that lack a CBM (i.e. LSF2), the characteristics that yield specificity for different types of substrates (i.e. C3 v. C6 and soluble v. crystalline), and how such activity can be modified.

LSF2 primary sequences from multiple species were analyzed using prediction programs to define domain boundaries, establish predicted secondary structure, predict regions of disorder, and define regions of hydrophobicity. Based on these data, the full-length *Arabidopsis* LSF2 gene was cloned as well as multiple truncations that remove different sections of the chloroplast Targeting Peptide (cTP). Similar methodologies successfully guided SEX4 cloning strategies (Vander Kooi (2010)).

Full length LSF2 was largely insoluble when expressed in *E. coli*, but Δ78-LSF2 produced large amounts of soluble protein. Δ78-LSF2 was purified to homogeneity using a two-step purification process as discussed in Example 4. 30-40 mg of soluble Δ78-LSF2/L of *E. coli*, was produced and made in a concentration of >15 mg/ml that it is stable for >2 weeks at 4° C.

A mosquito crystallization robotics station (TTP Labtech) was used to identify conditions that produced LSF2 diffraction quality crystals (Vander Kooi (2010). Many crystallization conditions were screened with minimal total protein requirements. The default protocol involved performing hanging drop vapor diffusion experiments in 96-well plates with three drops per well. The three drops were each 200 nL and had differing protein:mother liquor ratios (typically 3:1, 1:1, 1:3), which required 42 μL for the 288 conditions in each 96 well plate.

Figure 9A:
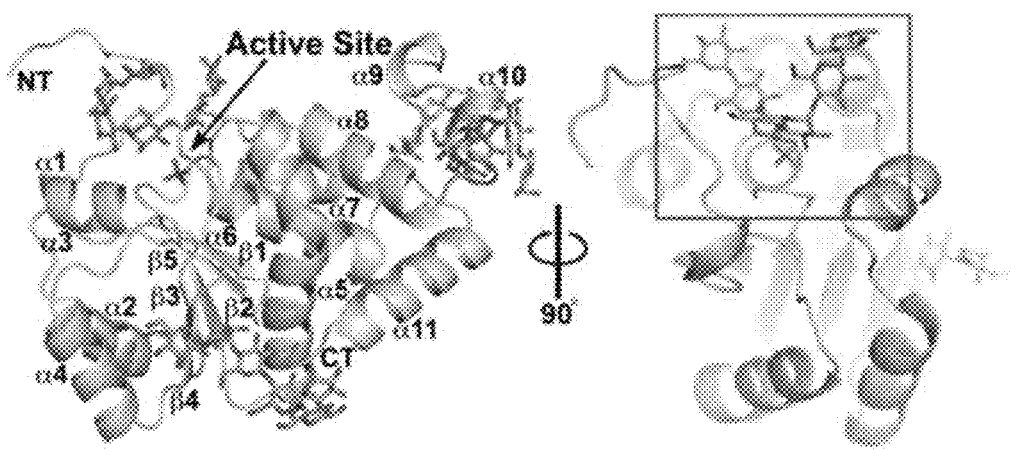
Figure 9B:
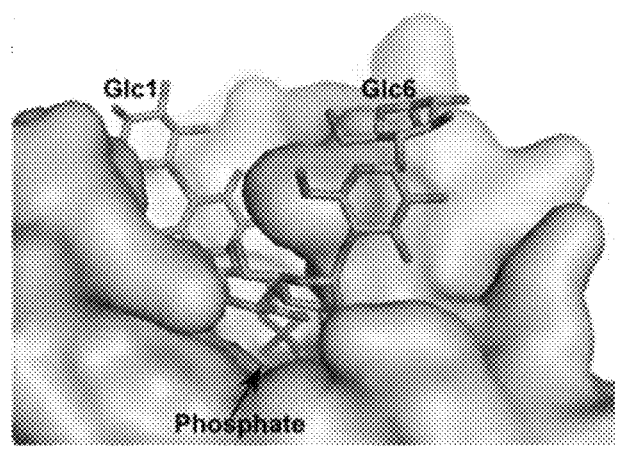
Figure 9C:
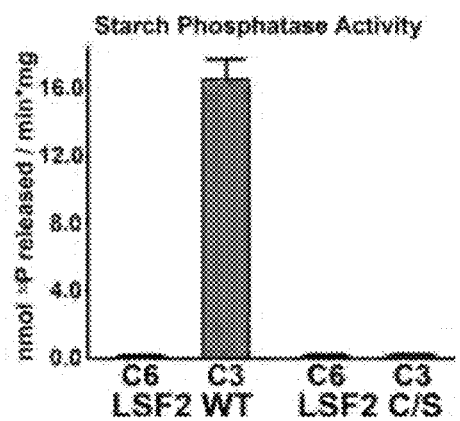

Initially, the process comprised multiple sparse matrix commercial screens and then several rounds of optimization before obtaining crystals of sufficient dimensions to analyze (at the UK Center for Structural Biology core facility). Full datasets to ~3.5 Å and to ~1.65 Å at the SER-CAT beamline were collected at the Advanced Photon Source (Argonne National Laboratory) (FIG. 9A-9C). Molecular replacement was suitable for deriving initial phases of LSF2. These data are being iteratively refined using Refmac and coot (FIG. 9A-9C) (Emsley (2004), Murshudov (1997)).

The above described SEX4 structure was a glucan-free structure (FIG. 3A-3C) (Vander Kooi (2010)). Given the heterogeneity of starch, it has proven difficult to correctly model a glucan chain into the SEX4 glucan binding pocket. Observing the structure, 21 Å separate the CBM binding site and the DSP active site, which is enough distance for a 5-6 glucose chain (i.e. maltopentaose or -hexaose). Determining a structure with bound glucan would shed light on the residues that directly interact with the glucan. Therefore, crystallization was studied in the absence and presence of phosphate plus multiple glucan additives including maltotetraose, maltohexaose, maltopentaose, maltotriose, α-maltosyl-β-cyclo-dextrin, and others. Several conditions yielded crystals with SEX4, which will be analyzed as described above. Similar studies will also be done with LSF2. These results will be enhanced by, but do not depend on, SPR and ITC analyses.

The glucan-free structure of SEX4 uncovered a number of interesting structural features regarding glucan dephosphorylation, including 1) adaption of multiple phosphatase motifs to accommodate interdomain interactions, 2) a novel CT domain that is structurally integrated with the DSP domain, 3) alignment of the DSP active site with the CBM glucan binding pocket and separated by 21 Å, 4) motifs allowing a 10° rotation of the CBM-DSP pockets that may allow processive substrate dephosphorylation, and 5) a channel formed by the CBM-DSP interface capable of accommodating both phospho-oligosaccharides as well as a more crystalline substrate (e.g. starch) (55). As discussed above, certain regions within SEX4 may account for these structural and functional features and multiple point mutations have been generated to investigate these aspects of glucan dephosphorylation. Similar experiments will be conducted for LSF2 to further define glucan phosphatases in general. This Example will define the subregions within the DSP domain that bind glucans and determine the characteristics that yield specificity for different types of glucans.

Cloning, Expression, and Purification of Recombinant Proteins

Cloning of full length *Arabidopsis thaliana* LSF2 from cDNA was previously described (Santelia (2011)). Based on data from secondary structure predictions, disorder predictions, sequence homology with SEX4, and analysis of LSF2 orthologs, we generated an *A. thaliana* LSF2 construct lacking the first 78 amino acids (Δ78-LSF2). Δ78 LSF2 does not contain the cTP (predicted to be residues 1-65) along with residues up to the DSP recognition domain. Δ78-LSF2 was subcloned into pET28 (Novagen) using NdeI and XhoI sites to encode a His6 tag, a thrombin cleavage site, and Δ78-LSF2 (Santelia (2011)). All point mutants were generated using a site-directed mutagenesis kit (Agilent) or mutagenesis services (GenScript). Cloning and purification of *A. thaliana* SEX4 lacking the first 89 amino acids (Δ89-SEX4) (Vander Kooi (2010)) and Hs-VHR (Yuvaniyama (1996)) was performed as previously described. All DNA sequencing (ACGT Inc.) was confirmed using MacVector. Amino-acid sequences of LSF2 orthologs were aligned with ClustalW in MacVector. Expression and purification of Δ78-LSF2 was performed similarly to the previously described method for Δ89-SEX4 (Vander Kooi (2010)). Briefly, BL21-CodonPlus *E. coli* cells were transformed with expression vectors for the production of native LSF2 protein. Cells were grown at 37° C. in 2xYT media to $OD_{600}$=0.6-0.8, placed on ice for 20 min, induced with 1 mM isopropyl β-D-thiogalactoside (IPTG), grown at 16° C. for 16 hr, and harvested by centrifugation. Cells were lysed in 20 mM Tris-HCl (pH 7.5), 100 mM NaCl, and 2 mM dithiothreitol (DTT), centrifuged, and the proteins were purified via a Profinia IMAC $Ni^{2+}$ column (Bio-Rad) with a Profinia protein purification system (Bio-Rad). Protein was dialyzed in 20 mM Tris-HCl (pH 7.5), 100 mM NaCl, and 2 mM dithiothreitol (DTT) overnight at 4° C. in the presence of thrombin. Affinity purified protein was then reverse purified over the Profinia IMAC $Ni^{2+}$ column and the flow-through fraction was collected. Protein was further purified to homogeneity using a HiLoad 26/60 Superdex 200 size exclusion column (GE Healthcare). Protein used for enzyme and binding assays were stored in 10% glycerol as a cryoprotectant and flash frozen for later use.

Recombinant potato GWD and recombinant *Arabidopsis* PWD for $^{33}P$ labeling of *Arabidopsis* starch were purified as previously described with the following modifications (Ritte (2002), Kotting (2005)). GWD and PWD were transformed into BL21-CodonPlus *E. coli* cells and expressed similarly to Δ78-LSF2 as stated above. GWD was lysed in buffer (50 mM Tris/HCl pH 7.5, 2.5 mM EDTA, 2.5 mM DTT, 0.5 mM PMSF), and proteins were purified using an anion exchange column (Q-sepharose-FF, GE-Healthcare) with a salt gradient (50 mM Tris/HCl pH 7.5, 2.5 mM EDTA, 2.5 mM DTT, 0.5 mM PMSF, 0.5 NaCl) to elute the protein. Fractions were collected and protein was further purified using a HiLoad 26/60 Superdex 200 size exclusion column (GE Healthcare) in new buffer (100 mM MOPS/KOH pH 7.6, 1 mM EDTA, 2 mM DTT, 0.5 mM PMSF, 150 mM NaCl). GWD was then put over a desalting column using a Bio-Scale Mini Bio-Gel P6 Desalting column (Bio-Rad) using a Profinia protein purification system (Bio-Rad). PWD was lysed in buffer (50 mM HEPES/NaOH pH 8.0, 300 mM NaCl, 10 mM imidazole, 0.5 mM PMSF), centrifuged, and proteins were purified using a Profinia IMAC $Ni^{2+}$ column (Bio-Rad) with a Profinia protein purification system (Bio-Rad). PWD was further purified using a HiLoad 26/60 Superdex 200 size exclusion column (GE Healthcare).

Crystal Structure Determination and Refinement

For glucan bound crystals single, high quality crystals, with one molecule in the asymmetric unit, were obtained via hanging drop vapor diffusion using a Mosquito liquid handling robot (TTPLabtech) using a 200 nL drop with a 1:3 ratio of Δ78-LSF2 C193S (4.8 mg/mL) preincubated with 25 mM maltohexaose (Sigma-Aldrich): 0.1M di-ammonium hydrogen phosphate (pH 5.7), 17% 2-propoanol, and 31% PEG 4000 at 18° C. Single, high quality Δ78-LSF2 wild-type crystals, with one molecule in the asymmetric unit, were obtained with a 200 nL drop using a 1:1 ratio of LSF2 (4.8 mg/mL): 0.1M tri-sodium citrate (pH 5.8), 16% 2-propanol, 31% PEG 4000, and 2% glycerol at 18° C. A single crystal was used for data collection and structural determination for both LSF2 structures. Both Δ78-LSF2 C193S (phosphate/maltohexaose) and Δ78-LSF2 wild-type (citrate) data were collected on the 22-ID beamline of SER-CAT at the Advanced Photon Source, Argonne National Laboratory (Table 1) at 110K at a wavelength of 1.0 Å. Data was processed using HKL2000 (Otwinowski and Minor (1997)). PHENIX (Adams (2010)) was used for molecular replacement using the SEX4 DSP and ☐10 helix of the SEX4 CT domain as search models (Vander Kooi (2010)). The structures were then fully built and refined via iterative model building and refinement using Coot (Emsley (2010)) and Refmac5 (Murshudov (1997)), respectively. Stereochemistry of the model was analyzed using MolProbity (Davis (2007)). Analysis and molecular graphics were prepared using Pymol (Schrodinger, 2010). Density maps were produced using the FTT program in CCP4 (Winn et al.). Comparative structure analyses were performed using the DaliServer (Holm and Rosenstrom, 2010) and DaliLite (Hasegawa and Holm (2009)). Protein-ligand contact analyses were performed with Areaimol (Lee and Richards (1971)). We deposited the models and structure factors to the Protein Database (PDB) under the file names 4KYR (Δ78-LSF2 C193S-maltohexaose/phosphate) and 4KYQ (Δ78 LSF2 wild-type).

Phosphatase Assays

Phosphatase assays using pNPP have been previously described and were performed with the following modifications (Worby (2006), Gentry (2007), Sherwood (2013)). Hydrolysis of p-NPP was performed in 50 µL reactions, containing 1× phosphatase buffer (0.1 M sodium acetate, 0.05 M bis-Tris, 0.05 M Tris-HCl pH 7.0, 2 mM dithiothreitol), 50 mM pNPP, and 1 µg of enzyme at 37° C. for 15 min. The reaction was terminated by the addition of 200 µL of 0.25 NaOH and absorbance was measured at 410 nm. The assay was performed with each protein ≥6 times to determine specific activity.

Phosphate release from $^{33}$P-Labeled granules was performed as previously described with the following variations (Hejazi (2010), Santelia (2011)). C6-$^{33}$P-labeled starch was generated by isolating phosphate-free starch granules from the *Arabidopsis* sex1-3 mutant (Yu (2001)), phosphorylating the starch with $^{33}$P at the C6-position by GWD followed by a stringent wash. Phosphorylation with unlabeled ATP at the C3-position by PWD was performed as previously described (Hejazi (2010)). C3-$^{33}$P-labeled starch was generated by isolating phosphate-free starch granules from the *Arabidopsis* sex1-3 mutant (Yu (2001)), phosphorylating the starch with unlabeled ATP at the C6-position by GWD followed by a stringent wash and phosphorylation with $^{33}$P at the C3-position by PWD as previously described (Hejazi (2010)). In both cases the starch granules were phosphorylated at both positions, however the $^{33}$P-label was located at only one or the other position. [β-$^{33}$P]ATP was obtained from Hartmann Analytic. Recombinant proteins (150 ng) were incubated in dephosphorylation buffer (100 mM sodium acetate, 50 mM bis-Tris, 50 mM Tris-HCl, pH 6.5, 0.05% [v/v] Triton X-100, 1 µg/µL [w/v] BSA, and 2 mM DTT) with C6- or C3-prelabeled starch (4 mg/mL) in a final volume of 150 µL on a rotating wheel for 5 min at 25° C. The reaction was terminated by the addition of 50 µL 10% SDS. The reaction tubes were then centrifuged at 13,000 rpm for 5 minutes to pellet the starch. $^{33}$P release into 150 µL of supernatant was determined using a 1900 TR liquid scintillation counter (Packard). The assay was performed with each protein ≤6 times to determine specific activity.

Glucan Binding Assay

Glucan-binding assays were performed as previously described with the following modifications (Gentry (2007), Dukhande (2011)). All proteins used in the glucan-binding assays were purified as described above without cleavage of the His6 tag to maintain the epitope for western blot analysis. Amylopectin, from potato starch (Sigma) was solubilized by the Roach method (Wang and Roach (2004)) at a concentration of 5 mg/mL. 5 mg of amylopectin was then pre-pelleted via centrifugation at 50,000 rpm for 1.5 hrs at 4° C. to collect only pelletable amylopectin and then resuspended in 0.5 mL binding buffer (50 mM Tris, 150 mM NaCl, pH 7.5, 2 mM DTT). 1 µg of recombinant protein was incubated in amylopectin solution for an hour at 4° C. with rocking. The solution was then centrifuged at 50,000 rpm for 1.5 hrs. Co-sedimentation with amylopectin was measured by centrifuging the samples at 50,000 rpm for 1.5 hrs. All supernatant was removed and protein was precipitated with 4 volumes of acetone stored at −20° C. Precipitated protein was then pelleted via centrifugation at 15,000 rpm for 30 minutes and excess acetone was removed using a SpeedVac concentrator (Savant) at 65° C. for 1.25 hr. Both soluble and pellet fractions were then resuspended in 30 µL RIPA buffer before the addition of 30 µL SDS-PAGE buffer (60 µL total volume for both the soluble and pellet fractions). 15 µL of the pellet and soluble fraction were then resolved via SDS-PAGE and relative concentration of pellet and soluble protein was analyzed by immunoblotting with α-His$_6$ antibody. Quantification of the signal was determined using ImageJ (Abramoff (2004)). The assay was performed □3 times with each protein to determine binding capacity.

Crystal Structure of LSF2 Bound to Maltohexaose and Phosphate

The structure of the *Arabidopsis thaliana* LSF2 glucan phosphatase (residues 79-282, C193S) bound to maltohexaose and phosphate was determined to a resolution of 2.30 Å using molecular replacement with one molecule in the asymmetric unit (FIG. 9A, Table 3).

TABLE 3

| Crystallographic Statistics | | |
|---|---|---|
| Crystal | Δ78-LSF2 C193S - maltohexaose, phosphate | Δ78-LSF2 WT - citrate |
| Data collection | | |
| Space group | P6$_5$22 | P2$_1$2$_1$2 |
| Cell dimensions | | |
| a, b, c (Å) | 92,78, 92.78, 144.94 | 51.82, 99.58, 37.76 |
| α, β, γ (°) | 90, 90, 120 | 90, 90, 90 |
| Wavelength (Å) | 1.00 | 1.00 |
| Resolution range (Å) (highest shell resolution) | 20.0-2.30 (2.38-2.30) | 20-1.65 (1.71-1.65) |
| R$_{merge}$ (highest shell) | 10.8 (39.1) | 6.6 (59.3) |
| I/ σI (highest shell) | 9.0 (2.2) | 20.5 (2.3) |
| Completeness (%) (highest shell) | 94.8 (87.3) | 90.1 (86.3) |
| Redundancy (highest shell) | 3.7 (2.5) | 4.7 (4.7) |
| Refinement | | |
| Resolution (Å) | 2.30 | 1.65 |

TABLE 3-continued

| Crystallographic Statistics | | |
|---|---|---|
| Crystal | Δ78-LSF2 C193S - maltohexaose, phosphate | Δ78-LSF2 WT - citrate |
| No. reflections | 15288 | 20833 |
| $R_{work}/R_{free}$ | 17.3/22.9 | 15.7/19.9 |
| No. atoms | | |
| Protein | 1685 | 1717 |
| Ligand/ion | 251 | 13 |
| Water | 88 | 161 |
| B-factors | | |
| Protein | 41.6 | 13.3 |
| Ligand/ion | 37.6 (phosphate) | 14.5 (citrate) |
| | 70.1 (maltohexaose, active site) | |
| | 59.0 (maltohexaose, site-2) | |
| | 60.7 (maltohexaose, site-3, hex-1) | |
| | 86.1 (maltohexaose, site-3, hex-2) | |
| Water | 49.6 | 31.5 |
| RMSDs | | |
| Bond lengths (Å) | 0.014 | 0.014 |
| Bond angles (°) | 2.1 | 1.7 |
| Ramachandran Plot | | |
| Most favored regions (%) | 97.6 | 98.0 |
| Additional Allowed regions (%) | 2.4 | 2.0 |
| Disallowed regions (%) | 0.0 | 0.0 |

Figure 10:
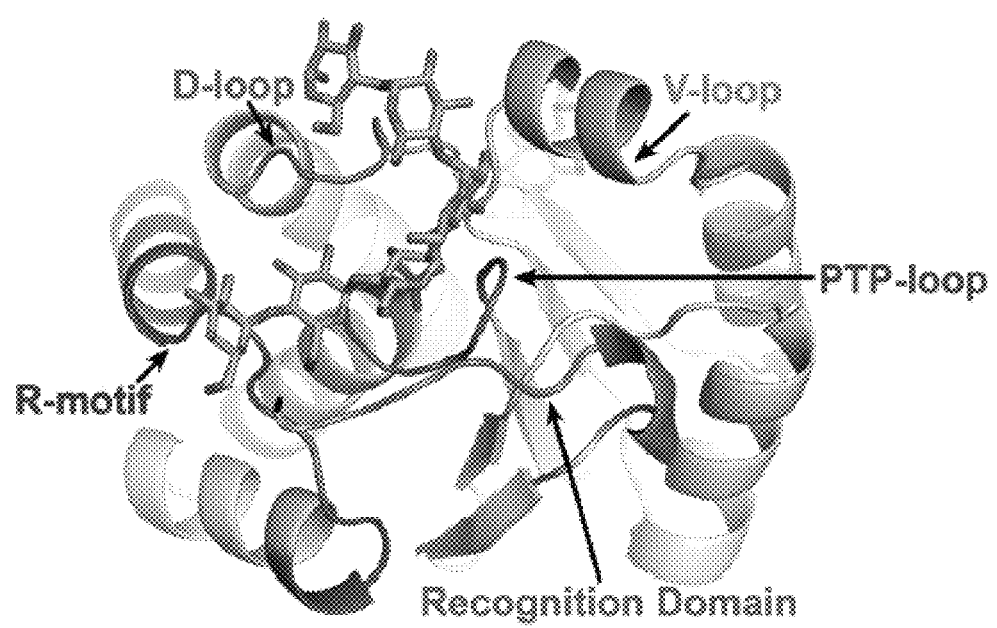
FIG. 10 relates to DSP subdomains in LSF2. Multiple DSP subdomains converge to interact with the maltohexaose chain (green) at the LSF2 active site. DSP subdomains are colored as follows: recognition domain (brown), V-loop (variable loop, pink), D-loop (WPD-loop, orange), PTP-loop (red), and R-motif (blue). The recognition domain consists of residues 83-92 and is located on and amino-terminal to α1. The V-loop consists of residues 132-150 and contains α3 and α4. The D-loop consists of residues 158-163 and is located between β4 and α5. The PTP-loop consists of residues 192-199 and is located between β5 and α6. The R-motif consists of residues 225-249 and contains part of α7 and all of α8.

The LSF2 DSP domain (residues 79-244) possesses a characteristic core PTP fold consisting of a central five-stranded β-sheet region flanked by eight α-helices (FIG. 10). The CT motif (residues 245-282) consists of a loop region culminating in an α-helix that integrally folds into the DSP domain, a characteristic also found in the glucan phosphatase SEX4 (Vander Kooi (2010)). A search for structural homologues of the LSF2 DSP domain (residues 79-244) identifies the DSP domain of *Arabidopsis* SEX4 (residues 90-250, R.M.S.D. 1.1 Å, PDB 3NME (Vander Kooi (2010)) and mouse PTPMT1 (residues 105-256, R.M.S.D. 2.2 Å, PDB 3RGQ (Xiao (2011)) as the structures most similar to LSF2 despite the fact that the LSF2 DSP is only 48% and 17% identical at the amino acid level to the DSP domain of SEX4 and PTPMT1, respectively.

Figure 11:
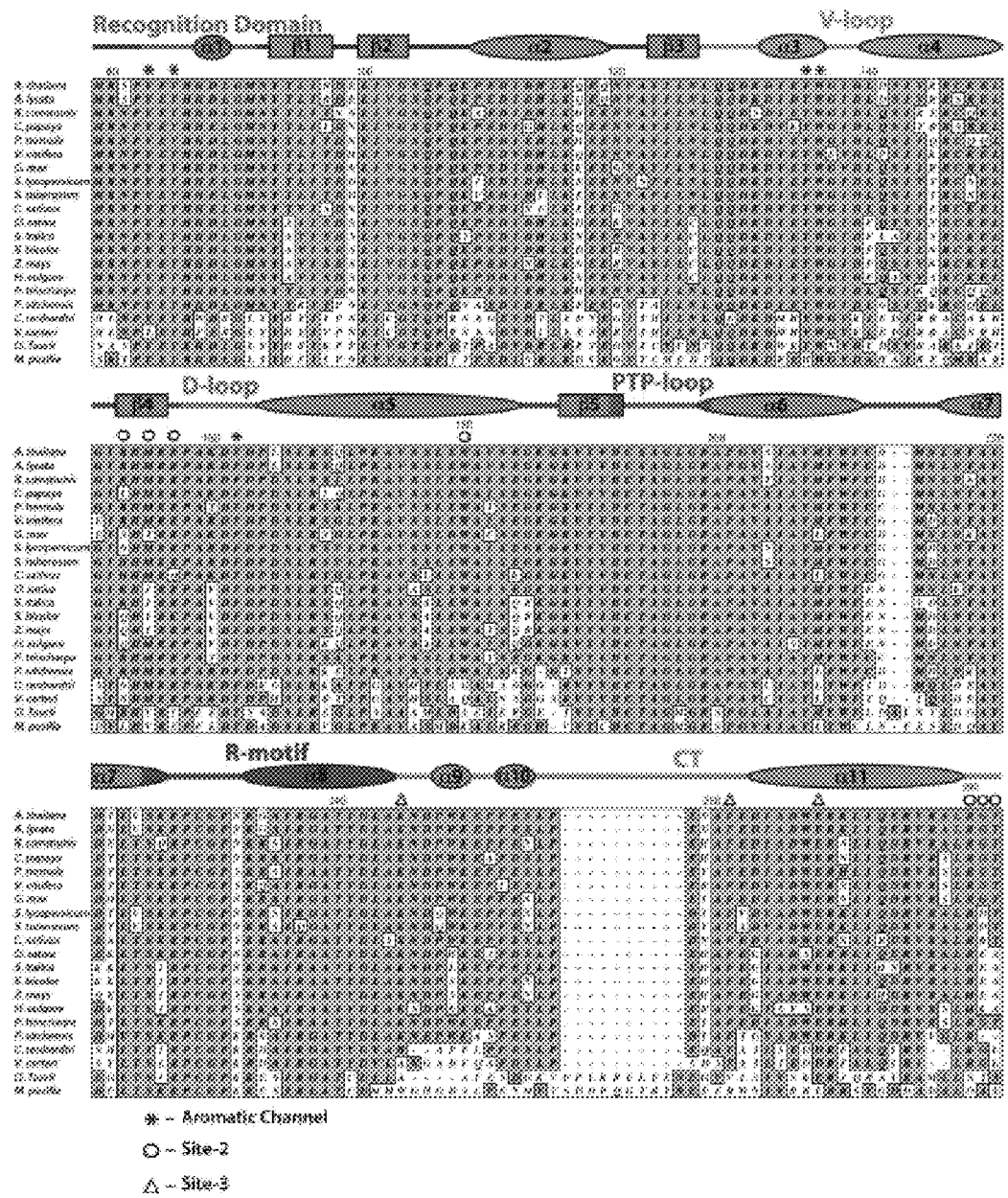
FIG. 11 relates to conservation of LSF2 orthologs and Sequence conservation from 21 genomes containing LSF2 from Kingdom Plantae/Archaeplastida. Primary sequence alignment was produced using ClustalW and $Arabidopsis$ $thaliana$ LSF2 residues 79-282. The chloroplast-Targeting Peptide (cTP) was highly variable between organisms, thus it was excluded for clarity. Secondary structure from the LSF2 structure is shown above. DSP subdomains are depicted and colored according to Supplemental FIG. 1. Residues involved in glucan binding in the active site aromatic channel (asterisk), Site-2 (circle) and Site-3 (triangle) are highlighted.

Maltohexaose is comprised of six glucose moieties with α-1,4-glycosidic linkages, thus it is similar to the unwound helices on the starch granular surface. In the structure, maltohexaose is bound to the LSF2 active site and two distal sites. The LSF2 active site region contains a single maltohexaose chain and phosphate molecule within the catalytic pocket. Multiple conserved DSP active site motifs converge to form an extended active site binding pocket within LSF2 that is ~19 Å long and ~9 Å deep with 511 Å$^2$ contact area (FIG. 9B). These motifs include: a recognition domain from α1 through β1 (83-92), variable (V-)loop from α3 through α4 (132-150), a WPD (D-)loop between β4 and α5 (158-163), a PTP-loop between β5 and α6 (192-199) that contains the LSF2 active site, and an R-motif between α7 and α8 (225-244) (FIGS. 10 and 11).

LSF2 C3-Specificity and Catalytic State

Figure 9D:
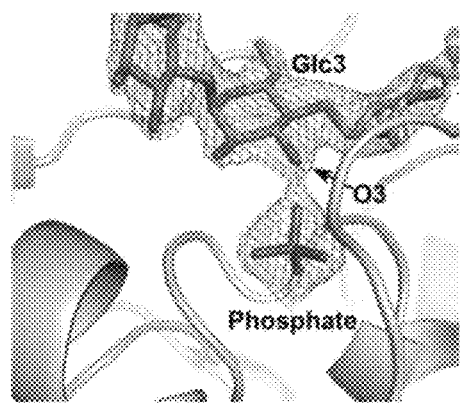
Figure 9E:
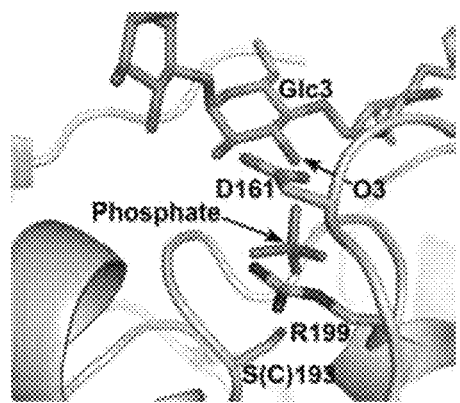
Figure 12:
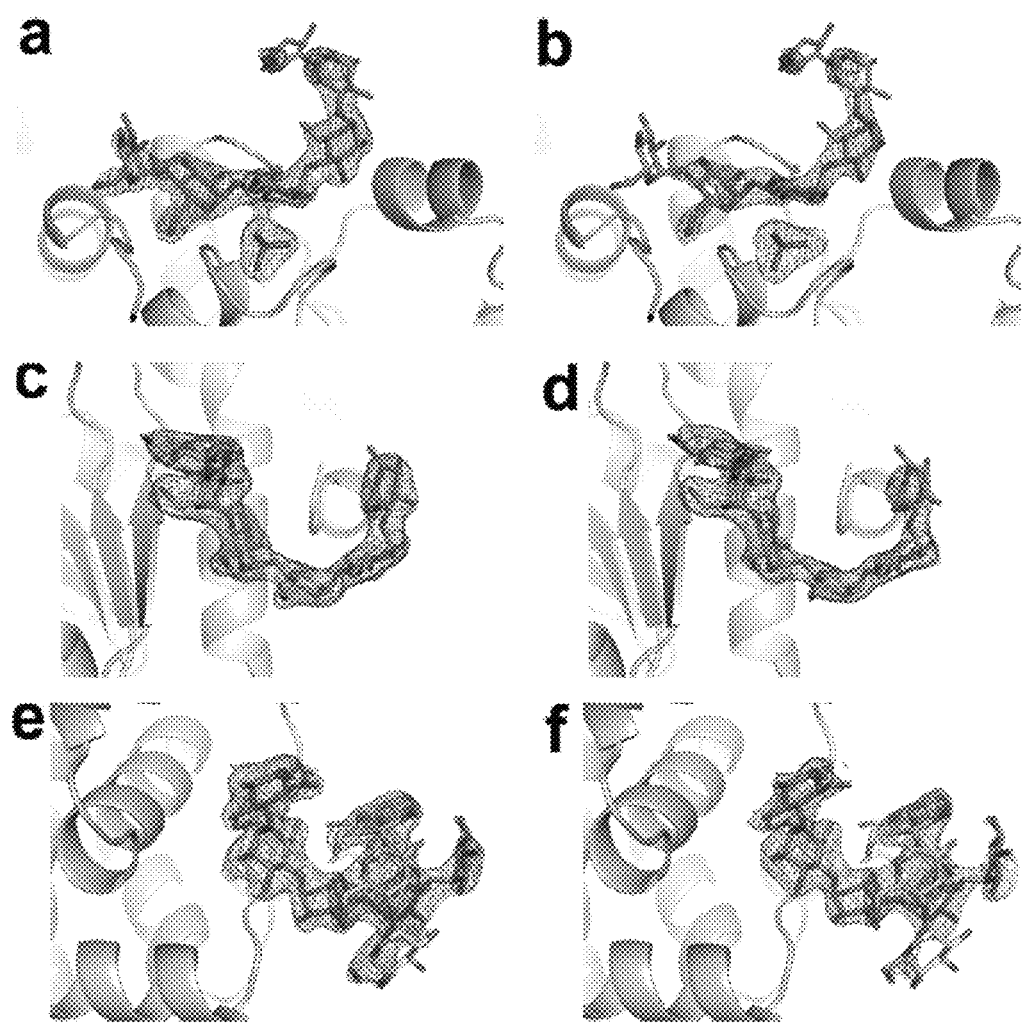
FIG. 12 relates to electron density maps of ligands in LSF2 structure. (A) 2Fo-Fc (a 1.1) and (B) Fo-Fc (σ 2.5) density maps of maltohexaose (green) and phosphate (teal) at the active site. (C) 2Fo-Fc (σ 1.1) and (D) Fo-Fc (σ 2.5) density maps of maltohexaose (cyan) at Site-2. (E) 2Fo-Fc (σ 1.1) and (F) Fo-Fc (σ 2.5) density maps of maltohexaose chains Hex-1 (orange) and Hex-2 (pink) at Site-3.

LSF2 possesses robust activity against starch and displays high specificity for the C3 position, as measured by a $^{33}$P-radiolabeled starch dephosphorylation assay (FIG. 9C) (Santelia (2011)). While both glucan dikinases and glucan phosphatases display strong positional specificity, the basis of this specificity is unclear. The electron density of the maltohexaose in the active site allows clear assignment of glucan chain position and orientation, labeled Glc1-Glc6 from the non-reducing end to the reducing (FIGS. 9D and 12A,B). Strikingly, the O3 group of Glc3 is directly interacting with the phosphate at the LSF2 catalytic site at a distance of 2.4 Å compared to 7.0 Å for the O6 group. Furthermore, the orientation of the PTP catalytic triad ($DX_{30-35}CX_5R$) within LSF2 is proximal to the O3 and phosphate and poised for catalysis of a C3-phosphorylated glucose (FIG. 9E). C193S is located at the base of the active site cleft, 2.5 Å from the nearest phosphate oxygen, and represents the key nucleophilic catalytic residue that covalently attacks the phosphate group during catalysis. R199 is positioned 2.8 Å from the phosphate, and assists in presenting the phosphate of the substrate to the catalytic cysteine. At the top of the active site cleft is the D-loop D161 that participates in catalysis as a general acid/base, forming the reaction intermediate and then assisting in hydrolysis and product expulsion. D161 is located 2.5 Å from the O3 of Glc3 and 3.8 Å from the nearest phosphate oxygen.

Maltohexaose-Phosphate Product Bound at the LSF2 Active Site

Figure 13A:
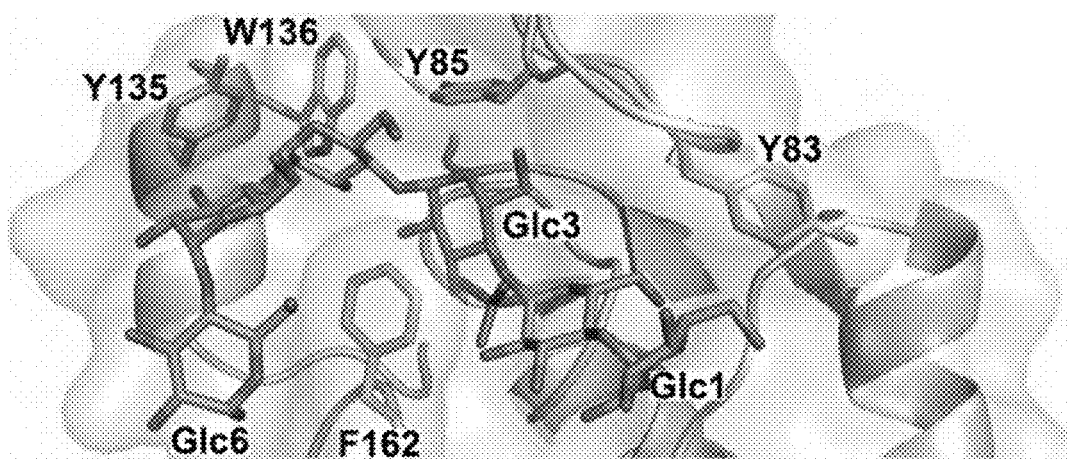

Five highly conserved aromatic residues delineate the boundaries of the extended active site channel, forming extensive interactions with the glucose rings of the maltohexaose chain (FIG. 13A). These five aromatic residues provide the majority of the interface between the LSF2 active site and the substrate. Y83, Y85, Y135 and W136 form one side of the channel and interact with glucose moieties Glc1-5. Y83 and Y85 are located within the recognition domain, directly adjacent to the R-motif and PTP-loop, respectively. Y135 and W136 are both located in the V-loop and form a continuous interaction surface with Y85. F162, located in the D-loop, forms the opposite side of the aromatic channel and interacts with Glc2-6. These glucose moieties form a helical structure around F162 and interact with both faces of the phenylalanine ring. The residues that form the aromatic channel are strictly conserved in all land plants as well as in most single-celled members of Kingdom Plantae, with only one non-conservative substitution (Volvox carteri L83, FIG. 11).

Figure 13B:
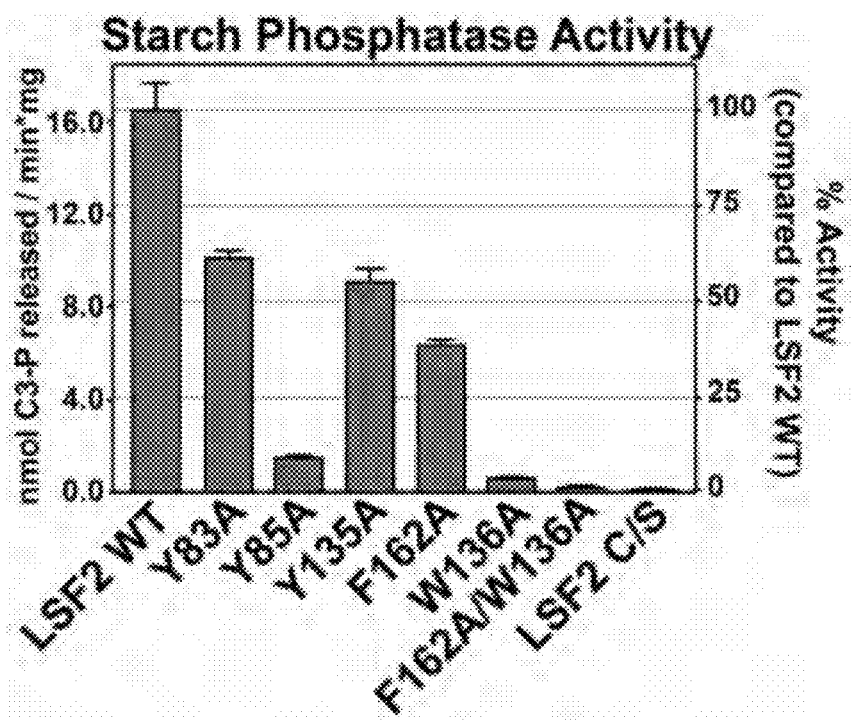
Figure 14:
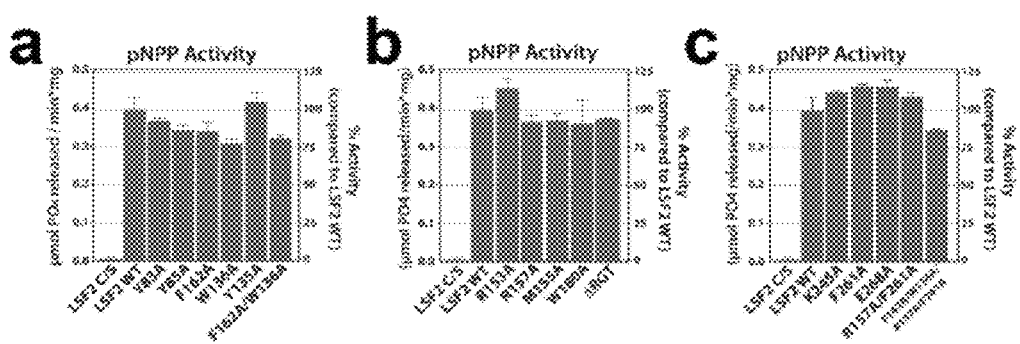
FIG. 14 shows Specific activity of LSF2 and mutants against para-nitrophenyl phosphate (pNPP) pNPP dephosphorylation over time was linear and measured via colorimetric change at 410 nm. Reaction time was 5 minutes. Each bar is the mean±standard deviation of 6 replicates. (A) pNPP activity of aromatic channel mutants. (B) pNPP activity of Site-2 mutants. (C) pNPP activity of Site-3 mutants, including combinatorial Site-2, Site-3 and aromatic channel mutants.

To investigate the functionality of theses aromatic residues, we generated alanine mutants of each channel residue and tested their ability to dephosphorylate starch granules isolated from *Arabidopsis*. Single alanine point mutations of Y83, Y85, Y135, W136, and F162 resulted in a decrease of C3-dephosphorylation by 38-96% (FIG. 13B). Mutation of both sides of the channel (W136A/F162A) resulted in a 99% loss of glucan phosphatase activity. Importantly, the observed decreases in specific glucan phosphatase activity were not due to destabilization of the active site or misfolding of the protein as evidenced by near wild-type phosphatase activity for all mutant proteins towards the generic substrate para-nitrophenyl phosphate (pNPP) (FIG. 14A). Thus, our findings indicate that LSF2 possesses an aromatic channel that forms an extended active site uniquely suited to bind to poly-glucan substrates and necessary for glucan phosphatase activity.

Conformational Changes in the LSF2 Active Site

Figure 13C:
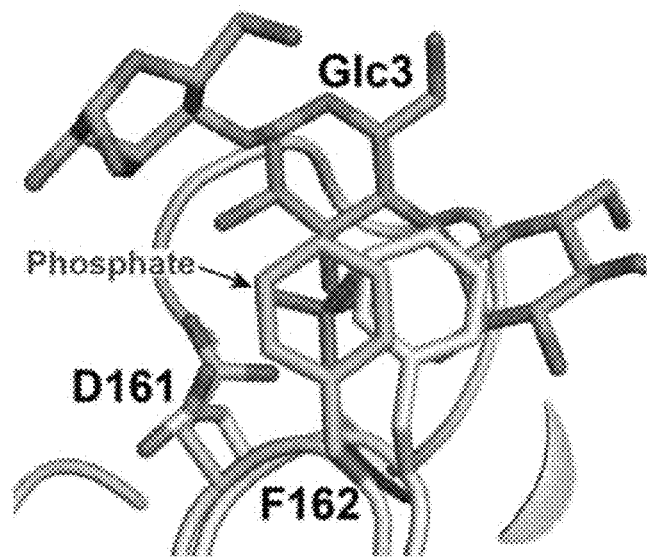
FIG. 13C shows a substrate-dependent positional rearrangement of the D-loop. D-loop residues F162 (aromatic channel) and D161 (catalytic residue) lie between P4 and α5 and undergo significant movement in the maltohexaose/phosphate bound (blue/yellow) versus the unbound (gray/blue) LSF2 structures.
Figure 15:
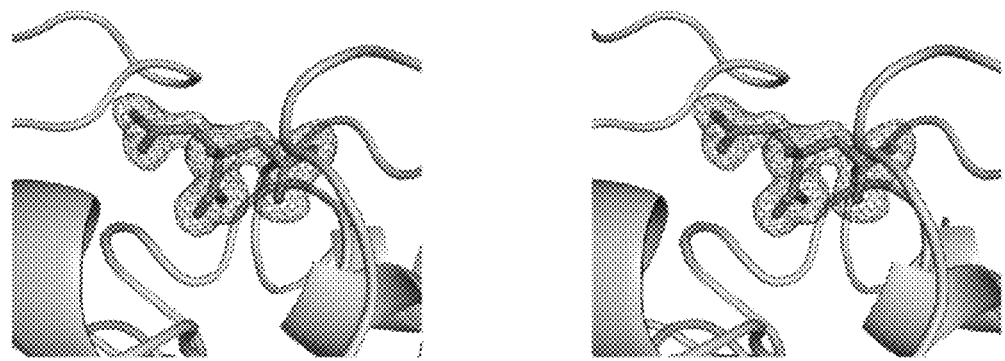
FIG. 15 shows a stereo view of citrate at the LSF2 active site. Ribbon structure of LSF2 with citrate (green) at the active site to a resolution of 1.65 Å with Fo-Fc omit density (σ 3.0) map of citrate at the active site.
Figure 16:
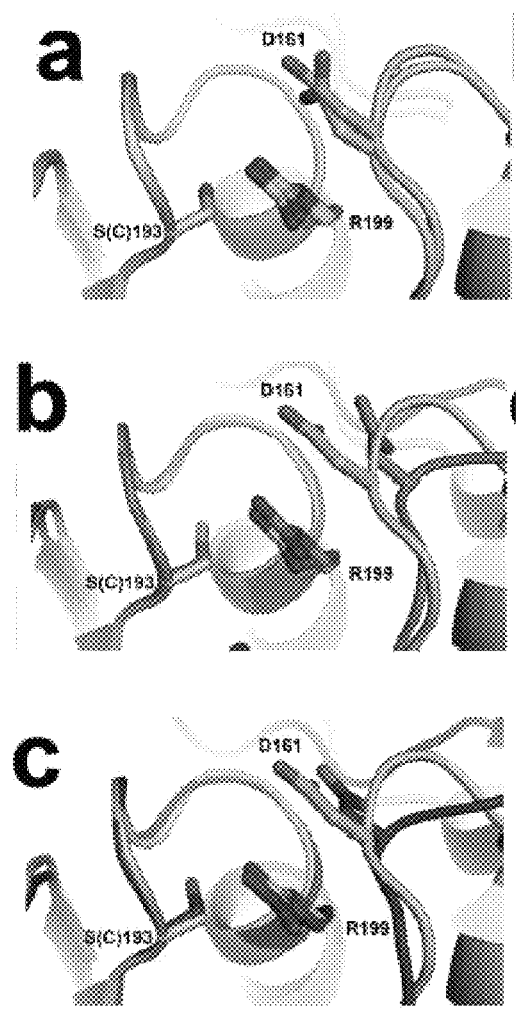
FIG. 16 shows a Structural alignment of DSP catalytic triad of LSF2 Structural alignment with the catalytic triad of the DSPs SEX4 (3NME), VHR (1VHR), and Slingshot-2 (SSH2, 2NT2). LSF2 residues D161, R199, and S193 (catalytically inactive mutant C193S) are labeled. (A) Structural alignment of LSF2 (blue) and SEX4 (green). (B) Structural alignment of LSF2 (blue) and VHR (cyan). (C) Structural alignment of LSF2 (blue) and SSH2 (dark blue).

Intriguingly, one of these key aromatic residues, F162, is found in the D-loop directly after D161 that serves as the general acid/base, discussed above. In fact, F162 makes the most contact of any active site residue with the substrate glucan, (136 $Å^2$, 27% of the total contact area). To compare the catalytic site of glucan-bound and unbound LSF2, we crystallized LSF2 without maltohexaose and determined the structure to a resolution of 1.65 Å using molecular replacement (FIG. 15, Table 3). The glucan-free LSF2 produced a different crystal form and contained one molecule in the asymmetric unit and bound citrate from the crystallization buffer (FIG. 15). The R.M.S.D. of the glucan and citrate-bound DSP domain (residues 79-244) structures is 1.0 Å. A comparison of product-bound and citrate-bound LSF2 structures revealed a substrate-dependent rearrangement of the D-loop architecture upon glucan binding (FIG. 13C). In the product bound structure, the orientations of D161 and F162 are significantly different. The D-loop aromatic residue F162, important for the specific activity of LSF2, interacts with multiple subunits of the glucan and shifts towards the V-loop. This movement is associated with a significant reorientation of the critical general acid/base, residue D161. Comparison of the two structures reveals that the terminal carboxylate of D161 is 3.1 Å closer to the catalytic cysteine and directly in contact with the O3 group of Glc3. To further analyze the position of D161, we compared the LSF2 DSP with structures of the glucan phosphatase SEX4, and the prototypical protein phosphatases VHR (PDB 1VHR (Yuvaniyama (1996)) and SSH-2 (PDB 2NT2 (Jung (2007)). Analysis of the catalytic triad from each of these structures reveals that the substrate-bound orientation of LSF2 D161 is in a catalytically competent orientation only in the product bound structure (FIG. 16). Thus, LSF2 undergoes a substrate-induced conformational change with the LSF2 product bound form ideally positioned for catalysis of an O3 phosphorylated glucan substrate.

Most DSPs possess a short chain hydrophilic reside, S/T/N/H, at the +1 residue from the general acid/base aspartate (Vander Kooi (2010)). However, F162 is invariant in LSF2 and the corresponding residue is also strictly conserved in SEX4, F167. We previously demonstrated that mutating SEX4 F167 to a short chain hydrophilic residue (F167S) resulted in a 50% decrease in the glucan/pNPP phosphatase activity of SEX4 F167S (Vander Kooi (2010)). Cumulatively, these data demonstrate an important role for D-loop movement in order to correctly position the catalytic triad and maximize glucan phosphatase activity.

Non-Catalytic Glucan Binding Sites

Figure 17A:
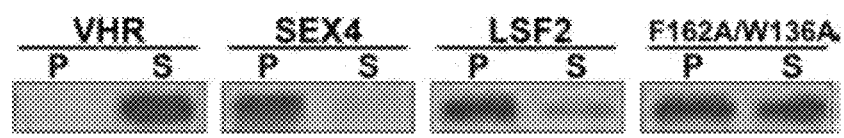
FIGS. 17A and 18B show LSF2 glucan binding sites.

Glucan phosphatases were originally defined as enzymes that contain both a DSP and CBM domain, and the CBM has been shown to be critical for endogenous substrate binding and biological activity (Gentry (2007), Gentry and Pace (2009)). Because LSF2 lacks a CBM the nature of its substrate binding ability has been unclear. Therefore, we investigated LSF2 glucan binding to amylopectin. LSF2 was incubated with amylopectin, the amylopectin was then pelleted by ultracentrifugation. Proteins in the pellet (P) and supernatant (S) were separated by SDS-PAGE, and visualized by Western analysis. The prototypical protein phosphatase VHR does not bind amylopectin and is found in the supernatant whereas the prototypical glucan phosphatase SEX4 possesses robust glucan binding and is largely in the pellet (FIG. 17A). LSF2 also robustly binds amylopectin, and similar to SEX4 is largely in the pellet. Next we sought to define how mutations in the aromatic channel affect LSF2 glucan binding. The LSF2 W136A/F162 Å mutant, which has a 99% decrease in specific glucan phosphatase activity, shows only a moderate (32%) decrease in amylopectin binding (FIG. 17A). This suggests that while the active site is necessary for glucan phosphatase activity, other regions primarily determine substrate binding. These data are consistent with LSF2 containing additional glucan-binding sites distinct from the active site aromatic channel.

Figure 17B:
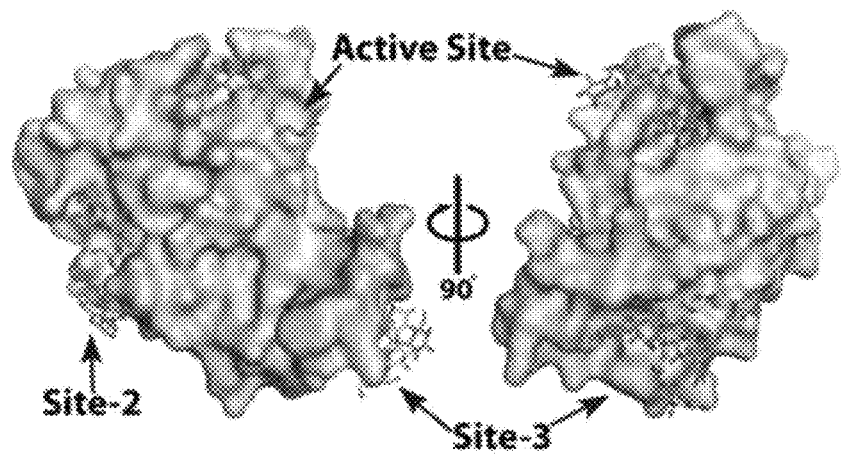
FIG. 17B is a surface model of LSF2 showing DSP domain (blue) and CT motif (green). Maltohexaose chains at the active site (green), Site-2 (cyan), and Site-3 (orange, pink) are shown.

Indeed, the maltohexaose-bound LSF2 structure revealed two additional glucan binding sites >20 Å from the active site (FIG. 17B). Thus, we hypothesized that one or both of these additional glucan-binding sites could functionally replace a CBM domain and be critical for the biological activity of LSF2.

Figure 18A:
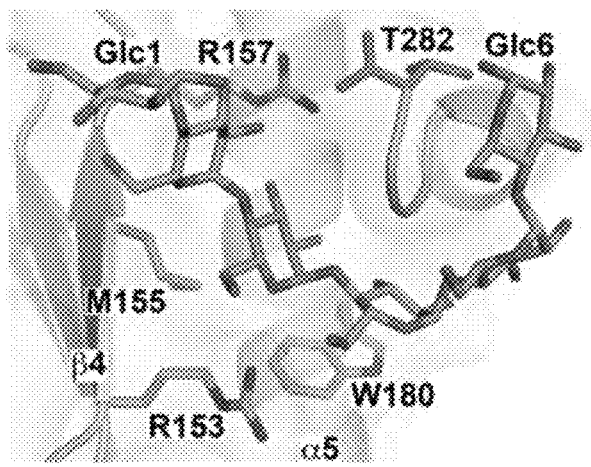
Figure 18B:
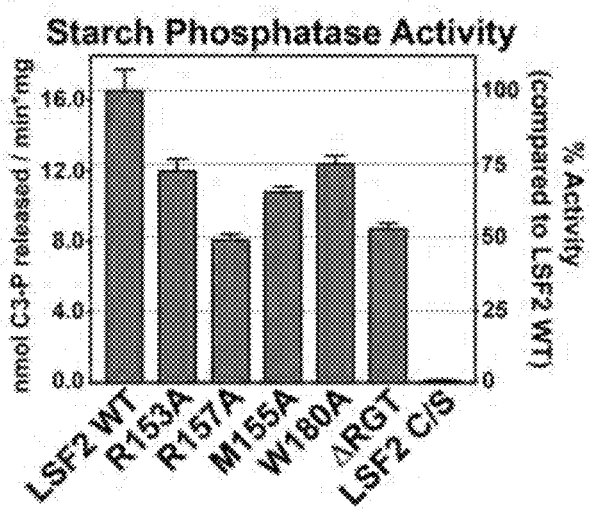
Figure 18C:
FIG. 18C is an amylopectin binding assay of Site-2 mutant R157 Å was performed in a similar manner as described in FIG. 17A. LSF2 R157 Å was co-sedimented with amylopectin and found in the pellet (P) and supernatant (S).

One maltohexaose chain is located in a binding pocket (Site-2) formed by residues from the DSP domain and CT-motif on the opposite side of the V-loop ~21 Å from the active site. The maltohexaose chain makes extensive contacts (391 $Å^2$) with residues in β4 and α5 of the DSP as well as the carboxy-terminus of the CT-domain (FIGS. 12C,D and 19A). The maltohexaose chain wraps around the CT loop, forming hydrogen bonds with R153 and R157 and van der Waals contact with W180 and M155. As with the active site residues, Site-2 residues are highly conserved in LSF2 orthologs (FIG. 11). To determine the effect of Site-2 glucan binding on LSF2 activity, we tested the ability of alanine point mutants as well as a C-terminal truncation to dephosphorylate starch granles. Alanine mutations of W180, M155, R153 and R157 resulted in decreases of specific glucan phosphatase activity of 24-50% (FIG. 18B). Truncation of the three carboxy-terminal residues (ARGT) decreased activity by 46%. All mutant proteins maintained near wild-type pNPP activity indicating that the observed effects are specific (FIG. 14B). While mutation of Site-2 resulted in a substantial decrease in glucan phosphatase activity, we also investigated the effect of Site-2 mutants on substrate binding. We tested the ability of LSF2 R157A, which shows the greatest reduction in specific activity, to bind amylopectin and found that it displayed a substantial (64%) decrease in amylopectin-binding (FIG. 18C). This decrease was markedly greater than that observed for the W136A/F162A active site mutant (FIG. 17A). These data demonstrate that Site-2 functions as a glucan-binding interface and that this binding site is important for the biological activity of starch dephosphorylation by LSF2.

Figure 19A:
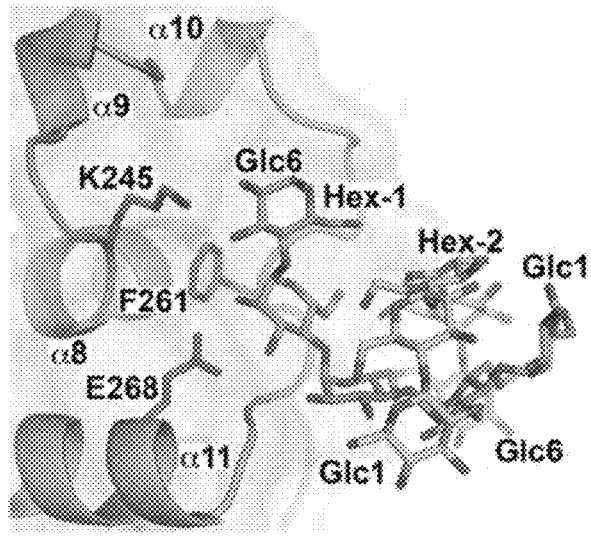
Figure 19B:
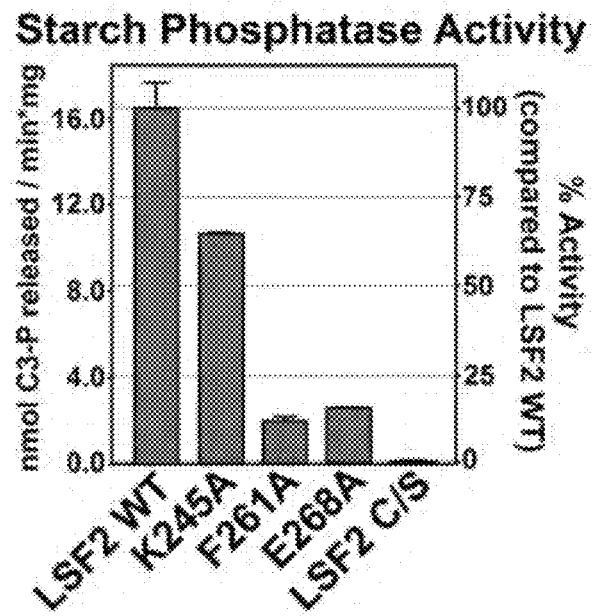
FIG. 19B shows specific activity of Site-3 mutants against the C3-position of *Arabidopsis* starch granules. Phosphate-free starch from gwd-deficient plants (Yu (2001)) was purified and pre-labeled at the C3- or C6-position with $^{33}$P as in FIG. 9C. The labeled starch was then incubated with LSF2 WT or LSF2 Site-3 mutants and starch dephosphorylation was measured via release of $^{33}$P. The reaction time was 5 minutes. Each bar is the mean±standard deviation of 6 replicates. Mutated residues are marked with a triangle in FIG. 20.
Figure 19C:
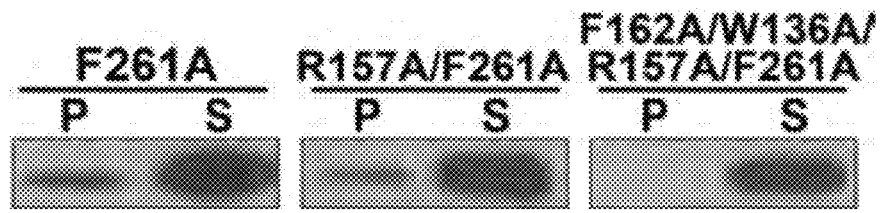
Figure 20:
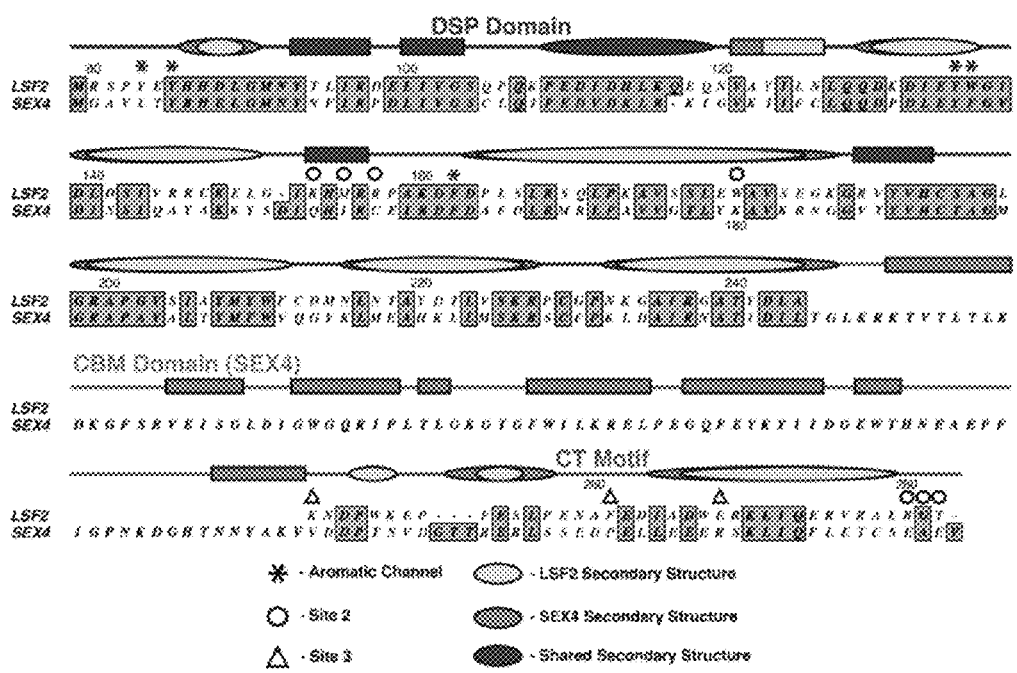

Two additional maltohexaose chains were found in a binding pocket (Site-3) formed by the CT loop region ~23 Å from the active site. Five glucose moieties from two maltohexaose chains (Hex-1 and Hex-2) could be resolved (FIGS. 12E,F and 19A). The two chains form a helical structure, reminiscent of an amylopectin helix, with a contact area of 338 $Å^2$. LSF2 primarily interacts with Hex-1, forming hydrogen bonding interactions with K245 and E268 and van der Waal's interactions with F261. As with the active site and Site-2 residues, Site-3 residues are highly conserved in LSF2 orthologs (FIG. 11). To determine the effect of Site-3 glucan binding on LSF2 activity, we tested the ability of alanine point mutants to dephosphorylate starch granules. Alanine mutations of E268, K245, and F261 resulted in decreases of specific glucan phosphatase activity of 35-87% (FIG. 19B). All mutant proteins maintained near wild-type pNPP activity indicating that the observed effects are specific (FIG. 14C). Similar with Site-2, we also investigated the effect of Site-3 on substrate binding. We found that the Site-3 mutant F261A, which shows the greatest reduction in specific activity, showed the most dramatic (73%) decrease in amylopectin-binding (FIG. 19C). In comparison to Site-2, Site-3 mutants showed greater effects on both substrate binding and specific glucan phosphatase activity.

To determine the contribution of the individual glucan binding sites to the overall binding of LSF2, we generated combination mutants. The combination of Site-2 and Site-3 mutations, R157A/F261A, displayed an even more dramatic (87%) decrease in amylopectin binding, but still retained slight binding (FIG. 19C). Only a mutant combining all three sites, F162A/W136A/R157A/F261A, resulted in a protein that possesses no detectable glucan binding (FIG. 19C). Thus, each of the three glucan-binding sites contributes to substrate binding and none of the sites are individually sufficient for wild-type levels of glucan binding. Taken together, these data demonstrate that rather than requiring a scaffold protein or CBM, LSF2 possesses three glucan binding sites in its DSP domain that are each critical for its ability to bind glucans and function as a specific glucan phosphatase.

Phosphatases dephosphorylate each of the four organic macromolecules: proteins, lipids, nucleic acids, and carbohydrates. While previous studies have defined the structural bases of phosphatase activity with proteins, lipids, and nucleic acids, the basis for phosphatase-glucan interaction was previously unknown. Here, we examined the structural and biochemical basis of glucan phosphatase activity by determining the crystal structure of LSF2, providing the first detailed insights into the mechanism of this important class of enzymes.

At the LSF2 active site, an integrated network of aromatic residues forms an extended binding pocket that allows specific glucan interaction and dephosphorylation. While these aromatic residues are within the core DSP domain, in each case they are uniquely suited to promote phospho-glucan binding. Conservation of aromatic residues in the active site between glucan phosphatases suggests that this is a key general characteristic differentiating glucan phosphatases from other phosphatases. It is particularly notable that both LSF2 and the previously determined SEX4 structure possess an α-helical V-loop containing conserved aromatic residues, Y135 and W136 in the LSF2 V-loop (Vander Kooi (2010)). These residues are integral for LSF2 glucan binding and dephosphorylation and form the basis of the conserved theme of an aromatic channel within the active site of glucan phosphatases. In contrast, the V-loop of PTPs and DSPs are historically defined by their lack of secondary structure and highly variable length (Alonso (2003)). Phospho-tyrosine phosphatases contain longer V-loops when compared to phospho-serine/threonine phosphatases in order to generate a deeper binding pocket that accommodates the longer phospho-tyrosine. However, in each case the V-loop is indeed a loop (Alonso (2003), Tonks (2006)). Thus, the glucan phosphatase structured V-loop appears to be a defining characteristic of this phosphatase class.

Aromatic-glucose stacking interactions are a central structural element for CBMs (Boraston (2004), Machovic and Janecek (2006)), and are found in the catalytic channel of glycosyl hydrolases (Robert (2005), Koropatkin and Smith (2010)). However, a similar glucan-aromatic channel interface had not been previously observed in any phosphatase. Our crystallography data revealed that the LSF2 active site maintains interactions with all 6 glucose moieties on the maltohexaose chain, thus indicating that the active site of LSF2 combines both a DSP active site and glucan-binding platform.

Indeed, we identified a link between LSF2 substrate binding and catalysis mediated by residue F162. In addition to being a part of the active site aromatic channel, F162 is located at the +1 position from the catalytic triad residue D161. Rotation of these residues upon glucan binding is required for the correct catalytic positioning of D161. This connection suggests an inherent mechanism for phosphate recognition that is tied directly to the architecture of the glucan phosphatase aromatic channel. It is important to note that this may be a general feature of this enzyme class since this residue is conserved as an aromatic/long chain hydrophobic residue in all known glucan phosphatase whereas other phosphatases typically possess short-chain hydrophilic residues at this position (Vander Kooi (2010)).

Despite similarities with other glucan phosphatases, LSF2 is in fact unique among known glucan phosphatases in that the enzyme functions independent of a CBM. There has been debate as to whether or not other functionality or possibly bridging proteins are required for the glucan phosphatase activity of LSF2 (Comparot-Moss (2010), Santelia (2011)). However, our data clearly establish for the first time that LSF2 utilizes three glucan binding sites located in the phosphatase domain for carbohydrate binding. The central function attributed to CBMs is substrate localization, and our data demonstrate that the non-catalytic glucan binding sites identified in the LSF2 structural data adopt this functionality. Mutations of Site-2 and Site-3, the two binding sites located away from the active site, result in dramatic decreases in LSF2 glucan binding and dephosphorylation, similar to decreases observed for CBM mutants of SEX4 and laforin (Ganesh (2004), Wang and Roach (2004), Gentry (2007)). It should be noted that Site-2 and Site-3 both utilize residues from the glucan phosphatase-specific CT motif (Vander Kooi (2010), Santelia (2011)). Thus, this unique elaboration on the core phosphatase domain provides novel functionality.

Carbohydrate active enzymes (CAZymes) as defined by the CAZy database (http://www.cazy.org) are a diverse collection of enzymes that synthesize and degrade an extremely heterogeneous group of complex carbohydrates and glycoconjugates (Cantarel (2009)). These enzymes cover >250 protein families including glycoside hydrolases, glycosyltransferases, polysaccharide lyases, carbohydrate esterases, and non-enzymatic proteins that contain a CBM (Cantarel (2009)). A CBM is a contiguous amino acid sequence with a conserved tertiary fold that possesses carbohydrate-binding ability and is contained within a carbohydrate-modifying enzyme (Coutinho and Henrissat (1999), Boraston (2004), Machovic and Janecek (2006); Cantarel (2009)). Many of the enzymes that synthesize and degrade carbohydrates utilize a CBM to bind their carbohydrate substrate and then enzymatically act on the carbohydrate via a distinct catalytic module. This model of a binding domain and enzymatic domain is true for the other identified glucan phosphatases (Worby (2006), Gentry (2007), Kotting (2009), Vander Kooi (2010)). Indeed, the glucan phosphatases were originally defined as any protein containing a phosphatase domain and a CBM (Gentry (2007)). While LSF2 is a carbohydrate-modifying enzyme that binds carbohydrates, it does not contain a classical CBM and is not classified under the CAZy classification.

Alternatively, LSF2 utilizes a glucan binding architecture referred to as secondary binding sites (SBSs) (Robert (2005), Bozonnet (2007), Cuyvers (2011)). SBSs are an emerging theme found in some glycoside hydrolases (GHs) (Cuyvers (2011)). Many GHs possess one or more CBM, but recent structural studies have identified a subset of GHs that contain both a CBM and SBSs, such as SusG (Koropatkin and Smith (2010)), or that only possess SBSs, such as barley α-amylase (Kadziola (1998), Robert (2005)), human salivary and pancreatic α-amylase (Pagan and Qian (2003), Ragunath (2008)), and yeast glucoamylase (Sevcik (2006)). Indeed, the two SBSs of barley α-amylase, which are remote from its glucan-binding active site, are directly involved in substrate binding and hydrolysis and these two sites act synergistically (Nielsen (2009)).

Figure 21:
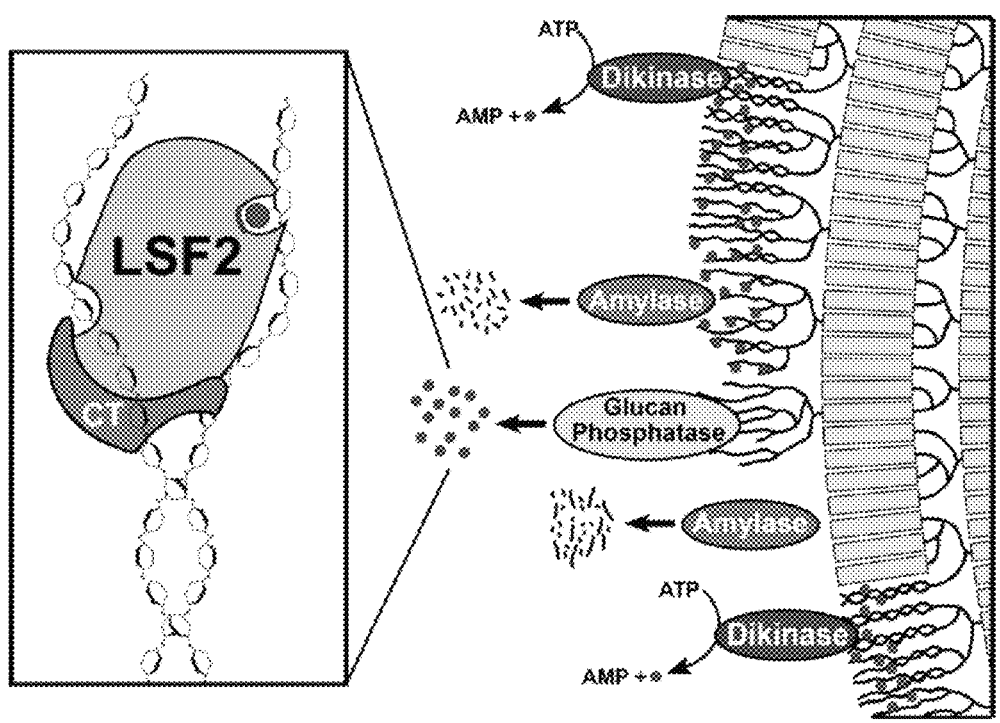
FIG. 21 shows a proposed model of reversible phosphorylation at the starch granular surface during breakdown (modified from (Streb and Zeeman, 2013)). At night, starch is phosphorylated (red circles) by glucan dikinases, leading to solubilization of the outer starch granules via unwinding of amylopectin helices (gray bars). Amylopectin is then hydrolyzed by amylases into maltose and malto-oligosaccharides. However, these amylases cannot completely degrade phosphorylated starch. Therefore, glucan phosphatases must remove phosphate from partially degraded amylopectin chains. The outer starch surface is then fully degraded by amylases into malto-oligosaccharides, and the cycle is reset so that the next starch layer can be phosphorylated and degraded. The inset box illustrates a model of LSF2-glucan interaction. Amylopectin helices are comprised of two α-1,4-glycosidic linked chains that are partially unwound at their non-reducing ends due to phosphorylation. LSF2 interacts with starch via multiple binding sites: the LSF2 active site (highlighted in red) interacts with the C3-phosphorylated glucose moiety through coordination of the aromatic channel with six glucose units, Site-2 also interacts with six glucose moieties via hydrogen bonding and van der Waals contacts at an interface between the LSF2 DSP domain (blue) and the carboxy-terminal motif (CT, green), and Site-3 interacts with two helical-like glucan chains through interactions with the CT motif.

These results establish that LSF2 independently binds and dephosphorylates starch. As starch is a complex, insoluble substrate, the presence of multiple glucan binding interfaces may permit LSF2 to uniquely engage the complex multivalent glucan surface of its endogenous substrate. Indeed, the combined-site mutants (R157A/F261 Å and F162A/W136A/R157A/F261A) show additive effects, implying that the sites function together. This suggests a model whereby starch binding involves the engagement of longer or multiple glucan chains by the three glucan binding sites on LSF2 (FIG. 21). Moreover, the helical glucan chains at Site-3 are reminiscent of amylopectin suggesting LSF2 may interact with complex starch granules with distinct helical characteristics. The functional significance of secondary binding sites in glycosyl hydrolases has been extensively reviewed and various additional functions have been postulated, including substrate disruption, allosteric regulation, enhancing processivity, and relaying of reaction products (Cuyvers (2011)). On-going studies will examine in more detail the specific role and possible cooperativity of these additional glucan binding sites of LSF2.

These data also give a clearer picture of the role of glucan phosphatases in the cyclical starch degradation process. The glucan dikinases phosphorylate the outer glucose moieties of starch at the C6- and C3-positions, resulting in amylopectin helix unwinding and local solubilization. These events allow α- and β-amylases as well as isoamylases to access the outer glucans and release maltose and malto-oligosaccharides. However, β-amylase activity is inhibited when a phosphate group is reached. The glucan phosphatases bind and dephosphorylate the phospho-glucans to allow further amylolytic activity and a resetting of the starch degradation cycle (FIG. 21). The coordinated phosphorylation of starch glucose at the C6- and C3-position is the central signaling event orchestrating starch breakdown (Blennow and Engelsen (2010), Kotting (2010), Streb and Zeeman (2013)). The recent characterization of SEX4 and LSF2 illustrates that plants utilize a two-enzyme system for phosphate removal, permitting complete starch catabolism. Our structures reveal the basis for the glucan binding and C3-specificity of LSF2. Determination of additional glucan phosphatase structures will reveal further insights into the mechanism of activity and specificity of glucan phosphatases. In particular, it will be interesting to determine if the presence of a CBM domain in other family members not only contributes to substrate binding but also to position-specific function.

As the central regulatory event governing starch breakdown, modulation of reversible phosphorylation has the potential to increase starch yields and produce starches with novel physicochemical properties, thus enhancing manufacturing of feedstock for both food and non-food applications (Santelia and Zeeman (2010)). Starch is used in countless applications, many of which require chemical and physical modifications to improve and diversify its functionality (Blennow (2002), Santelia and Zeeman (2010)). Phosphorylation is the only known natural modification of starch and highly phosphorylated starches have many attractive characteristics, including increased hydration status (Muhrbeck and Eliasson (1991)), decreased crystallinity (Muhrbeck and Eliasson (1991)), and improved freeze-thaw stability, viscosity and transparency (Blennow A (2001)). *Arabidopsis* plants lacking LSF2 activity display increased C3-phosphorylated starch without adverse effects on plant growth (Santelia (2011)). Genetic manipulation of LSF2 could therefore represent a new means to produce starch with higher phosphate content, particularly in cereal crops containing virtually no covalently bound phosphate (Blennow (2000)). This possibility is further realized through a more complete understanding of LSF2 structure and function that can be used to inform the engineering of glucan phosphatases to alter their functionality for industrial starch processing, particularly in light of disparities between C6- and C3-contributions to starch superstructure. Structural insights into the unique mechanism of LSF2 are fundamental to our understanding of starch catabolism and ultimately harnessing starch as a biomolecule with diverse applications.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

REFERENCES

Throughout this document, various references are mentioned. All such references, including those listed below, are incorporated herein by reference.
1. Abramoff, M. D., Magalhaes, P. J., and Ram, S. J. (2004). Image Processing with ImageJ. Biophotonics International 11, 36-42.
2. Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., and Zwart, P. H. (2010). PHENIX: a comprehensive Python-based system for macromolecular structure solution. Acta Crystallogr D Biol Crystallogr 66, 213-221.
3. Alonso, A., Rojas, A., Godzik, A., and Mustelin, T. (2003) The dual-specific protein tyrosine phosphatase family, Springer, Berlin.
4. Ball, S., Colleoni, C., Cenci, U., Raj, J. N., and Tirtiaux, C. (2011) J Exp Bot 62, 1775-1801.
5. Ballicora, M. A., Frueauf, J. B., Fu, Y., Schurmann, P., and Preiss, J. (2000) J Biol Chem 275, 1315-1320.
6. Balmer, Y., Koller, A., del Val, G., Manieri, W., Schurmann, P., and Buchanan, B. B. (2003) Proc Natl Acad Sci USA 100, 370-375.
7. Balmer, Y., Vensel, W. H., Cai, N., Manieri, W., Schurmann, P., Hurkman, W. J., and Buchanan, B. B. (2006) Proc Natl Acad Sci USA 103, 2988-2993.
8. Barker, K. (2005) At the Bench: A Laboratory Navigator, Cold Spring Harbor Laboratory Press, Cold Spring Harbor, N.Y.
9. Barrientos, M. (2012) Index Mundi.
10. Baunsgaard, L., Lutken, H., Mikkelsen, R., Glaring, M. A., Pham, T. T., and Blennow, A. (2005). A novel isoform of glucan, water dikinase phosphorylates pre-phosphorylated alpha-glucans and is involved in starch degradation in Arabidopsis. Plant J 41, 595-605.
11. Bhatnagar, A., Chinnasamy, S., Singh, M., and Das, K. C. (2011) Applied Energy 88, 3425-3431.
12. Blaser, B. (2010) Career Trends: Building Relationship. Science/AAAS, Washington, D.C.
13. Blaser, B. (2010) Step by Step: Your Career from Undergrad to Postdoc. Science/AAAS, Washington, D.C.
14. Blaser, B., Gosling, P., Noordam, B., Bonetta, L., Carpenter, S., Vastag, B., and Austin, J. (2009) Careers Away from the Bench. in Career Trends from Science Careers (Blaser, B. ed., HighWire Press, Palo Alto, Calif.
15. Blennow A, B.-S. A., Bauer R. (2001). Amylopectin aggregation as a function of starch phosphate content studied by size exclusion chromatography and on-line refractive index and light scattering. International Journal of Biological Macromolecules 28, 409-420.
16. Blennow, A., and Engelsen, S. B. (2010) Trends Plant Sci 15, 236-240 Blennow, A., and Engelsen, S. B. (2010) Trends Plant Sci 15, 236-240.
17. Blennow, A., and Engelsen, S. B. (2010). Helix-breaking news: fighting crystalline starch energy deposits in the cell. Trends Plant Sci 15, 236-240.
18. Blennow, A., Bay-Smidt, A. M., Leonhardt, P., Bandsholm, O., and Madsen, M. H. (2003) Starch-Stárke 55, 381-389.
19. Blennow, A., Bay-Smidt, A. M., Olsen, C. E., and Moller, B. L. (2000). The distribution of covalently bound phosphate in the starch granule in relation to starch crystallinity. Int J Biol Macromol 27, 211-218.
20. Blennow, A., Nielsen, T. H., Baunsgaard, L., Mikkelsen, R., and Engelsen, S. B. (2002). Starch phosphorylation: a new front line in starch research. Trends Plant Sci 7, 445-450.
21. Bonetta, L. (2010) The Postdoc Experience: Taking A Long Term View. in Career Advice from Science Careers, HighWire Press, Palo Alto, Calif.
22. Boraston, A. B., Bolam, D. N., Gilbert, H. J., and Davies, G. J. (2004). Carbohydrate-binding modules: fine-tuning polysaccharide recognition. Biochem J 382, 769-781.
23. Bozonnet, S., Jensen, M. T., Nielsen, M. M., Aghajari, N., Jensen, M. H., Kramhoft, B., Willemoes, M., Tranier, S., Haser, R., and Svensson, B. (2007). The 'pair of sugar tongs' site on the non-catalytic domain C of barley alpha-amylase participates in substrate binding and activity. FEBS J 274, 5055-5067.
24. Buleon, A., Colonna, P., Planchot, V., and Ball, S. (1998). Starch granules: structure and biosynthesis. Int J Biol Macromol 23, 85-112.
25. Cantarel, B. L., Coutinho, P. M., Rancurel, C., Bernard, T., Lombard, V., and Henrissat, B. (2009). The Carbohydrate-Active EnZymes database (CAZy): an expert resource for Glycogenomics. Nucleic Acids Res 37, D233-238.
26. Carrillo, N., Ceccarelli, E., and Roveri, O. (2010) Biotechnology & genetic engineering reviews 27, 367-382.
27. Caspar, T., Lin, T. P., Kakefuda, G., Benbow, L., Preiss, J., and Somerville, C. (1991). Mutants of Arabidopsis with altered regulation of starch degradation. Plant Physiol 95, 1181-1188.
28. Ceccarelli, E. A., Carrillo, N., and Roveri, O. A. (2008) Trends in biotechnology 26, 117-118.
29. Chen, C. Y., Yeh, K. L., Aisyah, R., Lee, D. J., and Chang, J. S. (2011) Bioresour Technol 102, 71-81.
30. Chisti, Y. (2007) Biotechnol Adv 25, 294-306 Chisti, Y. (2007) Biotechnol Adv 25, 294-306.
31. Chisti, Y. (2008) Trends in biotechnology 26, 126-131 Chisti, Y. (2008) Trends in biotechnology 26, 126-131.
32. Comparot-Moss, S., Kotting, O., Stettler, M., Edner, C., Graf, A., Weise, S. E., Streb, S., Lue, W. L., MacLean, D., Mahlow, S., Ritte, G., Steup, M., Chen, J., Zeeman, S. C., and Smith, A. M. (2010) Plant Physiol 152, 685-697.
33. Comparot-Moss, S., Kotting, O., Stettler, M., Edner, C., Graf, A., Weise, S. E., Streb, S., Lue, W. L., MacLean, D., Mahlow, S., Ritte, G., Steup, M., Chen, J., Zeeman, S. C., and Smith, A. M. (2010). A putative phosphatase, LSF1, is required for normal starch turnover in Arabidopsis leaves. Plant Physiol 152, 685-697.
34. Copeland, L., Blazek, J., Salman, H., and Tang, M. C. (2009) Food Hydrocolloids 23, 1527-1534.
35. Coutinho, P. M., and Henrissat, B. (1999). Carbohydrate-active enzymes: an integrated database approach. Recent Advances in Carbohydrate Bioengineering, 3-12.
36. Cuyvers, S., Dornez, E., Delcour, J. A., and Courtin, C. M. (2011). Occurrence and functional significance of secondary carbohydrate binding sites in glycoside hydrolases. Crit Rev Biotechnol.
37. Davis, A. (2006) Medicines By Design. (Services, U.S. D. o H. a. H. ed., U.S. Department of Health and Human Services, Washington, D.C.
38. Davis, I. W., Leaver-Fay, A., Chen, V. B., Block, J. N., Kapral, G. J., Wang, X., Murray, L. W., Arendall, W. B., 3rd, Snoeyink, J., Richardson, J. S., and Richardson, D. C. (2007). MolProbity: all-atom contacts and structure validation for proteins and nucleic acids. Nucleic Acids Res 35, W375-383.

39. Delcour, J. A., Bruneel, C., Derde, L. J., Gomand, S. V., Pareyt, B., Putseys, J. A., Wilderjans, E., and Lamberts, L. (2010) Annu Rev Food Sci Technol 1, 87-111.

40. Dukhande, V. V., Rogers, D. M., Roma-Mateo, C., Donderis, J., Marina, A., Taylor, A. O., Sanz, P., and Gentry, M. S. (2011) PLoS One 6, e24040.

41. Dukhande, V. V., Sherwood, A. R., and Gentry, M. S. (2010) Laforin-Nature Molecule Page. in Nature Molecule Pages.

42. Dukhande, V. V., Rogers, D. M., Roma-Mateo, C., Donderis, J., Marina, A., Taylor, A. O., Sanz, P., and Gentry, M. S. (2011). Laforin, a dual specificity phosphatase involved in Lafora disease, is present mainly as monomeric form with full phosphatase activity. PLoS One 6, e24040.

43. Edner, C., Li, J., Albrecht, T., Mahlow, S., Hejazi, M., Hussain, H., Kaplan, F., Guy, C., Smith, S. M., Steup, M., and Ritte, G. (2007). Glucan, water dikinase activity stimulates breakdown of starch granules by plastidial beta-amylases. Plant Physiol 145, 17-28.

44. Eisenthal, R., Danson, M. J., and Hough, D. W. (2007) Trends in biotechnology 25, 247-249.

45. Emsley, P., and Cowtan, K. (2004) Acta Crystallogr D Biol Crystallogr 60, 2126-2132

46. Emsley, P., Lohkamp, B., Scott, W. G., and Cowtan, K. (2010). Features and development of Coot. Acta Crystallogr D Biol Crystallogr 66, 486-501.

47. Fettke, J., Hejazi, M., Smirnova, J., Hochel, E., Stage, M., and Steup, M. (2009) J Exp Bot 60, 2907-2922 Fettke, J., Hejazi, M., Smirnova, J., Hochel, E., Stage, M., and Steup, M. (2009) J Exp Bot 60, 2907-2922.

48. Fettke, J., Hejazi, M., Smirnova, J., Hochel, E., Stage, M., and Steup, M. (2009). Eukaryotic starch degradation: integration of plastidial and cytosolic pathways. J Exp Bot 60, 2907-2922.

49. Fordham-Skelton, A. P., Chilley, P., Lumbreras, V., Reignoux, S., Fenton, T. R., Dahm, C. C., Pages, M., and Gatehouse, J. A. (2002) The Plant Journal 29, 705-715.

50. Franko, M., and Ionescu-Pioggia, M. (2006) Making the Right Moves, HHMI and BWF, Chevy Chase, Md. & Research Triangle Park, N.C.

51. Fu, Y., Ballicora, M. A., Leykam, J. F., and Preiss, J. (1998) J Biol Chem 273, 25045-25052.

52. Gaffron, H. (1940) Am J Bot 27, 273-283.

53. Gaffron, H., and Rubin, J. (1942) J Gen Physiol 28, 269-285.

54. Gallant, D. J., Bouchet, B., and Baldwin, P. M. (1997). Microscopy of starch: evidence of a new level of granule organization. Carbohydrate Polymers 32, 177-191.

55. Ganesh, S., Tsurutani, N., Suzuki, T., Hoshii, Y., Ishihara, T., Delgado-Escueta, A. V., and Yamakawa, K. (2004). The carbohydrate-binding domain of Lafora disease protein targets Lafora polyglucosan bodies. Biochem Biophys Res Commun 313, 1101-1109.

56. Gentry, M. S., and Pace, R. M. (2009) BMC Evol Biol 9, 138.

57. Gentry, M. S., Dowen, R. H., 3rd, Worby, C. A., Mattoo, S., Ecker, J. R., and Dixon, J. E. (2007) J Cell Biol 178, 477-488.

58. Gentry, M. S., and Pace, R. M. (2009). Conservation of the glucan phosphatase laforin is linked to rates of molecular evolution and the glucan metabolism of the organism. BMC Evol Biol 9, 138.

59. Gentry, M. S., Dixon, J. E., and Worby, C. A. (2009). Lafora disease: insights into neurodegeneration from plant metabolism. Trends Biochem Sci 34, 628-639.

60. Gentry, M. S., Dowen, R. H., 3rd, Worby, C. A., Mattoo, S., Ecker, J. R., and Dixon, J. E. (2007). The phosphatase laforin crosses evolutionary boundaries and links carbohydrate metabolism to neuronal disease. J Cell Biol 178, 477-488.

61. Gosling, P., Noordam, B., Borchardt, J. K., Fiske, P., Kelner, K., Hitt, E., Jensen, D. G., Aschwanden, C., Vastag, B., Webb, S., Gaidos, S., Adams, J. U., Bonetta, L., Levine, I. S., and Hede, K. (2010) Career Basics: Advice and Resources for Scientists. in Career Trends from Science Careers, AAAS/Science Business Office, Washington, D.C.

62. Hansen, P. I., Larsen, F. H., Motawia, S. M., Blennow, A., Spraul, M., Dvortsak, P., and Engelsen, S. B. (2008) Biopolymers 89, 1179-1193.

63. Hansen, P. I., Spraul, M., Dvortsak, P., Larsen, F. H., Blennow, A., Motawia, M. S., and Engelsen, S. B. (2009) Biopolymers 91, 179-193.

64. Hansen, P. I., Spraul, M., Dvortsak, P., Larsen, F. H., Blennow, A., Motawia, M. S., and Engelsen, S. B. (2009). Starch phosphorylation-maltosidic restraints upon 3'- and 6'-phosphorylation investigated by chemical synthesis, molecular dynamics and NMR spectroscopy. Biopolymers 91, 179-193.

65. Hasegawa, H., and Holm, L. (2009). Advances and pitfalls of protein structural alignment. Curr Opin Struct Biol 19, 341-348.

66. Hejazi, M., Fettke, J., Kotting, O., Zeeman, S. C., and Steup, M. (2009) Plant Physiol 152, 711-722 Hejazi, M., Fettke, J., Kotting, O., Zeeman, S. C., and Steup, M. (2009) Plant Physiol 152, 711-722.

67. Hejazi, M., Fettke, J., Kotting, O., Zeeman, S. C., and Steup, M. (2010). The Laforin-like dual-specificity phosphatase SEX4 from *Arabidopsis* hydrolyzes both C6- and C3-phosphate esters introduced by starch-related dikinases and thereby affects phase transition of alpha-glucans. Plant Physiol 152, 711-722.

68. Henrissat, B. (1991) Biochem J 280 (Pt 2), 309-316.

69. Henrissat, B., and Bairoch, A. (1993) Biochem J 293 (Pt 3), 781-788.

70. Holm, L., and Rosenstrom, P. (2010). Dali server: conservation mapping in 3D. Nucleic Acids Res 38, W545-549.

71. Hsu, S., Kim, Y., Li, S., Durrant, E. S., Pace, R. M., Woods, V. L., Jr., and Gentry, M. S. (2009) Biochemistry 48, 9891-9902.

72. Hunt, J. B., Callan, P. M., Atwell, R. H., Cortines, R. C., Edwards, V. B., Furman, J., and Kisber, M. H. (2008) Measuring Up 2008: The National Report Card on Higher Education. National Center for Public Policy and Higher Education, San Jose, Calif.

73. Jobling, S. (2004) Curr Opin Plant Biol 7, 210-218 Jobling, S. (2004) Curr Opin Plant Biol 7, 210-218.

74. Jung, S. K., Jeong, D. G., Yoon, T. S., Kim, J. H., Ryu, S. E., and Kim, S. J. (2007). Crystal structure of human slingshot phosphatase 2. Proteins 68, 408-412.

75. Kadziola, A., Sogaard, M., Svensson, B., and Haser, R. (1998). Molecular structure of a barley alpha-amylase-inhibitor complex: implications for starch binding and catalysis. J Mol Biol 278, 205-217.

76. Keeling, P. L., and Myers, A. M. (2010) Annu Rev Food Sci Technol 1, 271-303.

77. Kerk, D., Conley, T. R., Rodriguez, F. A., Tran, H. T., Nimick, M., Muench, D. G., and Moorhead, G. B. (2006) Plant J 46, 400-413.

78. Koropatkin, N. M., and Smith, T. J. (2010). SusG: a unique cell-membrane-associated alpha-amylase from a prominent human gut symbiont targets complex starch molecules. Structure 18, 200-215.

79. Kotting, O., Kossmann, J., Zeeman, S. C., and Lloyd, J. R. (2010) Curr Opin Plant Biol 13, 321-329.
80. Kotting, O., Kossmann, J., Zeeman, S. C., and Lloyd, J. R. (2010). Regulation of starch metabolism: the age of enlightenment? Curr Opin Plant Biol 13, 321-329.
81. Kotting, O., Pusch, K., Tiessen, A., Geigenberger, P., Steup, M., and Ritte, G. (2005) Plant Physiol 137, 242-252.
82. Kotting, O., Pusch, K., Tiessen, A., Geigenberger, P., Steup, M., and Ritte, G. (2005). Identification of a novel enzyme required for starch metabolism in *Arabidopsis* leaves. The phosphoglucan, water dikinase. Plant Physiol 137, 242-252.
83. Kotting, O., Santelia, D., Edner, C., Eicke, S., Marthaler, T., Gentry, M. S., Comparot-Moss, S., Chen, J., Smith, A. M., Steup, M., Ritte, G., and Zeeman, S. C. (2009) Plant Cell 21, 334-34.6
84. Kotting, O., Santelia, D., Edner, C., Eicke, S., Marthaler, T., Gentry, M. S., Comparot-Moss, S., Chen, J., Smith, A. M., Steup, M., Ritte, G., and Zeeman, S. C. (2009). STARCH-EXCESS4 is a laforin-like Phosphoglucan phosphatase required for starch degradation in *Arabidopsis thaliana*. Plant Cell 21, 334-346.
85. Kozlov, S. S., Blennow, A., Krivandin, A. V., and Yuryev, V. P. (2007) Int J Biol Macromol 40, 449-460.
86. Lee, B., and Richards, F. M. (1971). The interpretation of protein structures: estimation of static accessibility. J. Mol. Biol. 55, 379-400.
87. Machalek, A. Z., Davis, A., and Saltsman, K. (2005) Inside the Cell. (Services, U.S. D. o. H. a. H. ed., Washington, D.C.
88. Machovic, M., and Janecek, S. (2006). Starch-binding domains in the post-genome era. Cell Mol Life Sci 63, 2710-2724.
89. Makarova, V. V., Kosourov, S., Krendeleva, T. E., Semin, B. K., Kukarskikh, G. P., Rubin, A. B., Sayre, R. T., Ghirardi, M. L., and Seibert, M. (2007) Photosynth Res 94, 79-89
90. Malcata, F. X. (2011) Trends in biotechnology 29, 542-549
91. Melis, A., Seibert, M., and Ghirardi, M. L. (2007) Adv Exp Med Biol 616, 110-121.
92. Melis, A., Zhang, L., Forestier, M., Ghirardi, M. L., and Seibert, M. (2000) Plant Physiol 122, 127-136.
93. Mikkelsen, R., Mutenda, K. E., Mant, A., Schurmann, P., and Blennow, A. (2005) Proc Natl Acad Sci USA 102, 1785-1790.
94. Minassian, B. A., Lee, J. R., Herbrick, J. A., Huizenga, J., Soder, S., Mungall, A. J., Dunham, I., Gardner, R., Fong, C. Y., Carpenter, S., Jardim, L., Satishchandra, P., Andermann, E., Snead, O. C., 3rd, Lopes-Cendes, I., Tsui, L. C., Delgado-Escueta, A. V., Rouleau, G. A., and Scherer, S. W. (1998). Mutations in a gene encoding a novel protein tyrosine phosphatase cause progressive myoclonus epilepsy. Nat Genet 20, 171-174.
95. Moorhead, G. B., De Wever, V., Templeton, G., and Kerk, D. (2009). Evolution of protein phosphatases in plants and animals. Biochem J 417, 401-409.
96. Morell, M. K., and Myers, A. M. (2005) Curr Opin Plant Biol 8, 204-210.
97. Muhrbeck, P., and Eliasson, A. (1991). Influence on the naturally occurring phosphate esters on the crystillinity of potato starch. Journal of the Science of Food and Ariculture 55, 13-18.
98. Murshudov, G. N. (1997) Acta Crystallogr D Biol Crystallogr 53, 240-255.
99. Murshudov, G. N. (1997). Refinement of macromolecular structures by the maximum-likelihood method. Acta Crystallogr D Biol Crystallogr 53, 240-255.
100. Nielsen, M. M., Bozonnet, S., Seo, E. S., Motyan, J. A., Andersen, J. M., Dilokpimol, A., Abou Hachem, M., Gyemant, G., Naested, H., Kandra, L., Sigurskjold, B. W., and Svensson, B. (2009). Two secondary carbohydrate binding sites on the surface of barley alpha-amylase 1 have distinct functions and display synergy in hydrolysis of starch granules. Biochemistry 48, 7686-7697.
101. Niittyla, T., Comparot-Moss, S., Lue, W.-L., Messerli, G., Trevisan, M., Seymour, M. D. J., Gatehouse, J. A., Villadsen, D., Smith, S. M., Chen, J., Zeeman, S. C., and Smith, A. M. (2006) J. Biol. Chem. 281, 11815-11818.
102. Niittyla, T., Comparot-Moss, S., Lue, W. L., Messerli, G., Trevisan, M., Seymour, M. D., Gatehouse, J. A., Villadsen, D., Smith, S. M., Chen, J., Zeeman, S. C., and Smith, A. M. (2006). Similar protein phosphatases control starch metabolism in plants and glycogen metabolism in mammals. J Biol Chem 281, 11815-11818.
103. Otwinowski, Z., and Minor, W. (1997). Processing of X-ray diffraction data collected in oscillation mode. Macromolecular Crystallography, Pt A 276, 307-326.
104. Payan, F., and Qian, M. (2003). Crystal structure of the pig pancreatic alpha-amylase complexed with malto-oligosaccharides. J Protein Chem 22, 275-284.
105. Podolak, E. (2010) Traveling the pathway to independence. in BioTechniques.com, Biotechniques, New York.
106. Ragunath, C., Manuel, S. G., Venkataraman, V., Sait, H. B., Kasinathan, C., and Ramasubbu, N. (2008). Probing the role of aromatic residues at the secondary saccharide-binding sites of human salivary alpha-amylase in substrate hydrolysis and bacterial binding. J Mol Biol 384, 1232-1248.
107. Ral, J. P., Bowerman, A. F., Li, Z., Sirault, X., Furbank, R., Pritchard, J. R., Bloemsma, M., Cavanagh, C. R., Howitt, C. A., and Morell, M. K. (2012) Plant biotechnology journal
108. Ritte, G., Heydenreich, M., Mahlow, S., Haebel, S., Kotting, O., and Steup, M. (2006) FEBS Lett 580, 4872-4876.
109. Ritte, G., Heydenreich, M., Mahlow, S., Haebel, S., Kotting, O., and Steup, M. (2006). Phosphorylation of C6- and C3-positions of glucosyl residues in starch is catalysed by distinct dikinases. FEBS Lett 580, 4872-4876.
110. Ritte, G., Lloyd, J. R., Eckermann, N., Rottmann, A., Kossmann, J., and Steup, M. (2002) Proc Natl Acad Sci USA 99, 7166-7171.
111. Ritte, G., Lloyd, J. R., Eckermann, N., Rottmann, A., Kossmann, J., and Steup, M. (2002). The starch-related R1 protein is an alpha-glucan, water dikinase. Proc Natl Acad Sci USA 99, 7166-7171.
112. Roach, P. J. (2002). Glycogen and its metabolism. Curr Mol Med 2, 101-120.
113. Robert, X., Haser, R., Mori, H., Svensson, B., and Aghajari, N. (2005). Oligosaccharide binding to barley alpha-amylase 1. J Biol Chem 280, 32968-32978.
114. Roma-Mateo, C., Moreno, D., Vernia, S., Rubio, T., Bridges, T. M., Gentry, M. S., and Sanz, P. (2011) BMC Evol Biol 11, 225.
115. Roma-Mateo, C., Solaz-Fuster, M. C., Gimeno-Alcaniz, J. V., Dukhande, V. V., Donderis, J., Marina, A., Criado, O., Koller, A., Rodriguez de Cordoba, S., Gentry, M. S., and Sanz, P. (2011) Biochemical Journal 439, 265-275.
116. Sanderson, J. S., Daniels, R. D., Donald, A. M., Blennow, A., and Engelsen, S. r. B. (2006) Carbohydrate Polymers 64, 433-443.

117. Santelia, D., and Zeeman, S. C. (2011) Curr Opin Biotechnol 22, 271-280.
118. Santelia, D., and Zeeman, S. C. (2010). Progress in *Arabidopsis* starch research and potential biotechnological applications. Curr Opin Biotechnol 22, 271-280.
119. Santelia, D., Kotting, O., Seung, D., Schubert, M., Thalmann, M., Bischof, S., Meekins, D. A., Lutz, A., Patron, N., Gentry, M. S., Allain, F. H., and Zeeman, S. C. (2011) Plant Cell 23, 4096-4111.
120. Santelia, D., Kotting, O., Seung, D., Schubert, M., Thalmann, M., Bischof, S., Meekins, D. A., Lutz, A., Patron, N., Gentry, M. S., Allain, F. H., and Zeeman, S. C. (2011). The phosphoglucan phosphatase like sex Four2 dephosphorylates starch at the C3-position in *Arabidopsis*. Plant Cell 23, 4096-4111.
121. Schrodinger, L. (2010). The PyMOL Molecular Graphics System, Version 1.3.
122. Serratosa, J. M., Gomez-Garre, P., Gallardo, M. E., Anta, B., de Bernabe, D. B., Lindhout, D., Augustijn, P. B., Tassinari, C. A., Malafosse, R. M., Topcu, M., Grid, D., Dravet, C., Berkovic, S. F., and de Cordoba, S. R. (1999). A novel protein tyrosine phosphatase gene is mutated in progressive myoclonus epilepsy of the Lafora type (EPM2). Hum Mol Genet 8, 345-352. Services, U.S. D. o. H. a. H. (2007) The Structures of Life. (Services, H. a. H. ed., Washington, D.C. Services, U.S. D. o. H. a. H. (2007) The Structures of Life. (Services, H. a. H. ed., Washington, D.C.
123. Sevcik, J., Hostinova, E., Solovicova, A., Gasperik, J., Dauter, Z., and Wilson, K. S. (2006). Structure of the complex of a yeast glucoamylase with acarbose reveals the presence of a raw starch binding site on the catalytic domain. FEBS J 273, 2161-2171.
124. Sherwood, A. R., Paasch, B. C., Worby, C. A., and Gentry, M. S. (2013). A malachite green-based assay to assess glucan phosphatase activity. Anal Biochem 435, 54-56.
125. Silver, D. M., Silva, L. P., Issakidis-Bourguet, E., Glaring, M. A., Schriemer, D. C., and Moorhead, G. B. (2012) FEBS J.
126. Sivakumar, G., Xu, J., Thompson, R. W., Yang, Y., Randol-Smith, P., and Weathers, P. J. (2012) Bioresour Technol 107, 1-9.
127. Sokolov, L. N., Dominguez-Solis, J. R., Allary, A. L., Buchanan, B. B., and Luan, S. (2006) Proc Natl Acad Sci USA 103, 9732-9737
128. Streb, S., and Zeeman, S. C. (2013). Starch metabolism in *Arabidopsis*. Arabidopsis Book 10, e0160.
129. Tagliabracci, V. S., Turnbull, J., Wang, W., Girard, J. M., Zhao, X., Skurat, A. V., Delgado-Escueta, A. V., Minassian, B. A., Depaoli-Roach, A. A., and Roach, P. J. (2007). Laforin is a glycogen phosphatase, deficiency of which leads to elevated phosphorylation of glycogen in vivo. Proc Natl Acad Sci USA 104, 19262-19266.
130. Takeda Y, H. S. (1981). Studies on starch phosphate. Part 5. Reexamination of the action of sweet-potato bet-amylase on phosphorylated (1->4)-a-D-glucan. Carbohydr. Res. 89, 174-178.
131. Tester, R. F., and Debon, S. J. (2000) Int J Biol Macromol 27, 1-12 Tester, R. F., and Debon, S. J. (2000) Int J Biol Macromol 27, 1-12.
132. Tester, R. F., Karkalas, J., and Qi, X. (2004). Starch-composition, fine structure and architechture. Journal of Cereal Science 39, 151-165.
133. Tharanathan, R. N. (2005) Crit Rev Food Sci Nutr 45, 371-384 Tharanathan, R. N. (2005) Crit Rev Food Sci Nutr 45, 371-384.
134. Tiessen, A., Hendriks, J. H., Stitt, M., Branscheid, A., Gibon, Y., Farre, E. M., and Geigenberger, P. (2002) Plant Cell 14, 2191-2213.
135. Tilman, D., Socolow, R., Foley, J. A., Hill, J., Larson, E., Lynd, L., Pacala, S., Reilly, J., Searchinger, T., Somerville, C., and Williams, R. (2009) Science 325, 270-271
136. Tonks, N. K. (2006). Protein tyrosine phosphatases: from genes, to function, to disease. Nat Rev Mol Cell Biol 7, 833-846.
137. USDA. (2010) USDA Feed Grain Baseline, 2010-19. USDA USDA. (2010) USDA Feed Grain Baseline, 2010-19.
138. Van Veldhoven, P. P., and Mannaerts, G. P. (1987) Anal Biochem 161, 45-48 Van Veldhoven, P. P., and Mannaerts, G. P. (1987) Anal Biochem 161, 45-48.
139. Vander Kooi, C. W., Taylor, A. O., Pace, R. M., Meekins, D. A., Guo, H. F., Kim, Y., and Gentry, M. S. (2010) Proc Natl Acad Sci USA 107, 15379-15384.
140. Vander Kooi, C. W., Taylor, A. O., Pace, R. M., Meekins, D. A., Guo, H. F., Kim, Y., and Gentry, M. S. (2010). Structural basis for the glucan phosphatase activity of Starch Excess4. Proc Natl Acad Sci USA.
141. Wang, W., and Roach, P. J. (2004). Glycogen and related polysaccharides inhibit the laforin dual-specificity protein phosphatase. Biochem Biophys Res Commun 325, 726-730.
142. Weise, S. E., Aung, K., Jarou, Z. J., Mehrshahi, P., Li, Z., Hardy, A. C., Can, D. J., and Sharkey, T. D. (2012) Plant biotechnology journal 10, 545-554.
143. Winn, M. D., Ballard, C. C., Cowtan, K. D., Dodson, E. J., Emsley, P., Evans, P. R., Keegan, R. M., Krissinel, E. B., Leslie, A. G., McCoy, A., McNicholas, S. J., Murshudov, G. N., Pannu, N. S., Potterton, E. A., Powell, H. R., Read, R. J., Vagin, A., and Wilson, K. S. Overview of the CCP4 suite and current developments. Acta Crystallogr D Biol Crystallogr 67, 235-242.
144. Worby, C. A., Gentry, M. S., and Dixon, J. E. (2006). Laforin, a dual specificity phosphatase that dephosphorylates complex carbohydrates. J Biol Chem 281, 30412-30418.
145. Xiao, J., Engel, J. L., Zhang, J., Chen, M. J., Manning, G., and Dixon, J. E. (2011). Structural and functional analysis of PTPMT1, a phosphatase required for cardiolipin synthesis. Proc Natl Acad Sci USA 108, 11860-11865.
146. Yu, T. S., Kofler, H., Hausler, R. E., Hille, D., Flugge, U. I., Zeeman, S. C., Smith, A. M., Kossmann, J., Lloyd, J., Ritte, G., Steup, M., Lue, W. L., Chen, J., and Weber, A. (2001). The *Arabidopsis* sex1 mutant is defective in the R1 protein, a general regulator of starch degradation in plants, and not in the chloroplast hexose transporter. Plant Cell 13, 1907-1918.
147. Yuvaniyama, J., Denu, J. M., Dixon, J. E., and Saper, M. A. (1996). Crystal structure of the dual specificity protein phosphatase VHR. Science 272, 1328-1331.
148. Zeeman, S. C., Kossmann, J., and Smith, A. M. (2010) Annu Rev Plant Biol 61, 209-234.
149. Zeeman, S. C., Tiessen, A., Pilling, E., Kato, K. L., Donald, A. M., and Smith, A. M. (2002). Starch synthesis in *Arabidopsis*. Granule synthesis, composition, and structure. Plant Physiol 129, 516-529.

The invention claimed is:

1. A glucan phosphatase polypeptide variant comprising the sequence of SEQ ID NO: 1 or a fragment thereof having at least 330 amino acids and at least one amino acid mutation selected from the group consisting of Y139A, M204A, F235A, K237R, K237N, K237S, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A, wherein there are 1 to 4 amino acid mutations.

2. The glucan phosphatase polypeptide variant of claim 1, wherein the at least one amino acid mutation is located in a Dual Specificity Phosphatase (DSP) domain of the glucan phosphatase polypeptide.

3. The glucan phosphatase polypeptide variant of claim 1, comprising the sequence of SEQ ID NO: 1 having at least one amino acid mutations selected from the group consisting of Y139A, M204A, F235A, K237R, K237N, K237S, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A.

4. The glucan phosphatase polypeptide variant of claim 1, comprising the sequence of a SEQ ID NO: 1 having at least one amino acid mutations selected from the group consisting of Y139A, M204A, F235A, K237R, K237N, K237S, W314A, N326A, D328A, N332A, T201K, T201S, A202T, M204T, M204A, M204R, M204L, G205D, G205S, F235G, Y139A/F167A, W278A/W314A, W278A/F167A, N326A/N332A, N332A/K307A, A202T/G205D, F235G/K237N, Y139A/F167A/F235A, W278A/W314A/F167A, and N326A/N332A/K307A, and wherein 1 to 10 amino acids have been deleted from the N-terminus and 1 to 20 amino acids have been deleted from the C-terminus.

5. A method of producing starch, comprising:
providing a plant that produces a glucan phosphatase polypeptide variant of claim 1; and
collecting starch from the plant.

6. The method of claim 5, wherein the amino acid mutation is located in a Dual Specificity Phosphatase (DSP) domain of the glucan phosphatase polypeptide.

7. The method of claim 5, wherein the plant comprises a nucleotide encoding the glucan phosphatase polypeptide variant.

8. A cDNA molecule encoding the polypeptide of claim 1.

* * * * *